(12) United States Patent
Stover et al.

(10) Patent No.: US 12,171,766 B2
(45) Date of Patent: Dec. 24, 2024

(54) METHODS OF TREATING PATIENTS SUFFERING FROM BRAIN INJURY AND METHODS OF INCREASING THE VALUE OF THE EXTENDED GLASGOW OUTCOME SCALE OF PATIENTS SUFFERING FROM BRAIN INJURY

(71) Applicant: VERINOS OPERATIONS GMBH, Wuerzburg (DE)

(72) Inventors: John Stover, Wuerzburg (DE); Frank Tegtmeier, Wuerzburg (DE)

(73) Assignee: VERINOS OPERATIONS GMBH, Wuerzburg (DE)

( * ) Notice: Subject to any disclaimer, the term of this patent is extended or adjusted under 35 U.S.C. 154(b) by 0 days.

(21) Appl. No.: 18/073,897

(22) Filed: Dec. 2, 2022

(65) Prior Publication Data

US 2023/0172938 A1    Jun. 8, 2023

Related U.S. Application Data

(60) Provisional application No. 63/285,899, filed on Dec. 3, 2021.

(51) Int. Cl.
| | |
|---|---|
| C07D 475/08 | (2006.01) |
| A61K 31/519 | (2006.01) |
| A61P 25/00 | (2006.01) |

(52) U.S. Cl.
CPC ............ *A61K 31/519* (2013.01); *A61P 25/00* (2018.01)

(58) Field of Classification Search
CPC ...... C07D 475/08; A61K 31/519; A61P 25/00
See application file for complete search history.

(56) References Cited

U.S. PATENT DOCUMENTS

| | | | |
|---|---|---|---|
| 296,543 A * | 4/1884 | Dumke et al. | ....... A61K 31/519 |
| 8,222,828 B2 | 7/2012 | Muehlschlegel | |
| 10,016,431 B2 | 7/2018 | Scheurer et al. | |

FOREIGN PATENT DOCUMENTS

| | | |
|---|---|---|
| EP | 2926805 A1 | 10/2015 |
| WO | 2004084906 A1 | 10/2004 |
| WO | 2015150294 A1 | 10/2015 |

OTHER PUBLICATIONS

Journal of Neurotrauma 31:1599-1606, 2014, John F. Stover et al.*
International Search Report and Written Opinion issued in PCT/EP2021/084183 on Jul. 15, 2022 (15 pages).
Stover et al., "Nitric Oxide Synthase Inhibition with the Antipterin VAS203 Improves Outcome in Moderate and Severe Traumatic Brain Injury: A Placebo-Controlled Randomized Phase IIa Trial (NOSTRA)", Journal of Neurotrauma. vol. 31, No. 19, Oct. 1, 2014 (Oct. 1, 2014), pp. 1599-1606.
Tegtmeier et al., "Efficacy of Ronopterin (VAS203) in Patients with Moderate and Severe Traumatic Brain Injury (NOSTRA phase III trial): study protocol of a confirmatory, placebo-controlled, randomised, double blind, multi-centre study", Trials, vol. 21, No. 1, Dec. 1, 2020 (Dec. 1, 2020).
Terpolilli et al., "The novel nitric oxide synthase inhibitor 4-amino-tetrahydro-L-biopterine prevents brain edema formation and intracranial hypertension following traumatic brain injury in mice", Journal of Neurotrauma, vol. 26, No. 11, Nov. 3, 2009 (Nov. 3, 2009), pp. 1963-1975.
Bragge et al., A State-of-the-Science Overview of Randomized Controlled Trials Evaluating Acute Management of Moderate-to-Severe Traumatic Brain Injury. J Neurotrauma. Aug. 15, 2016;33(16):1461-78.
Huijben et al., Use and impact of high intensity treatments in patients with traumatic brain injury across Europe: a CENTER-TBI analysis. Crit Care. Feb. 23, 2021;25(1):78.
Jarrahi et al., Revisiting Traumatic Brain Injury: From Molecular Mechanisms to Therapeutic Interventions. Biomedicines. Sep. 29, 2020;8(10):389.
Marquez De La Plata et al., Impact of Age on Long-term Recovery From Traumatic Brain Injury. Arch Phys Med Rehabil. May 2008;89(5):896-903.
McMillan et al., The Glasgow Outcome Scale—40 years of application and refinement. Nat Rev Neurol. Aug. 2016;12(8):477-485.
Peeters et al., Epidemiology of traumatic brain injury in Europe. Acta Neurochir (Wien). Oct. 2015;157(10):1683-96.
Salter et al, "Assessment of Outcomes Following Acquired Brain Injury" available at https://erabi.ca/module-list.Module 17 © 2023 ERABI (94 pages).
Stein and Howard, "Why Did the Phase III Clinical Trials for Progesterone in TBI Fail? An Analysis of Three Potentially Critical Factors". Found in: New Therapeutics for Traumatic Brain Injury: Prevention of Secondary Brain Damage and Enhancement of Repair and Regeneration. 2017:3-18.
Steyerberg et al. Predicting Outcome after Traumatic Brain Injury: Development and International Validation of Prognostic Scores Based on Admission Characteristics. PLoS Med. Aug. 5, 2008;5(8):e165.
Stocchetti et al., Severe traumatic brain injury: targeted management in the intensive care unit. Lancet Neurol. Jun. 2017;16(6):452-464.
Stover et al., Nitric Oxide Synthase Inhibition with the Antipterin VAS203 Improves Outcome in Moderate and Severe Traumatic Brain Injury: A Placebo-Controlled Randomized Phase IIa Trial (NOSTRA). J Neurotrauma. Oct. 1, 2014;31(19):1599-606.

(Continued)

*Primary Examiner* — Brenda L Coleman
(74) *Attorney, Agent, or Firm* — Michael A. Whittaker

(57) ABSTRACT

The present invention relates to methods of treating a human patient suffering from brain injury. These method may comprise (starting) administering to a selected patient within a time period of ≤12 hours or within a time period of >12 hours after the occurrence of the brain injury a therapeutically effective amount of a biopterin compound such as 4-Amino-(6R,S)-5,6,7,8-tetrahydro-L-biopterin. The invention also relates to methods of increasing the value of the extended Glasgow Outcome Scale (eGOS) of patients suffering from brain injury, thereby improving the condition of the patient.

19 Claims, 43 Drawing Sheets

(56) References Cited

OTHER PUBLICATIONS

Tegtmeier et al., Efficacy of Ronopterin (VAS203) in Patients with Moderate and Severe Traumatic Brain Injury (NOSTRA phase III trial): study protocol of a confirmatory, placebo-controlled, randomised, double blind, multi-centre study. Trials. Jan. 14, 2020;21(1):80.
Terpolilli et al., The Novel Nitric Oxide Synthase Inhibitor 4-amino-tetrahydro-L-biopterine Prevents Brain Edema Formation and Intracranial Hypertension following Traumatic Brain Injury in Mice. J Neurotrauma. Nov. 2009;26 (11):1963-1975.

* cited by examiner

Fig. 1

Extended Glasgow Outcome Scale (eGOS)

| | | |
|---|---|---|
| Fully return to normal life | 8 Upper Good Recovery | Fully returned to normal life |
| Returned to normal life | 7 Lower Good Recovery | Resumption of normal life with some disabling due to neurological and / or psychological deficits |
| Able to participate | 6 Upper Moderate Disability | Some disability, independent at home and dependent outside, able to return to work |
| Independent | 5 Lower Moderate Disability | Some disability, independent at home and dependent outside, no return to work |
| No frequent help | 4 Upper Severe Disability | Patient can be left alone for more than 8 h/day |
| Conscious Frequent help | 3 Lower Severe Disability | Condition of mental and/or physical disability, patient can be left alone for less than 8 h/day |
| Alive | 2 Vegetative State | Condition of unawareness, only reflex responses, periods of spontaneous eye opening |
| Dead | 1 Dead | Dead |

Fig. 2

POST DISCHARGE
STRUCTURED INTERVIEW FOR GOSE

Respondent: ☐  0 = Patient alone   1 = Relative/friend/caretaker alone   2 = Patient plus relative/friend/caretaker

Conciousness:

1. Is the head-injured person able to obey simple commands or say any words?
   ○ Yes        ○ No (VS)

Note: anyone who shows the ability to obey even simple commands or utter any word or communicate specifically in any other way is no longer considered to be in vegetative state. Eye movements are not reliable evidence of meaningful responsiveness. Corroborate with nursing staff and/or other caretakers. Confirmation of VS requires full assessment.

Independence at home:

2a. Is the assistance of another person at home essential every day for some activities of daily living?
   ○ Yes        ○ No (VS)    If no: go to 3

Note: for a NO answer they should be able to look after themselves at home for 24 hours if necessary, though they need not actually look after themselves. Independence includes the ability to plan for and carry out the following activities: getting washed, putting on clean clothes without prompting, preparing food for themselves, dealing with callers and handling minor domestic crises. The person should be able to carry out activities without needing prompting or reminding and should be capable of being left alone overnight.

2b. Do they need frequent help of someone to be around at home most of the time?
   ○ Yes (lower SD)        ○ No (upper SD)

Note: for a NO answer they should be able to look after themselves at home up to eight hours during the day if necessary, though they need not actually look after themselves.

2c. Was the patient independent at home before the injury?
   ○ Yes        ○ No

Independence outside home:

3a. Are they able to shop without assistance?
   ○ Yes        ○ No (upper SD)

Note: this includes being able to plan what to buy, take care of money themselves and behave appropriately in public. They need not normally shop, but must be able to do so.

3b. Were they able to shop without assistance before?
   ○ Yes        ○ No

4a. Are they able to travel locally without assistance?
   ○ Yes        ○ No (upper SD)

Note: they may drive or use public transport to get around. Ability to use a taxi is sufficient, provided the person can phone for it themselves and instruct the driver.

4b. Were they able to travel locally without assistance before the injury?
   ○ Yes        ○ No

Work:

5a. Are they currently able to work (or look after others at home) to their previous capacity?
   ○ Yes    If yes, go to 6      ○ No 5b. How restricted are they?
   a. Reduced work capacity?                                   ○ a. (Upper MD)
   b. Able to work only in a sheltered workshop or             ○ b. (Lower MD)
      non-competitive job or currently unable to work?

Fig. 2 (continued)

5c. Does the level of restriction represent a change in respect to the pre-trauma situation?
　　　　　○ Yes　　　　　○ No

Social and Leisure activities:

6a. Are they able to resume regular social and leisure activities outside home?
　　　　　○ Yes　If yes, go to 7　　　○ No Note: they need not have resumed all their previous leisure activities, but should not be prevented by physical or mental impairment. If they have stopped the majority of activities because of loss of interest or motivation, then this is also considered a disability.

6b. What is the extent of restriction on their social and leisure activities?
　　a. Participate a bit less: at least half as often as before injury　　○ a. (Lower GR)
　　b. Participate much less: less than half as often　　　　　　　　　　○ b. (Upper MD)
　　c. Unable to participate: rarely, if ever, take part　　　　　　　　　○ c. (Lower MD)

6c. Does the extent of restriction in regular social and leisure activities outside home represent a change in respect or pre-trauma
　　　　　○ Yes　　　　　○ No

Family and friendships:

7a. Has there been family or friendship disruption due to psychological problems?
　　　　　○ Yes　　　　　○ No　If no, go to 8

Note: typical post-traumatic personality changes are: quick temper, irritability, anxiety, insensitivity to others, mood swings, depression and unreasonable or childish behaviour.

7b. What has been the extent of disruption or strain?
　　a. Occasional - less than weekly　　　　　　　　　　　○ a. (Lower GR)
　　b. Frequent - once a week or more, but not tolerable　○ b. (Upper MD)
　　c. Constant - daily and intolerable　　　　　　　　　　○ c. (Lower MD)

7c. Does the level of disruption or strain represent a change in respect to pre-trauma situation?
　　　　　○ Yes　　　　　○ No Note: if there were some problems before injury, but these have become markedly worse since the injury then answer yes to question

Return to normal life:

8a. Are there any other current problems relating to the injury which affect daily life?
　　　　　○ Yes (Lower GR)　　　○ No (Upper GR)

Note: other typical problems reported after head injury: headaches, dizziness, sensitivity to noise or light, slowness, memory failures and concentration problems.

8b. If similar problems were present before the injury, have these become markedly worse?
　　　　　○ Yes　　　　　○ No 9. What is the most important factor in outcome?
　　○ a. Effects of head injury
　　○ b. Effects of illness or injury to another part of the body
　　○ c. A mixture of these Note: extended GOS grades are shown beside responses on the CRF. The overall rating is based on the lowest outcome category indicated.
Areas in which there has been no change with respect to the pre-trauma situation are ignored when the overall rating is made

Fig. 3A

| Intervention | Intensity | Score |
|---|---|---|
| Head elevation | None | 0 |
| | > 0 < 30 | 1 |
| | > 30 | 2 |
| Sedation (maximum score = 8) *per own standard* | None | 0 |
| | Low dose | 1 |
| | Moderate dose | 2 |
| | High dose (no burst suppression) | 3 |
| | For every additional agent | plus 1 |
| | Intensive: high dose barbiturates or high dose propofol for burst suppression | 8 |
| Paralysis | No | 0 |
| | Yes | 1 |
| Hyperventilation | None | 1 |
| | Moderate   paCO2 > 30 < 35 mmHg | 2 |
| | Intensive   paCO2 < 30 mmHg | 3 |
| Increased oxygenation *per own standard* | No | 0 |
| | Moderate   FiO2 | 1 |
| | Intensive   FiO2 and PEEP | 2 |
| CPP *per own standard* | None | 1 |
| | Moderate (catecholamines and volume) | 2 |
| | Intensive (dito plus inotropics) | 3 |
| Cooling | None pharmacology | 1 |
| | Modest   35- 37 C | 2 |
| | Moderate   >33 <35 C | 3 |
| | Intensive   <33 C | 4 |
| Osmotherapy *per own standard* | None | 0 |
| | Moderate | 1 |
| | Intensive | 2 |
| CSF drainage | No | 0 |
| | < 1 ml/ h | 1 |
| | 1- 10 ml/ h | 2 |
| | > 10 ml/ h | 3 |
| RBC transfusion | No | 0 |
| | Yes | 1 |
| Surgery for mass lesion | No | 0 |
| | Yes | 1 |
| Decompressive craniectomy: *Note: To be scored also on consecutive days of procedure until skull is closed via cranioplasty* | No | 0 |
| | Unilateral | 5 |
| | Bilateral | 10 |
| Laparotomy to treat intracranial hypertension due to abdominal hypertension | No | 0 |
| | Yes | 10 |

Fig. 3B

Low TIL

| | | |
|---|---|---|
| Head elevation | 0 | 1 |
| Sedation | 0 | 1 |
| Paralysis | 0 | 0 |
| Hyperventilation | 1 | 1 |
| Increased oxygenation | 0 | 1 |
| CPP | 1 | 2 |
| Cooling | 1 | 2 |
| Osmotherapy | 0 | 1 |
| CSF drainage | 0 | 1 |
| RBC transfusion | 0 | |
| Surgery for mass lesion | 0 | |
| Decompressive craniectomy | 0 | |
| Laparotomy | 0 | |
| Sum | 3 | 10 |

| eGOS increase | Placebo | Ronopterin |
|---|---|---|
| +1 | 27 | 20 |
| +2 | 9 | 16 |
| +3 | 4 | 6 |
| +4 | 0 | 2 |
| ≥+2 | 13 | 24 |

| eGOS increase | Placebo | Ronopterin |
|---|---|---|
| +1 | 7 | 11 |
| +2 | 1 | 6 |
| +3 | 2 | 2 |
| +4 | 0 | 1 |
| ≥+2 | 3 | 9 |

Time to infusion > 12 hours

| eGOS increase | Placebo | Ronopterin |
|---|---|---|
| +1 | 20 | 9 |
| +2 | 8 | 10 |
| +3 | 2 | 4 |
| +4 | 0 | 1 |
| ≥+2 | 10 | 15 |

| eGOS increase | Placebo | Ronopterin |
|---|---|---|
| +1 | 14 | 11 |
| +2 | 6 | 10 |
| +3 | 3 | 4 |
| +4 | 0 | 0 |
| ≥+2 | 9 | 14 |

| eGOS increase | Placebo | Ronopterin |
|---|---|---|
| +1 | 5 | 9 |
| +2 | 0 | 2 |
| +3 | 1 | 2 |
| +4 | 0 | 0 |
| ≥+2 | 1 | 4 |

Patients of age 18 to 39 (< 40 years), Ronopterin: administration ≤ 12 hours: significantly more eGOS responders

| eGOS increase | Placebo | Ronopterin |
|---|---|---|
| +1 | 9 | 2 |
| +2 | 6 | 8 |
| +3 | 2 | 2 |
| +4 | 0 | 0 |
| ≥+2 | 8 | 10 |

| eGOS increase | Placebo | Ronopterin |
|---|---|---|
| +1 | 13 | 9 |
| +2 | 3 | 6 |
| +3 | 1 | 2 |
| +4 | 0 | 2 |
| ≥+2 | 4 | 10 |

| eGOS increase | Placebo | Ronopterin |
|---|---|---|
| +1 | 2 | 2 |
| +2 | 1 | 4 |
| +3 | 1 | 0 |
| +4 | 0 | 1 |
| ≥+2 | 2 | 5 |

≥ 40 years, Ronopterin administration ≤ 12 hours: trend to more eGOS responders

| eGOS increase | Placebo | Ronopterin |
|---|---|---|
| +1 | 11 | 7 |
| +2 | 2 | 2 |
| +3 | 0 | 2 |
| +4 | 0 | 1 |
| ≥+2 | 2 | 5 |

| eGOS increase | Placebo | Ronopterin |
|---|---|---|
| +1 | 24 | 16 |
| +2 | 6 | 14 |
| +3 | 3 | 6 |
| +4 | 0 | 2 |
| ≥+2 | 9 | 22 |

Ronopterin-group: more male patients with higher increase in eGOS over time; not significant Ronopterin-group: significantly less patients with decrease in eGOS over time; p=0.04

| eGOS increase | Placebo | Ronopterin |
|---|---|---|
| +1 | 6 | 10 |
| +2 | 0 | 6 |
| +3 | 2 | 2 |
| +4 | 0 | 1 |
| ≥+2 | 2 | 9 |

Ronopterin administration ≤ 12 hours: significantly more male eGOS responders

| eGOS increase | Placebo | Ronopterin |
|---|---|---|
| +1 | 18 | 6 |
| +2 | 6 | 8 |
| +3 | 1 | 4 |
| +4 | 0 | 1 |
| ≥+2 | 7 | 13 |

| eGOS increase | Placebo | Ronopterin |
|---|---|---|
| +1 | 3 | 4 |
| +2 | 3 | 2 |
| +3 | 1 | 0 |
| +4 | 0 | 0 |
| ≥+2 | 4 | 2 |

Ronopterin: less female patients with higher increase in eGOS over time; not significant

| eGOS increase | Placebo | Ronopterin |
|---|---|---|
| +1 | 1 | 1 |
| +2 | 1 | 0 |
| +3 | 0 | 0 |
| +4 | 0 | 0 |
| ≥+2 | 1 | 0 |

Ronopterin administration ≤ 12 hours: less female eGOS responders; BUT higher Good Recovery at 3 months

| eGOS increase | Placebo | Ronopterin |
|---|---|---|
| +1 | 2 | 3 |
| +2 | 2 | 2 |
| +3 | 1 | 0 |
| +4 | 0 | 0 |
| ≥+2 | 3 | 2 |

Fig. 15

| Time after TBI | Sex | Age | Time to infusion ≤ 12 hours | Time to infusion > 12 hours |
|---|---|---|---|---|
| 3 months | | | | |
| | Females (n=44) | | 1.4, 0.02-8.2 | 10.2, 0.5-204 |
| | | ≤ 39 years | 1.5, 0.06-41 | 1.3, 0.02-75 |
| | | ≥ 40 years | 1.3, 0.02-82 | 4.2, 0.2-102 |
| | Males (n=175) | | 0.4, 0.09-1.9 | 0.2, 0.05-0.6 |
| 6 months | | | | |
| | Females (n=44) | | 1.5, 0.2-23 | 5.5, 0.6-53 |
| | | ≤ 39 years | 6, 0.2-163 | 2.3, 0.2-33 |
| | | ≥ 40 years | 0.3, 0.01-11 | 6.2, 0.3-147 |
| | Males (n=179) | | 2.2, 0.6-7.6 | 0.6, 0.3-1.4 |
| | | ≤ 39 years | 1.4, 0.3-5.9 | 0.6, 0.2-1.6 |
| | | ≥ 40 years | 9, 0.4-194 | 0.6, 0.2-2.2 |

Early infusion: females and males, mainly < 40 years, males, ≥ 40 years
Late infusion: females, mainly ≥ 40 years Males: 3 months: less patients with eGOS ≥ 7 with Ronopterin 3 and 6 months: more female patients with eGOS ≥ 7 with Ronopterin

METHODS OF TREATING PATIENTS SUFFERING FROM BRAIN INJURY AND METHODS OF INCREASING THE VALUE OF THE EXTENDED GLASGOW OUTCOME SCALE OF PATIENTS SUFFERING FROM BRAIN INJURY

CROSS-REFERENCE TO RELATED APPLICATIONS

The present application claims the benefit of priority of U.S. Provisional Application No. 63/285,899, filed Dec. 3, 2021, the content of which is hereby incorporated by reference it its entirety for all purposes.

FIELD OF THE INVENTION

The present invention relates to the use of biopterin compounds such as 4-Amino-(6R,S)-5,6,7,8-tetrahydro-L-biopterin for treatment of patients suffering from brain injury. The invention also relates to the use of such biopterin compounds for increasing the value of the extended Glasgow Outcome Scale (eGOS) of patients suffering from brain injury, thereby improving the condition of the patient.

BACKGROUND OF THE INVENTION

Traumatic brain injury (TBI) is a major cause of mortality and long-term disability, with enormous impact on patients and their families (Stocchetti et al, Severe traumatic brain injury: targeted management in the intensive care unit. Lancet Neurol. 2017; 16:452-464). In Europe an overall incidence rate of 262 per 100,000 of hospital admitted TBI was reported in a meta-analysis, see Maas et al., Epidemiology of traumatic brain injury in Europe. Acta Neurochir (Wien). 2015 157:1683-96. The TBI related costs are high and accounted for 33 billion Euros in Europe in 2010. The high costs are owed to mostly to lifetime productivity losses, particularly when young people are affected, see Maas et al, vide supra.

Clinical trials in TBI with pharmacological interventions have failed so far most likely due to the heterogeneous complexity of the disease with a plethora of different treatment influences, See Bragge et al., A State-of-the-Science Overview of Randomized Controlled Trials Evaluating Acute Management of Moderate-to-Severe Traumatic Brain Injury. J Neurotrauma. 2016 and Stein et al, Chapter 1—Why Did the Phase III Clinical Trials for Progesterone in TBI Fail? An Analysis of Three Potentially Critical Factors in New Therapeutics for Traumatic Brain Injury: Prevention of Secondary Brain Damage and Enhancement of Repair and Regeneration, 2017, pages 3-18, ISBN 978-0-12-802686-1.

Pathophysiology of TBI is complex and involves a variety of processes including—among others—neuroinflammation, brain oedema formation and excitotoxicity (Jarrahi et al, Revisiting Traumatic Brain Injury: From Molecular Mechanisms to Therapeutic Interventions. Biomedicines. 2020; 8(10):389). Nitric oxide has been discussed as key player in the development of secondary injury after TBI. Inhibitors of Nitric oxide synthase have been tested in animal models of TBI with 4-amino-tetrahydrobiopterin (Ronopterin, VAS203) having been shown been shown to be beneficial in animal models of TBI (Terpolilli et al, The novel nitric oxide synthase inhibitor 4-amino-tetrahydro-L-biopterine prevents brain edema formation and intracranial hypertension following traumatic brain injury in mice. J Neurotrauma. 2009; 26: 1963-1975 and a phase II clinical trial (Stover et al., Nitric Oxide Synthase Inhibition with the Antipterin VAS203 Improves Outcome in Moderate and Severe Traumatic Brain Injury: A Placebo-Controlled Randomized Phase IIa Trial (NOSTRA), Journal of Neurotrauma, 2014 31:1-8). However, it is not yet clear whether 4-amino-tetrahydrobiopterin (Ronopterin, VAS203) is indeed suitable for treating brain injury such as traumatic brain injury.

It is thus an object of the present invention to provide methods of treating patients suffering from brain injury.

SUMMARY OF THE INVENTION

This object is solved by the aspects of the invention as defined in the claims, described in the description, and illustrated in the Examples and Figures.

In a first aspect, the invention provides a method of treating a human patient suffering from brain injury, wherein the method comprises administering to the patient within a time period of ≤12 hours after the occurrence of the brain injury a therapeutically effective amount of a compound having the formula (I):

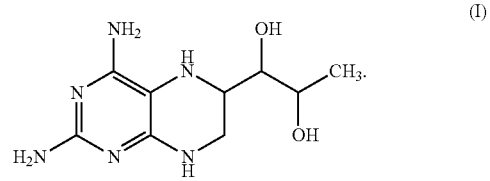 [SMILES: CC(O)C(O)C1CNc2nc(N)nc(N)c2N1]

In a second aspect, the invention provides a method of increasing the value of the Extended Glasgow Outcome Scale (eGOS) of a human patient suffering from brain injury, thereby improving the condition of the patient, wherein the value of the Extended Glasgow Outcome Scale (eGOS) of the patient reaches eGOS level 7 or eGOS level 8 six months after the occurrence of the brain injury, wherein the method comprises administering to the patient within a time period of ≤12 hours after the occurrence of the brain injury a therapeutically effective amount of a compound having the formula (I):

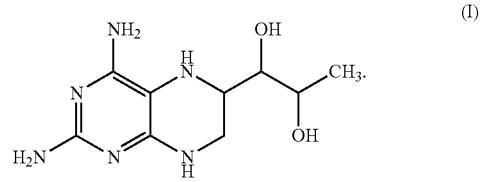 [SMILES: CC(O)C(O)C1CNc2nc(N)nc(N)c2N1]

In a third aspect, the invention provides a method of increasing the value of the Extended Glasgow Outcome Scale (eGOS) of a human patient suffering from brain injury, thereby improving the condition of the patient, wherein the value of the Extended Glasgow Outcome Scale (eGOS) of the patient has increased by 2 or more six months after the occurrence of the brain injury, compared to the eGOS value of the patient determined three months after the occurrence of the traumatic brain injury, wherein the method comprises administering to the patient within a time period of ≤12 hours after the occurrence of the brain injury a therapeutically effective amount of a compound having the formula (I):

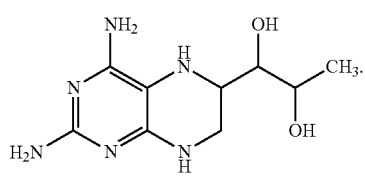 [SMILES: CC(O)C(O)C1CNc2nc(N)nc(N)c2N1]

In a fourth aspect, the invention provides a method of treating a human patient suffering from brain injury, wherein the patient is a female of an age of 40 years or older, and wherein the method comprises (starting) administering to the patient within a time period of >12 hours after the occurrence of the brain injury a therapeutically effective amount of a compound having the formula (I):

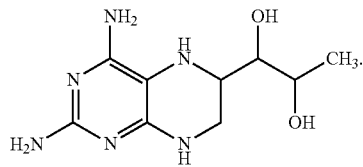

In one illustrative embodiment of this fourth aspect, the compound having the formula (I) is administered by infusion in a total dose of 17 mg/kg body weight over 48 hours, corresponding to a daily dose of 8.5 mg/kg body weight.

In a fifth aspect, the invention provides a method of treating a human patient suffering from brain injury, wherein the patient is of an age of 39 years or younger, and wherein the method comprises (starting) administering to the patient within a time period of >12 hours after the occurrence of the brain injury a therapeutically effective amount of a compound having the formula (I):

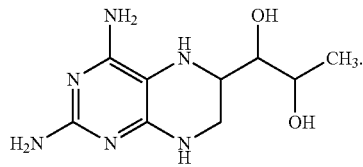 [SMILES: CC(O)C(O)C1CNc2nc(N)nc(N)c2N1]

In one illustrative embodiment of this fifth aspect, the compound having the formula (I) is administered by infusion in a total dose of 20 mg/kg body weight or in a total dose of 30 mg/kg body weight.

BRIEF DESCRIPTION OF THE DRAWINGS

The invention will be better understood with reference to the detailed description when considered in conjunction with the non-limiting examples and the drawings, in which:

FIG. 1 shows the Extended Glasgow Outcome Scale (eGOS) with its levels 1 to 8 as used herein as an outcome measure as brain injury;

FIG. 2 shows a standard questionnaire that is used for determining the eGOS level of a patient.

FIG. 3A shows an overview of the Therapy Intensity Level (TIL) treatment with the typical types of interventions used in the treatment of patients with brain injury together with the intensity of the intervention and their respective score, while FIG. 3B shows an exemplary TIL treatment with an index between 3 and 10 that can be used in the present invention.

FIG. 4A shows the change in eGOS from 3 to 6 months by eGOS level, FIG. 4B shows the change in eGOS from 3 to 6 months by category, FIG. 4C shows the increase of eGOS level by number of patients and FIG. 4D shows the odds-ratio for the eGOS increase. As seen from FIG. 4A Ronopterin-treated patients show an increase in eGOS levels up to 4 levels and the overall increase in eGOS by at least 2 levels is encountered more often in Ronopterin-treated patients (24 vs. 13 for the Ronopterin group, FIG. 4C). FIG. 4A shows for the Ronopterin-treated group more patients with higher increase in eGOS over time, however the increase is not (statistically) significant (FIG. 4D). In addition, FIG. 4A shows for the Ronopterin-treated group that there are less patients with a decrease in eGOS over time, however this decrease is not (statistically) significant.

FIGS. 5A-H show for the Ronopterin-treated group a significant increase in proportion of patients with increased eGOS.

In more detail, FIGS. 5A to 5D show the results for early infusion (≤12 hours), with FIG. 5A showing the change in eGOS from 3 to 6 months by eGOS level, FIG. 5B showing the change in eGOS from 3 to 6 months by category, FIG. 5C showing the increase of eGOS level by number of patients and FIG. 5D showing the odds-ratio for the eGOS increase. FIGS. 5A to 5D show that for early infusion (≤12 hours) Ronopterin-treated patients show an increase in eGOS levels up to 4 levels (FIG. 5A). FIG. 5C shows that overall, an increase in eGOS by at least 2 levels is encountered more often in Ronopterin-treated patients compared to placed (9 vs 3). The increase in proportion of patients with an increase by at least 1 level is significant compared to Placebo-treated patients. FIGS. 5E to 5H show the results for late infusion (>12 hours), with FIG. 5E showing the change in eGOS from 3 to 6 months by eGOS level, FIG. 5F showing the change in eGOS from 3 to 6 months by category, FIG. 5G showing the increase of eGOS level by number of patients and FIG. 5H showing the odds-ratio for the eGOS increase. Ronopterin-treated patients show an increase in eGOS levels up to 4 levels (FIG. 5E). Overall, increase in eGOS by at least 2 levels is encountered more often in Ronopterin-treated patients (15 vs 10), see FIG. 5G.

FIG. 6A shows the change in eGOS from 3 to 6 months by eGOS level, FIG. 6B shows the change in eGOS from 3 to 6 months by category, FIG. 6C shows the increase of eGOS level by number of patients and FIG. 6D shows the odds-ratio for the eGOS increase. Distribution of proportion of patients between Placebo and Ronopterin-treated patients with changes in eGOS from 3 to 6 months for patients aged 18-39 years. Ronopterin-treated patients show an increase in eGOS levels up to 3 levels (FIG. 6A). Overall, increase in eGOS by at least 2 levels is encountered more often in Ronopterin-treated patients (14 vs 9), see FIG. 6C. FIGS. 6A-D show that in the Ronopterin-treated group, there are more patients with higher increase in eGOS over time, however this increase is not significant (see FIG. 6D) while in the Ronopterin-treated group, there are less patients with decrease in eGOS over time, however this decrease is not significant.

FIGS. 7A to 7D show the results for early infusion (≤12 hours), with FIG. 7A showing the change in eGOS from 3 to 6 months by eGOS level, FIG. 7B showing the change in eGOS from 3 to 6 months by category, FIG. 7C showing the increase of eGOS level by number of patients and FIG. 7D showing the odds-ratio for the eGOS increase. FIGS. 7A to 7D show that for early infusion (≤12 hours) Ronopterin-treated patients show an increase in eGOS levels up to 3 levels (FIG. 7A). FIG. 7C shows that overall, an increase in eGOS by at least 2 levels is encountered more often in Ronopterin-treated patients compared to placed (4 vs 1). The increase in proportion of patients with an increase by at least 1 level is significant compared to Placebo-treated patients, see FIG. 7B and FIG. 7D. FIGS. 7E to 7H show the results for late infusion (>12 hours), with FIG. 7E showing the change in eGOS from 3 to 6 months by eGOS level, FIG. 7F showing the change in eGOS from 3 to 6 months by category, FIG. 7G showing the increase of eGOS level by number of patients and FIG. 7H showing the odds-ratio for the eGOS increase. Ronopterin-treated patients show an increase in eGOS levels up to 3 levels (FIG. 7E). Overall, increase in eGOS by at least 2 levels is encountered more often in Ronopterin-treated patients (10 vs 8), see FIG. 7G.

FIG. 8A shows the change in eGOS from 3 to 6 months by eGOS level, FIG. 8B shows the change in eGOS from 3 to 6 months by category, FIG. 8C shows the increase of eGOS level by number of patients and FIG. 8D shows the odds-ratio for the eGOS increase. As seen from FIG. 8A Ronopterin-treated patients show an increase in eGOS levels up to 4 levels and the overall increase in eGOS by at least 2 levels is encountered more often in Ronopterin-treated patients (10 vs. 4), see FIG. 8C. FIG. 8A shows for the Ronopterin-treated group more patients with higher increase in eGOS over time, however the increase is not (statistically) significant (FIG. 8D). In addition, FIG. 8A shows for the Ronopterin-treated group that there are less patients with a decrease in eGOS over time, however this decrease is not (statistically) significant.

FIGS. 9A to 9D show the results for early infusion (≤12 hours) with FIG. 9A showing the change in eGOS from 3 to 6 months by eGOS level, FIG. 9B showing the change in eGOS from 3 to 6 months by category, FIG. 9C showing the increase of eGOS level by number of patients and FIG. 9D showing the odds-ratio for the eGOS increase. As seen from FIG. 9A Ronopterin-treated patients show an increase in eGOS levels up to 4 levels and the overall increase in eGOS by at least 2 levels is encountered more often in Ronopterin-treated patients (5 vs. 2), see FIG. 9C. FIG. 9A to FIG. 9D show for patients with an age≥40 years and administration of Ronopterin ≤12 hours a trend to more patients with an increase in their eGOS levels (eGOS responders). FIGS. 9E to 9H show the results for late infusion (>12 hours), with FIG. 9E showing the change in eGOS from 3 to 6 months by eGOS level, FIG. 9F showing the change in eGOS from 3 to 6 months by category, FIG. 9G showing the increase of eGOS level by number of patients and FIG. 9H showing the odds-ratio for the eGOS increase. Ronopterin-treated patients show an increase in eGOS levels up to 4 levels (FIG. 9E). Overall, increase in eGOS by at least 2 levels is encountered more often in Ronopterin-treated patients (5 vs 2), see FIG. 9G.

FIG. 11A shows the change in eGOS from 3 to 6 months by eGOS level, FIG. 11B shows the change in eGOS from 3 to 6 months by category, FIG. 11C shows the increase of eGOS level by number of patients and FIG. 11D shows the odds-ratio for the eGOS increase. As seen from FIG. 11A Ronopterin-treated patients show an increase in eGOS levels up to 4 levels and the overall increase in eGOS by at least 2 levels is encountered more often in Ronopterin-treated patients (22 vs. 9), see FIG. 11C. FIGS. 11A-D show for the Ronopterin-treated group more patients with higher increase in eGOS over time, however the increase is not (statistically) significant (FIG. 11D). In addition, FIG. 11A shows for the Ronopterin-treated group that there are significantly less patients with a decrease in eGOS over time (p=0.04).

FIGS. 12A to 12D show the results for early infusion (≤12 hours) with FIG. 12A showing the change in eGOS from 3 to 6 months by eGOS level, FIG. 12B showing the change in eGOS from 3 to 6 months by category, FIG. 12C showing the increase of eGOS level by number of patients and FIG. 12D showing the odds-ratio for the eGOS increase. As seen from FIG. 12A Ronopterin-treated patients show an increase in eGOS levels up to 4 levels and the overall increase in eGOS by at least 2 levels is encountered more often in Ronopterin-treated patients (9 vs 2), see FIG. 12C. FIG. 12A to FIG. 12D show for male patients and administration of Ronopterin ≤12 hours that the increase in proportion of patients with an increase by at least 1 level is significant compared to Placebo-treated patients. FIG. 12E to FIG. 12H show the results for late infusion (>12 hours), with FIG. 12E showing the change in eGOS from 3 to 6 months by eGOS level, FIG. 12F showing the change in eGOS from 3 to 6 months by category, FIG. 12G showing the increase of eGOS level by number of patients and FIG. 12H showing the odds-ratio for the eGOS increase. Ronopterin-treated patients show an increase in eGOS levels up to 4 levels (FIG. 12E). Overall, increase in eGOS by at least 2 levels is encountered more often in Ronopterin-treated patients (13 vs 7), see FIG. 12G.

FIG. 13A shows the change in eGOS from 3 to 6 months by eGOS level, FIG. 13B shows the change in eGOS from 3 to 6 months by category, FIG. 13C shows the increase of eGOS level by number of patients and FIG. 13D shows the odds-ratio for the eGOS increase. As seen from FIG. 11A Ronopterin-treated patients show an increase in eGOS levels up to 2 levels and the overall increase in eGOS by at least 2 levels is encountered less often in Ronopterin-treated patients (2 vs 4), see FIG. 13C. FIG. 13A shows for the Ronopterin-treated group less female patients with higher increase in eGOS over time, however the increase is not (statistically) significant (FIG. 13D).

FIGS. 14A to 14D show the results for early infusion (≤12 hours) with FIG. 14A showing the change in eGOS from 3 to 6 months by eGOS level, FIG. 14B showing the change in eGOS from 3 to 6 months by category, FIG. 14C showing the increase of eGOS level by number of patients and FIG. 14D showing the odds-ratio for the eGOS increase. As seen from FIG. 14A Ronopterin-treated patients show an increase in eGOS levels up to 2 levels and the overall increase in eGOS by at least 2 levels is encountered less often in Ronopterin-treated patients (0 vs 1), see FIG. 14C. FIG. 14A to FIG. 14D show for female patients and administration of Ronopterin ≤12 that there are less female eGOS responders but that there is higher Good Recovery at 3 months. FIG. 14E to FIG. 14H show the results for late infusion (>12 hours), with FIG. 14E showing the change in eGOS from 3 to 6 months by eGOS level, FIG. 14F showing the change in eGOS from 3 to 6 months by category, FIG. 14G showing the increase of eGOS level by number of patients and FIG. 14H showing the odds-ratio for the eGOS increase. Ronopterin-treated female patients show an increase in eGOS levels up to 2 levels (FIG. 14E). Overall, increase in eGOS by at least 2 levels is encountered less often in Ronopterin-treated patients (2 vs 3), see FIG. 14G.

FIG. 15 shows the impact of time to infusion, sex, and age on the proportion of Good Recovery (eGOS value of 7 or 8) in Placebo and Ronopterin-treated patients expressed as Odds Ratio with 95% Confidence Intervals. As evident from FIG. 15, early infusion (≤12 hours) is associated with higher Odds Ratio in favor of Ronopterin in female and male patients, mainly for the tested female patient population with an age of 18 to 39 years, i.e. <40 years and in male patients with an age of ≥40 years. Late infusion (>12 hours) is associated with higher Odds Ratio in favor of Ronopterin in female patients, mainly in the female patient population with an age≥40 years. (The high Confidence Intervals are related to the small number of patients in the sex- and age-dependent subgroups of analysis.) At 3 months, the Odds Ratios reveal that female patients show highest impact of Ronopterin compared to male patients: early infusion: 1.4, 0.02-8.2 vs 0.4, 0.09-1.9; late infusion: 10.2, 0.5-204 vs 0.2, 0.05-0.6). At 6 months, the Odds Ratios are higher in male patients compared to female patients (2.2, 0.6-7.6 vs 1.5, 0.2-23), especially with early infusion. With late infusion, the Odds Ratios are higher in female patients compared to male patients (5.5, 0.6-53 vs 0.6, 0.3-1.4).

FIG. 16A shows the proportion of patients for the 8 eGOS levels in Placebo and Ronopterin-treated patients at 3 months in male patients, FIG. 16B shows the proportion of patients for the 8 eGOS levels in Placebo and Ronopterin-treated patients at 6 months in male patients, FIG. 16C shows the proportion of patients for the 8 eGOS levels in Placebo and Ronopterin-treated patients at 3 months in female patients and FIG. 16D shows the proportion of patients for the 8 eGOS levels in Placebo and Ronopterin-treated patients at 6 months in female patients. As can be seen from FIG. 16, at 3 months, male patients show lower proportion of eGOS levels 7 and 8 (Good Recovery) compared to female patients, reflecting more beneficial impact in female patients. At 6 months, male patients show an increase in proportion of eGOS levels 7 and 8 compared to 3 months. Female patients show an increase in Good Recovery from 3 to 6 months.

FIG. 17A shows the proportion of patients for the 8 eGOS levels in Placebo and Ronopterin-treated patients at 3 months in male patients for early infusion (≤12 hours), FIG. 17B shows the proportion of patients for the 8 eGOS levels in Placebo and Ronopterin-treated patients at 6 months in male patients for late infusion (>12 hours), FIG. 17C shows the proportion of patients for the 8 eGOS levels in Placebo and Ronopterin-treated patients at 6 months in male patients for early infusion (≤12 hours) and FIG. 17D shows the proportion of patients for the 8 eGOS levels in Placebo and Ronopterin-treated patients at 6 months in male patients for late infusion (>12 hours). As can be seen from FIGS. 17-A-D, early infusion (≤12 hours) is associated with an increase in proportion of male patients with Good Recovery (eGOS 7 and 8) exceeding the proportion in Placebo-treated patients from 3 to 6 months. Late infusion (>12 hours) is associated with an increase in proportion of male patients with Good Recovery (eGOS 7 and 8) which, however, is less pronounced compared to Placebo-treated patients from 3 to 6 months. Overall, early infusion is associated with higher proportion of Good Recovery at 6 months in the Ronopterin-treated male patients.

FIG. 18A shows the proportion of patients for the 8 eGOS levels in Placebo and Ronopterin-treated patients at 3 months in female patients for early infusion (≤12 hours), FIG. 18B shows the proportion of patients for the 8 eGOS levels in Placebo and Ronopterin-treated patients at 6 months in female patients for late infusion (>12 hours), FIG. 18C shows the proportion of patients for the 8 eGOS levels in Placebo and Ronopterin-treated patients at 6 months in female patients for early infusion (≤12 hours) and FIG. 18D shows the proportion of patients for the 8 eGOS levels in Placebo and Ronopterin-treated patients at 6 months in female patients for late infusion (>12 hours). As evident from FIGS. 18A-D, early infusion (≤12 hours) is associated with an increase in proportion of female patients with Good Recovery (eGOS 7 and 8) exceeding the proportion in Placebo-treated patients from 3 to 6 months. Late infusion (>12 hours) is associated with an increase in proportion of female patients with Good Recovery (eGOS 7 and 8) exceeding the proportion in Placebo-treated patients from 3 to 6 months. Overall, early infusion is associated with higher proportion of Good Recovery at 6 months in the Ronopterin-treated female patients.

DETAILED DESCRIPTION OF THE INVENTION

Figure 4A:
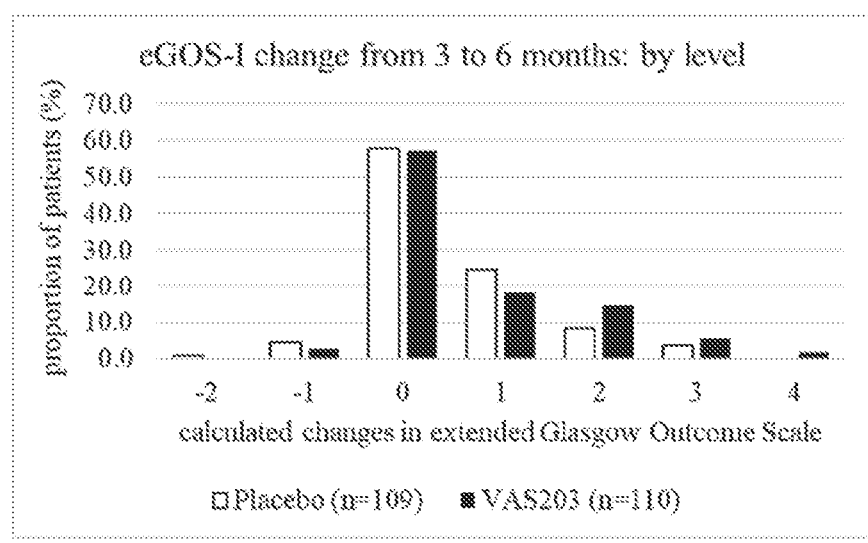
FIGS. 4A-D show the distribution of proportion of patients between Placebo and Ronopterin (VAS203)-treated patients reflecting changes in eGOS from 3 to 6 months for all patients and all times to infusion.

While 4-amino-tetrahydrobiopterin (also known by its international nonproprietary name (INN) Ronopterin, or as VAS203) has been assumed to be therapeutically effective in the treatment of brain injury such as traumatic brain injury, it has been surprisingly found in the present application that the therapeutic efficacy of 4-amino-tetrahydrobiopterin depends on a) the time point at which 4-amino-tetrahydrobiopterin is administered and b) on the patient population that is to be treated.

So, it has been surprisingly found here that administering Ronopterin to patients suffering from brain injury and who are 39 years or younger within a time period of ≤12 hours after the occurrence of the brain injury leads to patients reaching Extended Glasgow Outcome Scale (eGOS) level 7 or eGOS level 8, that means full neurologic recovery. In this group of patients at an age of 39 or younger it has also been found that female patients reach eGOS levels 7 or 8 already three months after the occurrence of the brain injury, while male patients reach eGOS levels 7 or 8 only six months after the occurrence of the brain injury (see, for example FIGS. 10 and 16). To the contrary, it has been found herein that female patients of an age of 40 years or older reach eGOS levels 7 or 8 when administration of Ronopterin is started within a time period of >12 hours after the occurrence of the brain injury. Notably, in all patient groups/populations examined herein it has been found that Ronopterin is therapeutically effective with patients of all subpopulations reaching eGOS levels 7 or 8, meaning full neurologic recovery from the brain injury. This therapeutic efficacy of Ronopterin found herein is also reflected by its ability to increase the eGOS level of the patient by 1, 2, 3, or even 4 levels, six months after the occurrence of the brain injury, compared to the eGOS value determined three months after the occurrence of the brain injury. Thus, administration of Ronopterin as practiced here will allow patients who, after three months may still be determined to have an eGOS value of 2 or 3 to reach an eGOS value of 7 or 8 six months after occurrence of the traumatic brain injury.

Thus, the present invention provides for the first time a drug (Ronopterin) that allows patients suffering from brain injury to fully recover from their brain injury, thereby finally providing a long-awaited solution to the unmet medical need to be able to treat, for example, traumatic brain injury. Accordingly, the present invention provides a real breakthrough, far and foremost by allowing patients to fully recover from traumatic brain injury but also in terms of reducing the TBI related high costs described above. In this context, it is exemplary referred to the population of female patients at an age of 40 years and older, for which administration of Ronopterin at a time period >12 hours after occurrence of the traumatic brain injury allows such female patients to reach an eGOS level of 7 or 8 even only three months after occurrence of the traumatic brain injury. Such fully recovered patients can thus be released from hospital or from rehabilitation early, thereby reducing the treatment costs significantly. It is also noted here that the present invention provides the added advantage that patients receiving Ronopterin as described herein only require, while being hospitalized, an accompanying low Therapy Intensity Level (TIL) treatment and not a high Therapy Intensity Level (TIL) treatment which has so far been used in trying to treat patients with traumatic brain injury (see Huijben et al, Use and impact of high intensity treatments in patients with traumatic brain injury across Europe: a CENTER-TBI analysis, Crit Care (2021) pages 25-78).

The invention will be further explained in the following making reference to either, several or all of these aspects. If reference is only made to one of these aspects, it is understood by the person skill in the art, that this reference nevertheless includes references to all other aspects of the invention, if applicable.

Starting with the first aspect, the invention provides a method of treating a human patient suffering from brain injury, wherein the method comprises administering to the patient within a time period of ≤12 hours after the occurrence of the brain injury a therapeutically effective amount of a compound having the formula (I):

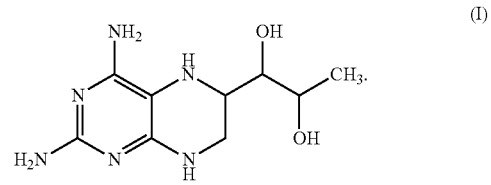 [SMILES: CC(O)C(O)C1CNc2nc(N)nc(N)c2N1]

In this context, "administering to the patient within a time period of ≤12 hours after the occurrence of the brain injury" means that the administration of the compound of formula (I) such as Ronopterin starts within any time in between the time period of ≤12 hours after the occurrence of the brain injury and will continue as long as necessary. For example, the administration can start as early as 3 hours or 4.5 hours after the occurrence of the brain injury (for example, if a patient is hospitalized very shortly after, for example, an accident that leads to the brain injury). The administration may, however, also start within a time period of between 6 to 12 hours after the occurrence of the brain injury, for example, 6, 7, or 10 hours after the occurrence of the brain injury. Regardless of whether the administration starts earlier or later than 6 hours after occurrence of the brain injury, the administration will in any case continue for a suitable time period as specified herein.

In this context, also the aspect of the invention, in which the administration of the compound of formula (I) such as Ronopterin starts within any time later than 12 hours after the occurrence of the brain injury is addressed. With respect to this aspect "administering to the patient within a time period of >12 hours after the occurrence of the brain injury" means that the administration of the compound of formula (I) such as Ronopterin can start within any time later than 12 hours after the occurrence of the brain injury as long as the administration is considered therapeutically useful. Also in this aspect the administration will continue as long as necessary. For example, the administration can start as early as 12 hours, for example, 12.1 hours after the occurrence of the brain injury (if such an accurate determination of the time that has lapsed since the brain injury can be made) but also only 13, 14, 15, 16, 17, 18, 19 or even 20 hours after the occurrence of the brain injury.

The compound having the formula (I) can be administered by any suitable route of administration. Usually, the compound of formula (I) is administered by infusion. The term "infusion" is used herein its regular meaning to refer to a continuous administration that takes place over a certain period of time. The administration/infusion can be carried over any time that has been found suitable. For example, such an administration may take over a period of about 12 to about 96 hours, a period of about 24 to about 72 hours or over a period of about 24 to about 48 hours. Thus, the administration may take place for about 1, 2, 3, 4, 5, 6, 7, 8, 9, 10, 11, 12, 13, 14, 15, 16, 17, 18, 19, 20, 21, 22, 23, 24, 32, 40, 48, 56, 68, 72, 86, or 96 hours. However, the administration via injection or infusion can also take longer than the time periods given above, if considered advantageous or necessary. For example, if the body weight of the patient is very high (which can be case of an obese patient) and a total dose of, for example 30 mg/kg body weight, cannot be administered within 72 hours, the administration time may be extended to over 72 hours. As another example, a higher total dosage to be administered may also require a longer infusion time. It is also possible to stop/pause the administration/infusion for a certain period of time, for example to avoid unwanted side effects of the compound of formula (I) such as nephrotoxicity. Such a pause may thus prolong an intended administration time of, for example, 48 or 72 hours by several hours. Typically, intravenous administration is used herein for the infusion. Intravenous administration is used in its regular term to mean the infusion or injection of a liquid directly into a vein, typically with a syringe and a hollow needle which is pierced through the skin to a sufficient depth for the material to be administered into the body of the subject.

The compound of formula (I) such as Ronopterin can be administrated in any dose that is therapeutically effective. The upper limit of the daily dose is usually a dose that is still safe to administer in terms of side effects such as nephrotoxicity. Typically, a compound of formula (I) such as Ronopterin is administered at a total dose in the range of 2.5 mg/kg body weight to 30.0 mg/kg body weight. Illustrative examples of suitable total doses of the compound formula (I) include 2.5, 5.0, 7.5, 8.5, 10.0, 12.5, 15.0, 17.5, 20.0, 22.5, 25.0 or 27.5 mg/kg body weight.

If a total dose of the compound of formula (I) of, for example, 17 mg/kg body weight of the patient is to be administered, the compound of formula (I) may be administered by infusion over 48 hours, corresponding to a daily dose of 8.5 mg/kg body weight. In yet another example, if a total dose of the compound of formula (I) of 20 mg/kg body weight is to be administered, the compound of formula (I) may be administered by infusion over 48 hours, corresponding to a daily dose of 10.0 mg/kg body weight. In yet another example, if a total dose of the compound of formula (I) of 30 mg/kg body weight is to be administered, the compound of formula (I) may be administered by infusion over 72 hours, corresponding (also) to a daily dose of 10.0 mg/kg body weight.

In this context, administration of a daily dose of 10.0 mg/kg body weight is in particular suitable for treating a patient suffering from brain injury, wherein the patient is of an age of 39 years or younger, and wherein the method comprises (starting) administering to the patient within a time period of >12 hours after the occurrence of the brain injury a therapeutically effective amount of a compound having the formula (I):

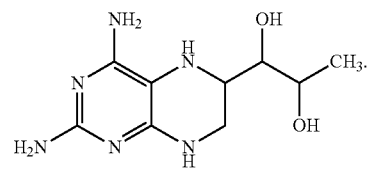 [SMILES: CC(O)C(O)C1CNc2nc(N)nc(N)c2N1]

If the compound of formula (I) is administered to this patient group (either male or female patients that are 39 years or younger) in a total dose of 20 mg/kg body weight, the compound of formula (I) may be administered by infusion over 48 hours, thus in a daily dose of 10.0 mg/kg body weight. Alternatively, if the compound of formula (I) is administered to this patient group in a total dose of 30 mg/kg body weight, the compound of formula (I) may be administered by infusion over 72 hours, and thus also in a daily dose of 10.0 mg/kg body weight.

Any type of brain injury can be treated by administration of the compound of formula (I) as described here. The brain injury may for example be traumatic brain injury, non-traumatic brain injury, elevated intracranial pressure, or secondary brain injury.

The term "traumatic brain injury" or "brain trauma" occurs when an external force traumatically injures the brain. TBI can be classified based on severity, mechanism (closed or penetrating head injury), or other features (e.g., occurring in a specific location or over a widespread area). A traumatic brain injury can occur as a consequence of a focal impact upon the head, by a sudden acceleration/deceleration within the cranium or by a complex combination of both movement and sudden impact, as well as blast waves, or penetration by a projectile or sharp, or dull object. The Glasgow Coma Scale (GCS), the most commonly used system for classifying TBI severity, grades a person's level of consciousness on a scale of 3-15 based on verbal, motor, and eye-opening reactions to stimuli. In general, it is agreed that a TBI with a GCS of 13 or above is mild, 9-12 is moderate, and 8 or below is severe. Similar systems exist for young children. From the diagnostic point of view, it is further distinguished between open and closed TBIs. An open TBI is considered to be an injury in which the protective barrier under the bone (cerebral meninges, dura mater) is mechanically destroyed and the brain is in contact with the external environment through this opening. Often, an open TBI is associated with the exit of liquor and brain tissue debris. In a closed TBI the skull or cranium remains intact, and the primary damage of the brain (trauma) is characterized by local lesions such as contusions or hematomas and/or diffuse cerebral tissue damage. The term "cranium" when referred to herein is the set of out of the neurocranium (braincase) and the viscerocranium (craniofacial) existing bony and cartilaginous head skeleton of vertebrates. "Intracranial" means within the cranium.

In accordance with the above, traumatic brain injury of any severity can be treated by the administration of the compound of formula (I) as described herein. Thus, the patient to be treated may, for example, have been diagnosed with complicated mild, moderate, or severe traumatic brain injury. In another illustrative example, patient to be treated may have been diagnosed with traumatic brain injury of a Glasgow Coma Score (GCS)≥3. The patient being assessed of having a Glasgow Coma Score (GCS)≥3 may require intracranial pressure (ICP) monitoring and thus may be taken care of in an intensive care unit (ICU). However, it is also possible that the patient does not require ICP monitoring and can, thus, be treated in a normal hospital ward. This may be in particular the case if the patient exhibits a TBI with a GCS of 9 or more, for example, a mild TBI (with a GCS above 13, see above) or a moderate TBI with a GCS of 9-12.

To the contrary, a "non-traumatic brain injury" does not involve external mechanical force to acquire a brain injury. Causes for non-traumatic brain injury may include lack of oxygen, glucose, or blood. Infections can cause encephalitis (brain swelling), meningitis (meningeal swelling), or cell toxicity as e.g. caused by fulminant hepatic failure, as can tumours or poisons. These injuries can occur through stroke, heart attack, near-drowning, strangulation or a diabetic coma, poisoning or other chemical causes such as alcohol abuse or drug overdose, infections or tumours and degenerative conditions such as Alzheimer's disease and Parkinson's disease. An acute neurodegenerative disease is represented by "stroke", which refers to the loss of brain function due to disturbances in the blood supply to the brain, especially when it occurs quickly, and is often associated with cerebrovascular disease. This can occur following ischemia (lack of blood flow) caused by blockage (thrombosis, arterial embolism), or a haemorrhage of central nervous system (CNS), or intracranial blood-vessels. As a result, the affected area of the brain cannot function normally. In accordance with the above, non-traumatic brain injury that can be treated with the invention as described here, may be ischemic/hypoxic/hemorrhagic brain injury (e.g. stroke), post-resuscitation (after e.g. cardiac arrest), subarachnoid haemorrhage, anticoagulation-induced haemorrhage or non-traumatic brain injury that is caused by inflammation and infection.

As an illustrative examples of a such an infection (disease) which can be treated is "meningitis", which is an acute inflammation of the membranes covering the brain and spinal cord, known collectively as the meninges. The inflammation may be caused by infection with viruses, bacteria, or other microorganisms, and less commonly by certain drugs. Encephalitis is another example of an infection that can be treated with the compound of formula (I) as described herein. In another example, the inflammation may be Systemic Inflammatory Response Syndrome (SIRS).

In addition to the damage caused at the moment of injury, brain trauma (non-traumatic or traumatic brain injury) causes "secondary injury" or secondary brain injury", which refers to a variety of events that take place in the minutes and days following the injury. These processes, which include alterations in cerebral blood flow and the pressure within the skull, contribute substantially to the damage from the initial injury. Secondary injury events may include local changes for example damage to the blood-brain barrier, release of factors that cause inflammation, free radical overload, excessive release of the neurotransmitter glutamate (excitotoxicity), influx of calcium and sodium ions into neurons, and dysfunction of mitochondria. Injured axons in the brain's white matter may separate from their cell bodies as a result of secondary injury, potentially killing those neurons. Other factors in secondary injury are changes in the blood flow to the brain; repeated transient disintegrity of the blood brain barrier; ischemia (insufficient blood flow); cerebral hypoxia (insufficient oxygen in the brain); cerebral oedema (swelling of the brain); and raised intracranial pressure (the pressure within the skull). In addition to local alterations, systemic influences from SIRS, infections, low or elevated blood glucose levels, low or very high blood pressure, low oxygen, or low or elevated carbon dioxide levels may also cause secondary and additional brain injury. Thus, a secondary brain injury that can treated as described herein may comprise a condition selected from the group consisting of edema formation from local or global hypoxia, ischemia, inflammation with and without infection, acute and chronic neuroinflammation after traumatic brain injury and neoplasms with both benign neoplasms and malignant neoplasms being treatable.

It can also be that the intracranial pressure may elevate due to swelling or a mass effect from a lesion, such as a haemorrhage. As a result, cerebral perfusion pressure (the pressure of blood flow in the brain) is reduced; ischemia results. When the pressure within the skull rises too high, it can cause brain death or herniation, in which parts of the brain are squeezed by structures in the skull. The term "intracranial pressure" (ICP) means the pressure inside the cranium and thus in the brain tissue and cerebrospinal fluid (CSF). The body has various mechanisms by which it keeps the ICP stable, with CSF pressures varying by about 1 mmHg in normal adults through shifts in production and absorption of CSF. ICP is measured in millimeters of mercury (mmHg) and, at rest, is normally 7-15 mmHg for a supine adult. Changes in ICP are attributed to volume changes in one or more of the compartments contained in the cranium. An "elevated pressure in the cranium" or "elevated intracranial pressure" means an increased pressure in the cranium of a subject in comparison to a normal, healthy subject. As the ICP is normally between 7-15 mm Hg; thus at 20-25 mm Hg, the upper limit of normal, is already considered an elevated ICP and a treatment to reduce this pressure may be needed. Thus, as an elevated ICP can be considered any pressure higher that 20 mm Hg in the cranium of a supine subject, preferably a pressure is higher than 25 mm Hg, higher than 26 mm Hg, higher than 27 mm Hg, higher than 28 mm Hg, higher than 29 mm Hg, higher than 30 mm Hg, higher than 31 mm Hg, higher than 32 mm Hg, higher than 33 mm Hg, higher than 34 mm Hg or higher than 35 mm Hg.

As mentioned above, it has been found in the present invention that the age and the sex of the patient has to be considered for the treatment. Addressing first the age of the patient, the patient may be up to 39 years old. Alternatively, the patent may be 40 years or older. If the patient is 39 years or younger, the patient may either be a child of an age between 1 year to 10 years, or a teenager or adolescent of an age of 11 to 17 or an adult that has an age in the range of 18 to 39 years. If the patient is 40 years of age or older, the patient can have any age above for 40 years. Such a patient may have an age in the range of 40 to 90 years, 40 to 80 years, 40 to 70 years or 40 to 65 years or 40 to 60 years. The patient may thus have an age of 40, 41, 42, 43, 44, 45, 46, 47, 48, 49, 50, 51, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 years.

The therapeutic methods and uses of a compound of formula (I) as described herein comprise an improvement of the physiological condition of the patients suffering from brain injury such as traumatic or non-traumatic brain injury. The condition of the patient (as a result and a measure of the efficacy of the treatment, i.e. typically reduction of the severity of the brain injury) can be expressed by the Extended Glasgow Outcome Scale (eGOS). It is noted here that the original GOS and the subsequently developed extended GOS (eGOS or GOSE) are the most widely used outcome measure in studies of brain injury, as summarized in, for example, in the review article of McMillan et al., The Glasgow Outcome Scale—40 years of application and refinement, Nature Reviews Neurology volume 12, pages 477-485 (2016). As explained by McMillan et al, 2016, vide supra, the original GOS and the subsequently developed extended eGOS are recommended by several national public health bodies including the National Institute of Health (NIH) in the U.S. as the outcome measure for major trauma and head injury, respectively. As also explained by McMillan et al, vide supra, the suitability of the GOS and eGOS is inter alia based on its simplicity, short administration time, reliability and validity, stability, flexibility of administration (face-to-face, over the telephone and by post), cost-free availability and ease of access. While the original Glasgow Outcome Scale (GOS) rates patient status into one of five categories: Dead, Vegetative State, Severe Disability, Moderate Disability or Good Recovery, the Extended GOS (eGOS) as used herein provides a more detailed categorization into eight categories by subdividing the categories of severe disability, moderate disability and good recovery into a lower and upper category as follows:

TABLE 1

Extended Glasgow Outcome Scale (eGOS)

| Level/Value | Category/condition of the patient | Abbreviation |
|---|---|---|
| 1 | Death | D |
| 2 | Vegetative state, Condition of unawareness, only reflex responses, periods of spontaneous eye opening | VS |
| 3 | Lower severe disability, Condition of mental and/or physical disability, patient can be left alone for less than 8 h/day | SD− |
| 4 | Upper severe disability. Patient can be left alone for more than 8 h/day | SD+ |
| 5 | Lower moderate disability, Some disability, independent at home and dependent outside, no return to work | MD− |
| 6 | Upper moderate disability, Some disability, independent at home and dependent outside, able to return to work | MD+ |
| 7 | Lower good recovery, Resumption of normal life with some disabling due to neurological and/or psychological deficits | GR− |
| 8 | Upper good recovery, Fully returned to normal life | GR+ |

For the sake of clarity, it is noted that the eGOS levels/value as used herein refer to the Level as in given in Table and as also provided by FIG. 1. Thus, an eGOS level of 7 indicates lower good recovery of a patient, wherein the patient is able to resume normal life with some disabling due to neurological and/or psychological deficits, while the eGOS level of 8 refers to upper good recovery, with the patient having fully returned to normal life. The eGOS level/value of a patient can be determined by the respective standard questionnaire that is shown in FIG. 2 and that is available, for example, at https://www.sralab.org/rehabilitation-measures/glasgow-outcome-scale-extended. The questionnaire of FIG. 2 also illustrates the simplicity and flexibility of the eGOS determination via a face-to-face meeting, a telephone interview or and by post. It is also noted here that the eGOS value as an "outcome score" is assessed not immediately after the occurrence of the brain injury but after a certain period of time "post-injury" such a 3 months, 6 months, or 12 months after the occurrence of the brain injury. Indeed, assessment of the eGOS 3 months, 6 months, and 12 months post injury are the standard approach for assessing brain injury such as traumatic brain injury. In line with this standard practice, "3 months eGOS values" and "6 months eGOS values" have been used herein. It is of course also possible to use eGOS values determined at a different point to time. In this context, we note that the assessment of the eGOS value may not be taken at exactly the day that is 3 or 6 months after the brain injury but that day can deviate by a couple of days. For example, if the traumatic brain injury occurred on 1 February, the 3 months eGOS value does not necessarily have to be determined on 1 May but can also be determined in late April or early May, for example on 29 April or 5 May.

Before further discussing the eGOS levels observed herein after administration of a compound of formula (I), it is noted that the neurological condition of a patient that has suffered from brain injury such as traumatic brain injury can also be assessed/evaluated herein by other commonly used outcome scores such as the Disability Rating Scale (DRS) or the Functional Independence Measure (FIM). See, for example, Salter et al, Module 17 "Assessment of Outcomes Following Acquired Brain Injury" available at https://er-abi.ca/module-list/ which describes the Disability Rating Scale (page 14), the Functional Independence Measure (page 19) as well as the eGOS (page 30), or the corresponding book chapter of Salter et al. "Assessment of Outcomes Following Acquired Brain Injury" in Teasell R, Cullen N, Marshall S, Janzen S, Bayley M, editors. Evidence-Based Review of Moderate to Severe Acquired Brain Injury. Version 11.0: p 1-75. See also Marquez de la Plata e al, Arch Phys Med Rehabil. 2008 May; 89(5): 896-903 which compares the Disability Rating Scale, the Functional Independence Measure and the eGOS under clinical trial conditions.

Turning now to the observed changes in the eGOS values, the 3 months eGOS value is taken in the present invention as the reference to which a subsequent eGOS value such as the 6 months eGOS value is compared. Thus, a difference in the eGOS value of +1 means herein that the eGOS value at 6 month is 1 level higher than the eGOS value at 3 months, for example, since the patient has improved from eGOS level 4 to eGOS level 5 within the respective 3 months period.

Having this in mind it has been found herein that administration of the compound of formula (I) increases the value of the Extended Glasgow Outcome Scale (eGos) of the patient by at least 1 or at least 2 eGOS levels when assessed six months after the occurrence of the brain injury such as traumatic brain injury and when compared to the eGOS level of the patient 3 months after the occurrence of the trauma. Notably, regardless of which patient population is treated and the time point when the administration is started (i.e.

either at a time≤12 hrs our at a time>12 hrs), it has been found herein that administration of the compound of formula (I) increases the eGOS level of a patient by 2, 3, 4, 5 or even 6 levels six months after the occurrence of the brain injury compared to the eGOS level of the patient at 3 months (cf. the Experimental Section). Thus, the eGOS level of a patient can increase, for example, increase from 2 after three months to eGOS level 4, 5, 6, 7 or even 8 six months after the brain injury. In another example, the eGOS level of a patient can increase, for example, increase from 3 after three months to eGOS level 5, 6, 7 or 8 six months after the brain injury.

In this context it is also noted that regardless of which patient population is treated and the time point when the administration is started (i.e. either at a time≤12 hrs our at a time>12 hrs), by means of the administration of the compound of formula (I) patients reach eGOS level 7 or eGOS level 8 either already three months after or at least six months after the occurrence of the traumatic brain injury.

In one embodiment of the invention in which the compound of formula (I) is administered within time period of ≤12 hours after the occurrence of the traumatic brain injury, the patient is a male patient having an age of 39 years or below. Such a male patient may reach eGOS level 7 or eGOS level 8 six months after the traumatic brain injury. In accordance with this, in such a male patient (population), the value of the Extended Glasgow Outcome Scale (eGos) of the patient increases by at least 1 level, or at least 2 level, including by 3, 4 or 5 levels, when assessed six months after the occurrence of the traumatic brain injury, compared to the eGOS value of the patient determined three months after the traumatic brain injury, In another embodiment of the invention in which the compound of formula (I) is administered within a time period of ≤12 hours after the occurrence of the traumatic brain injury, the patient is a male patient having an age of 40 years or higher. Such a male patient may reach eGOS level 7 or eGOS level 8 six months after the traumatic brain injury. Accordingly, in such a male patient (population), the value of the Extended Glasgow Outcome Scale (eGos) of the patient increases by at least 1 level, or at least 2 levels, including by 3, 4 and 5 levels, when assessed six months after the occurrence of the traumatic brain injury, compared to the eGOS value of the patient determined three months after the traumatic brain injury.

In yet another embodiment of the invention in which the compound of formula (I) is administered within a time period of ≤12 hours after the occurrence of the brain injury, the patient is a female patient having an age of 39 years or below. Such a female patient may reach eGOS level 7 or eGOS level 8 already three months after, but at least six months after occurrence of the traumatic brain injury. In such a female patient (population), the value of the Extended Glasgow Outcome Scale (eGOS) of the patient increases by at least 1 level or at least 2 levels, including 3, 4 and 5 levels, when assessed six months after the occurrence of the traumatic brain injury, compared to the eGOS value of the patient determined three months after the traumatic brain injury.

Turning now to an embodiment of the invention in which the compound of formula (I) is administered within a time period of >12 hours (for example, 12, 13, 14, 15, 16, 17, 18, 19 or 20 hours, see above) after the occurrence of the brain injury, the patient is a female patient having an age of 40 years or older, for example, an age in the range of 40 to 60 years, or an age of 40 to 70 years, or an age in the range of 40 to 80 years or an age in the range of 40 to 90 years. For such a female patient (population), it has surprisingly been found that such an administration of the compound of formula (I) results in the female patient reaching eGOS level 7 or eGOS level 8 either already three months or at least six months after the traumatic brain injury. In such a female patient (population), the value of the Extended Glasgow Outcome Scale (eGOS) of the patient increases by at least 1 level or at least 2 levels, including 3, 4 and 5 levels, when assessed six months after the occurrence of the traumatic brain injury, compared to the eGOS value of the patient determined three months after the traumatic brain injury.

Turning now to a further advantage of the therapeutic use of the compound of formula (I) as described herein, the treatment comprises providing within a period of 14 days after occurrence of the traumatic brain injury the patient with (only) a low Therapy Intensity Level (TIL) treatment. The low Therapy Intensity Level (TIL) treatment may have a therapy index level of only between 3 and 10. The term "Therapy Intensity Level (TIL) treatment" is used herein in its regular meaning (cf. in this respect, for example, Huijben et al, Crit Care (2021, vide supra) and as illustrated by FIG. 3A which shows an overview of the Therapy Intensity Level (TIL) treatment with the typical types of interventions used in the treatment of patients with brain injury together with the intensity of the intervention and their respective score. FIG. 3B shows options for exemplary low TIL treatments that can be used herein and which yield an index between 3 and 10. In accordance with FIG. 3B a low TIL treatment used here may only comprise as interventions "Head elevation", "Sedation" and "Increased oxygenation" which together have a low TIL score of only 3. In another illustrative example of such a low TIL score treatment, this treatment may comprise as interventions "Head elevation", "Sedation", "Increased oxygenation", Cooling" and "Osmotherapy" which together have a low TIL score of only 6. The person skilled in the art is able to determine the appropriate low TIL treatment for each patient. In this context, it is pointed out again that it is an advantage of the present invention that patients receiving a compound of formula (I) such as Ronopterin as described herein require, while being hospitalized, only such a (supporting/accompanying) low Therapy Intensity Level (TIL) treatment. As evident, this reduces the work load and burden of the clinical staff taking care of the patients in the hospital significantly, in particular when patients are treated in the ICU.

Turning now to the compound of formula, the compound is typically 4-Amino-(6R,S)-5,6,7,8-tetrahydro-L-biopterin having the formula (Ia):

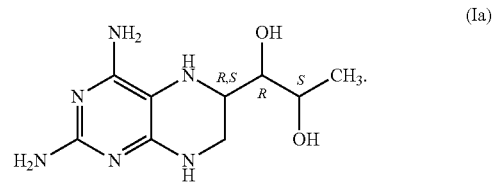

(Ia)

In accordance with the disclosure of, for example, European Patent 2 926 805, the corresponding U.S. Pat. No. 10,016,431 or the corresponding International Patent Application WO 2015/150294, the compound (Ia) may be a diastereomeric mixture that comprises more (6R)-4-Amino-5,6,7,8-tetrahydro-L-biopterin than (6S)-4-Amino-5, 6, 7, 8-tetrahydro-L-biopterin.

For administration of 4-Amino-5,6,7,8-tetrahydro-L-biopterin (Ronopterin) any suitable pharmaceutical composition containing 4-Amino-5,6,7,8-tetrahydro-L-biopterin can be used. Suitable formulations are described in International Patent Application WO 2004/084906, or the corresponding U.S. Pat. No. 8,222,828 as well as in European Patent 2 926 805, U.S. Pat. No. 10,016,431 or International Patent Application WO 2015/150294. The solid formulations described in U.S. Pat. No. 10,016,431 or WO 2015/150294 are particularly convenient for being used here since these solid formulations are stable for 36 months and provide a ready-to-use isotonic infusion solution with physiological pH (between 6.5 to 7.6) after reconstitution of a unit dosage with 50 mL water. The final concentration of Ronopterin in such a ready-to-use infusion solution is 20 mg/mL.

Accordingly, infusion of the compound of formula (I) such as Ronopterin can be carried out with a reconstituted solid composition of the compound of formula (I), wherein a unit dosage of the solid composition contains, as described in U.S. Pat. No. 10,016,431 or WO 2015/150294, 650±60 mg of the free base of 4-Amino-(6R,S)-5,6,7,8-tetrahydro-L-biopterin, 140±30 mg of water of crystallization, 70±7 mg $Na_2HPO_4 \cdot 2H_2O$, 16.5±2 mg $NaH_2PO_4 \cdot 2H_2O$, and 350±30 mg NaCl. Alternatively, and as also described in U.S. Pat. No. 10,016,431 or WO 2015/150294, a unit dosage of the solid composition may contain 650±60 mg of the free base of 4-Amino-(6R,S)-5,6,7,8-tetrahydro-L-biopterin, 60±50 mg of water of crystallization, 70±7 mg $Na_2HPO_4 \cdot 2H_2O$, 12±2.5 mg $NaH_2PO_4 \cdot 2H_2O$, and 350±30 mg NaCl. In accordance with the above, the reconstitution then comprises providing a vial containing 1 g of the unit dosage and adding 50 ml water to 1 g of the unit dosage to yield a ready-to-use infusion solution with a concentration of Ronopterin of 20 mg/mL. Such an infusion solution can then be administered (infused) to a patient (population) as described here, for a suitable period of time (such as 12 to 96 hours) starting with the administration either within a time period of ≤12 hours or within a time period of >12 hours.

In accordance with the above disclosure, a further aspect of the invention is directed to a method of treating a human patient suffering from brain injury, wherein the patient is a female of an age of 40 years or older, and wherein the method comprises (starting) administering to the patient within a time period of >12 hours after the occurrence of the brain injury a therapeutically effective amount of a compound having the formula (I):

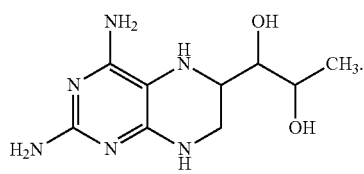

(I)

The patient populations, dosages, administration times and formulations as disclosed for the use of a compound of formula (I) in the first aspect of the invention equally apply to this second aspect.

A third aspect of the present invention relates to a method of increasing the value of the Extended Glasgow Outcome Scale (eGOS) of a human patient suffering from brain injury, thereby improving the condition of the patient, wherein the value of the Extended Glasgow Outcome Scale (eGOS) of the patient reaches eGOS level 7 or eGOS level 8 six months after the occurrence of the brain injury, wherein the method comprises (starting) administering to the patient within a time period of ≤12 hours after the occurrence of the brain injury a therapeutically effective amount of a compound having the formula (I):

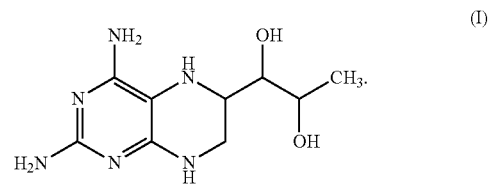

(I)

In this aspect, the eGOS value of the patient when assessed six months after the occurrence of the traumatic brain injury can have increased by 1, 2, 3, 4, 5, or 6 eGOS levels compared to the eGOS value of the patient determined three months after the occurrence of the traumatic brain injury.

The patient populations, dosages, administration times and formulations as disclosed for the use of a compound of formula (I) in the first aspect of the invention equally apply to this third aspect.

A fourth aspect of the present invention relates to a method of increasing the value of the Extended Glasgow Outcome Scale (eGOS) of a human patient suffering from brain injury, thereby improving the condition of the patient, wherein the value of the Extended Glasgow Outcome Scale (eGOS) of the patient has increased by 2 or more six months after the occurrence of the brain injury and compared to the eGOS value determined three months after the occurrence of the brain injury. This method comprises (starting) administering to the patient within a time period of ≤12 hours after the occurrence of the brain injury a therapeutically effective amount of a compound having the formula (I):

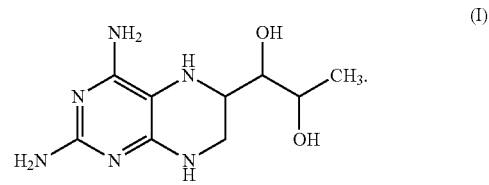 [SMILES: CC(O)C(O)C1CNc2nc(N)nc(N)c2N1]

(I)

By means of this method, the value of the Extended Glasgow Outcome Scale (eGOS) of the patient can have increased by 1, 2, 3, 4, 5, or 6 level six months after the occurrence of the brain injury, when compared to the eGOS value determined three months after the occurrence of the brain injury. Also in this method administering a compound of formula (I) results in the value of the Extended Glasgow Outcome Scale (eGOS) of the patient reaching eGOS level 7 or eGOS level 8 six months after the occurrence of the brain injury.

The dosages, administration times and formulations as disclosed for the use of a compound of formula (I) in the first aspect of the invention equally apply to this fourth aspect.

The invention will be further illustrated by the following non-limiting Experimental Examples.

EXAMPLES

The following examples further illustrate the invention. These examples should however not be construed as to limit the scope of this invention. The examples are included for purposes of illustration and the present invention is limited only by the claims.

Example 1: Manufacturing of Ronopterin

Ronopterin (VAS203) is prepared in a multistep synthesis starting from commercially available L-biopterin as described in Example 1 of, for instance, U.S. Pat. No. 10,016,431 or WO 2015/150294.

Example 2: Manufacturing of Solid Ronopterin Containing Composition (Drug Product)

Ronopterin (VAS203) is supplied as a sterile, white to pale red or brown lyophilised powder filled in 50 mL glass vials under nitrogen as a protective atmosphere. Each vial contains 650±60 mg of the free base of 4-Amino-(6R,S)-5, 6,7,8-tetrahydro-L-biopterin and 140±30 mg of water of crystallisation. Additionally, the vials contain 350±30 mg sodium chloride (NaCl), 70±7 mg disodium hydrogen phosphate dihydrate ($Na_2HPO_4 \cdot 2H_2O$), and 16.5±2 mg sodium dihydrogen phosphate dihydrate ($NaH_2PO_4 \cdot 2H_2O$). The limits of tolerance of the drug product composition are relatively high (±10%). The reason for this is the variation of the hydrochloride content of Ronopterin. The hydrochloride content of Ronopterin varies from batch to batch up to 10% (from 2.03 HCl to 2.24 HCl). During the preparation of the drug product the hydrochloride was neutralised in the present invention by addition of sodium hydroxide and sodium-phosphate buffer to obtain an isotonic solution with a physiological pH value. Therefore, also the content of the molecules generated during neutralisation (sodium chloride, disodium hydrogen phosphate and sodium dihydrogen phosphate) varies according to the hydrochloride content of the respective Ronopterin batch. The given limits of tolerance are necessary to meet the specifications of the quality relevant parameters pH and osmolality. The qualitative composition of 1 g Ronopterin vials is listed in Table 2.

TABLE 2

| Component | Reference to standards | Function |
|---|---|---|
| 4-Amino-(6R,S)-5,6,7,8-tetrahydro-L-biopterin | In house | Active ingredient |
| Sodium chloride* | Ph. Eur. | Osmolarity |
| Disodium hydrogen phosphate dihydrate | Ph. Eur. | Buffer |
| Sodium dihydrogen phosphate dihydrate | Ph. Eur. | Buffer |
| Water for injection (aqua ad inject.) | Ph. Eur. | Solvent used for reconstitution |
| Nitrogen | Ph. Eur. | Protective atmosphere |

*Sodium chloride is generated during the preparation of the formulation when the hydrochloride of the drug substance reacts with the sodium hydroxide solution. Both ingredients comply with the European Pharmacopoeia.

Pharmaceutical Composition

A solid lyophilised dosage form of Ronopterin as described in U.S. Pat. No. 10,016,431 or WO 2015/150294 was used here for the preparation of the infusion solutions used in the clinical study.

1 g Ronopterin ad 10 g sodium hydroxide/sodium hydrogen phosphate solution buffer with a final pH of 7.4 as described in U.S. Pat. No. 10,016,431 or WO 2015/150294 was selected to be aseptically processed, sterilised by membrane filtration and filled into 50 mL glass vials. Subsequently, this solution was freeze-dried according to a selected lyophilisation program that produced a lyophilised product with excellent stability. In this solid composition, Ronopterin is present as free base 4-Amino-5,6,7,8-tetrahydro-L-biopterin. The vials are closed under nitrogen, sealed with freeze-drying stoppers and closed with white vacuum closures. The excipients are added in order to provide an isotonic solution with physiological pH after reconstitution with 50 mL water ad inject. The pH of the final isotonic solution is 6.5 to 7.6. The final concentration of the drug substance VAS203 (Ronopterin) is 20 mg/mL.

Example 3: Phase III Clinical Trial

A phase III trial of Ronopterin infusion to adult TBI patients (18-60 years) with acute moderate and severe TBI was performed. Based on the results of the earlier phase II study, the NOSTRA (NO Synthase in TRAumatic Brain Injury) phase III trial was designed to detect clinically relevant differences in clinical outcome (Extended Glasgow Outcome Score at 6 months after injury) as primary endpoint.

Methods/Design

Trial Design and Participants

NOSTRA III was a multicentre, prospective, two parallel groups, blinded, placebo-controlled, randomised phase III trial of Ronopterin infusion for 48 hours in adult intensive care patients with acute moderate and severe TBI. The primary objective was to demonstrate that the extended Glasgow Outcome Score (eGOS) 6 months after injury is improved following administration of Ronopterin compared to placebo. The detailed study protocol is described by Tegtmeier et al. Efficacy of Ronopterin (VAS203) in Patients with Moderate and Severe Traumatic Brain Injury (NOSTRA phase III trial): study protocol of a confirmatory, placebo-controlled, randomised, double blind, multi-centre study. Trials. 2020. A total of 224 evaluable patients with moderate and severe TBI were enrolled in 32 centres in Austria, France, Germany, Spain, and United Kingdom. The trial started on 24 Aug. 2016 with last-patient last-visit on 17 Jun. 2020.

Eligibility

Patients between 18 and 60 years of age with Glasgow Coma Score≥3 requiring intracranial pressure (ICP) monitoring were enrolled. Other inclusion criteria were TBI within the last 18 hours but at least 6 hours after the injury, which were expected to survive more than 24 hours after admission. The upper limit of age was set to 60 years for safety reasons, as in the NOSTRA-II trial in particular elderly patients exhibited renal dysfunction.

Key exclusion criteria were penetrating head injury, concurrent spinal cord injury, bilateral fixed and dilated pupils (>4 mm), renal dysfunction (serum creatinine values>1.2 mg/dL), rhabdomyolysis and decompressive craniectomy planned prior to randomisation.

The inclusion and exclusion criteria were designed to exclude patients with unsurvivable injuries and patients at risk of renal failure. For complete inclusion and exclusion criteria see Tegtmeier et al., Trial 2020, vide supra.

The centres treated the patients according to their established standard of care; all centres were requested to follow the standardised TBI clinical practice according to the current guidelines [Carney].

Randomisation and Blinding

Patients were assigned to receive Ronopterin and placebo in a ratio of 1:1 via a confidential internet-based system with block randomisation. Balance in treatment allocation across the study participants was enhanced through stratification by the age of the included patient (two age groups 18-39 and 40-60 years) per enrolling site.

The trial was conducted as a double blinded trial. Patients, site investigators, site research coordinators, the sponsor, central CT scan assessor and the staff in charge of treating the patients and evaluating the outcome were blinded.

Because the infusion solution of Ronopterin is slightly yellowish, the ready-to-use infusion solution of Ronopterin and placebo (saline) was prepared in an opaque syringe by unblinded staff not involved in the care of trial patients. Depending on the local organisation this was a medical employee from another ward or the central pharmacy.

Trial Interventions

Ronopterin and placebo (0.9% saline) were infused continuously via central venous catheter at a constant rate. A total dose of 17 mg/kg body weight of Ronopterin was infused for 48 hours (daily dose 8.5 mg/kg body weight).

The dose for each patient was calculated automatically based on the individual body weight, resulting in an individual infusion rate for each patient.

Sample Size Estimation

The main primary and secondary analyses followed a modified intention-to-treat approach to define the full analysis patient set, based on all randomly assigned patients except those withdrawing consent for use of all trial data and those not fulfilling inclusion criteria and never receiving the intervention.

Study Objectives and Endpoints

The primary outcome was the difference between eGOS in Ronopterin and placebo treated patients at 6 months after trauma. The eGOS was determined by a face to face meeting by trained assessors.

The prognostic factor according to Steyerberg et al. (Steyerberg et al. Predicting outcome after traumatic brain injury. PLoS Med 2008 5(8)) predicts the probability of 6 months mortality or probability of 6 months unfavorable outcome. The prognostic factor was analyzed by a t-test on a two-sided alpha level of 0.05. The mean difference of the score under Ronopterin and Placebo with its 95%-confidence interval were summarized for comparability at baseline.

Statistical Analysis

Based on the results of the NOSTRA II trial, sample size estimation of the current NOSTRA Phase III study was based on an assumed odds ratio of 2.3.

The NOSTRA phase III trial was designed to detect a treatment effect as statistically significant on an alpha level of 0.05 with a statistical power of 92%, 220 evaluable patients were needed for the full analysis set. To account for patients lost for follow up and withdrawals, number of recruited patients was increased by 5% to 232 patients. However, as number of withdrawals and lost-to-follow up was very low, the study was successfully completed after recruitment of evaluable 224 patients.

The null-hypothesis of no shift across the 8 ordered categories of eGOS for the two treatment groups was tested after six months based on a proportional odds model stratified by age (18-39 years and 40-60 years). The treatment effect was estimated using ordinal Logistic regression model as the (proportional) odds ratio of Ronopterin versus Placebo. Treatment and age (18-39 years and 40-60 years) were included in the model. The proportional odds assumption was tested using a Chi-Square Score Test.

As secondary efficacy endpoint the eGOS at 3 months was analysed using the same statistics.

Data Monitoring and Interim Analyses

An independent Data and Safety Monitoring Committee (DMC) reviewed the safety data on an on-going basis. Three safety interim analyses were scheduled after inclusion of 40, 80, and 110 patients, respectively. After enrolment of 110 FAS-evaluable patients an unblinded interim analysis was conducted. The result of this interim analysis was the recommendation to continue and finalize the study as planned, Safety and Adverse Event Analyses Safety analyses was performed using standard descriptive methods.

The total number of treatment-emergent adverse events (TEAE) and the total number of patients with TEAEs, the total number of TEAEs related to the study drug (certain, probable, possible), the total number of patients with TEAEs related to the study drug, the total number of TEAEs and the total number of patients with serious TEAEs, the total number of patients with TEAEs leading to discontinuation of study treatment and the total number of patients with TEAEs leading to death were summarised by treatment arm.

Ethical Approval

This trial was conducted in patients unable to consent with patient's legal representatives providing consent for the patient according to local regulations. All patients who recovered were asked to re-consent. Approval for this protocol was obtained from competent regulatory authorities and ethics committees according to local regulations.

Description of the Post Hoc Analysis

The main objective of the post hoc analyses was to estimate the effect size of VAS203 compared with placebo for the primary endpoint eGOS-I in the subgroups time to infusion $\leq 12$ hours and $>12$ hours. Supportive analyses were conducted by age group (<40 years, $\geq$40 years) because age group was used as a stratification factor in the study. Comparability between treatment groups regarding demographics as well as severity and location of disease was investigated using similar methods as in the main CSR.

The proportions of patients per eGOS-I level at 3 months and at 6 months were calculated. For the change in eGOS-I over time, the proportion of patients with changes from 3 to 6 months were calculated by eGOS-I level, and in addition categorised as decreased (i.e. any decrease in eGOS-I level from 3 to 6 months), unchanged (i.e. no change in eGOS-I level from 3 to 6 months), and increased (i.e. any increase in eGOS-I level from 3 to 6 months).

Ordinal logistic regression was used for the analysis of eGOS-I at 3 months and at 6 months, including treatment group and age group (<40 years, $\geq$40 years) as factors in the model. Estimated odds ratios for the comparison of the VAS203 and placebo groups of >1 mean that eGOS-I was higher in the VAS203 group than in the placebo group across the 8 levels, whereas odds ratios of <1 mean that eGOS-I was lower in the VAS203 group than in the placebo group. Odds ratios together with their 95% CIs were used to estimate and assess the size of the treatment effect of VAS203 compared to placebo. Proportional hazards were assumed as valid for all these analyses because ordinal logistic regression analysis is known to be robust against deviations from this assumption; also, the power of assumption checking would be low for small subgroups.

The binary variable eGOS-I increase was defined as "yes" if there was an increase of at least 1 level from 3 to 6 months. If there was no change or a decrease of at least 1 level from 3 to 6 months, the variable was defined as "no". For the analysis of eGOS-I increase, nominal logistic regression was used, including treatment group and age group (<40 years, $\geq$40 years) as factors and eGOS-I at 3 months as covariate to adjust for potential differences at 3 months. Obtained odds ratios for the comparison of the VAS203 and placebo groups of >1 mean that the eGOS-I increase occurred more often in the VAS203 group than in the placebo group, whereas odds ratios of <1 mean that the eGOS-I increase occurred less often in the VAS203 group than in the placebo group.

The analyses were done for all patients in the full analysis set (FAS) and for the subgroups defined by time to infusion (≤12 h, >12 h) and age group (<40 years, ≥40 years).

The analyses were based on ADaM datasets produced for the main CSR in 2020. For the eGOS-I dataset, 4 missing values for time to infusion were imputed in collaboration with the Sponsor based on calculation from related variables. Four eGOS-I values were missing at 3 months; the respective patients were excluded from analyses of this variable.

A corrected value for time to admission to study centre (for 1 patient, the date for admission to study centre had been incorrectly captured in the CRF). This value was changed via hard coding following authorisation of a post-lock database change by the Sponsor.

Consistent with the rounding applied for the main CSR, the variables "time from injury to admission [hours]" and "time from injury to infusion [hours] were rounded to 1 decimal place (i.e. 6-minute intervals). Sensitivity analyses based on the exact times for both variables yielded consistent results; specifically, patient allocation to the subgroups defined by time to infusion (≤12 h, >12 h) was not affected. Thus, rounding had no impact on the post hoc analyses of eGOS-I.

An interim analysis with possible sample size increase had been planned and conducted for the study; the resulting 2 study stages were not considered in the post hoc analyses. All statistical analyses were done using SAS Version 9.4 (SAS Institute Inc., Cary, NC, USA).

Results
Demographics

Between August 2017 and December 2020, a total of 1940 patients were screened for eligibility. Of these patients, 228 were randomized and assigned to receive Ronopterin (115) or placebo (113). Major reasons for exclusion were age of the patients, no informed consent and early allocation to craniectomy. Four randomized patients did not receive treatment because of withdrawal of consent and because the IMP could not be prepared in time. In total, 224 (98.2%) patients received treatment and were considered part of the Safety Analysis Set. One patient was lost to follow-up. Thus, 223 (97.8%) patients were part of the Full Analysis Set and 208 (91.2%) patients were considered part of the Per Protocol Set.

The majority of patients were male (180 [80.4%] patients) and caucasian (211 [94.2%] patients). The mean age was 39.3 years (SD+/−13.2) the mean body mass index was 25.5 kg/m$^2$ (SD+/−3.9).

The demographic parameters (age, body weight) and baseline characteristics (injury severity, prognostic factor, time from injury to randomisation) were well balanced between the two treatment arms, indicating the populations were comparable at baseline.

Efficacy Results:

No difference was seen between the Ronopterin and placebo groups for overall eGOS-I rating at 6 months (using the ordinal logistic regression inverse-normal approach) and, therefore, the primary efficacy endpoint was not met.

A difference was seen when comparing age groups in the entire patient population independent of treatment (age≥40 group vs. age<40 group) with an odds ratio of 0.270 (95% CI: 0.134, 0.547; p<0.001), indicating a difference in recovery in favour of patients aged <40 years of age.

Patient overall eGOS-I rating at 6 months was controlled for country and centre, country, age and additional covariates. Differences between Ronopterin and placebo were seen in some centres, however, caution must be taken when interpreting the results, due to the low patient numbers in each centre. No difference was seen when controlling by country, however, a marginal effect in favour of Ronopterin was seen for France (odds-ratio: 3.640 [95% CI: 0.979, 13.535]; p=0.054). No difference was seen when controlling for age as a continuous variable.

Based on the time-dependent activation of pathologic cascades during the early phase after TBI and the benefits observed with an infusion of VAS203 during the initial 12 hours after TBI in the Phase IIa trial [Stover], a post-hoc-analysis was performed to determine whether patients in whom VAS203 was infused ≤12 hours after TBI, show better clinical improvement compared to patients in whom infusion was started >12 hours after TBI.

In patients with time to infusion ≤12 hours, eGOS was higher by 1 eGOS level in the Ronopterin compared to placebo treated patients (median 6 vs 5; ns); in patients with time to infusion >12 hours, eGOS was similar in both treatment groups at 6 months (median 5 vs 5).

In patients with time to infusion ≤12 hours, the proportion of patients with Good Recovery (eGOS 7 and 8) was higher in the Ronopterin compared to placebo treated patients (37 vs 23%; ns; NNT=8). In the Ronopterin-treated group the proportion of patients with a Good Recovery at 6 months was increased by 61% compared to the Placebo group. In patients with time to infusion >12 hours, the proportion of patients with Good Recovery was similar in both treatment groups at 6 months (25 vs 28%).

Figure 4B:
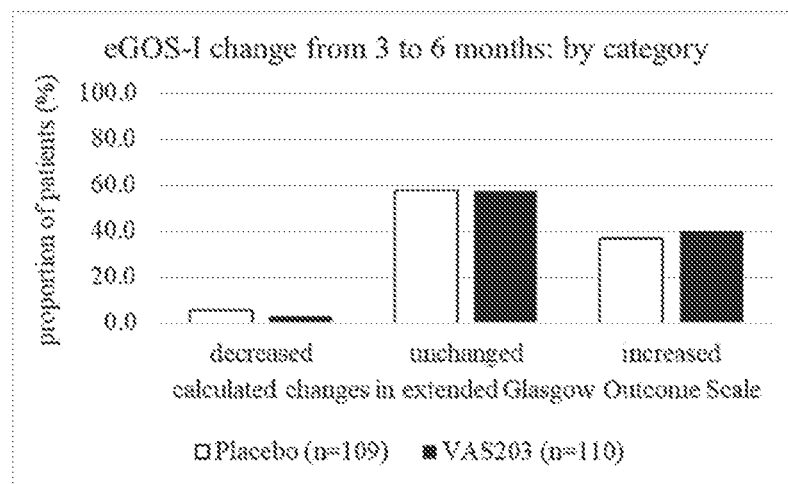
Figures 4C, 4D:
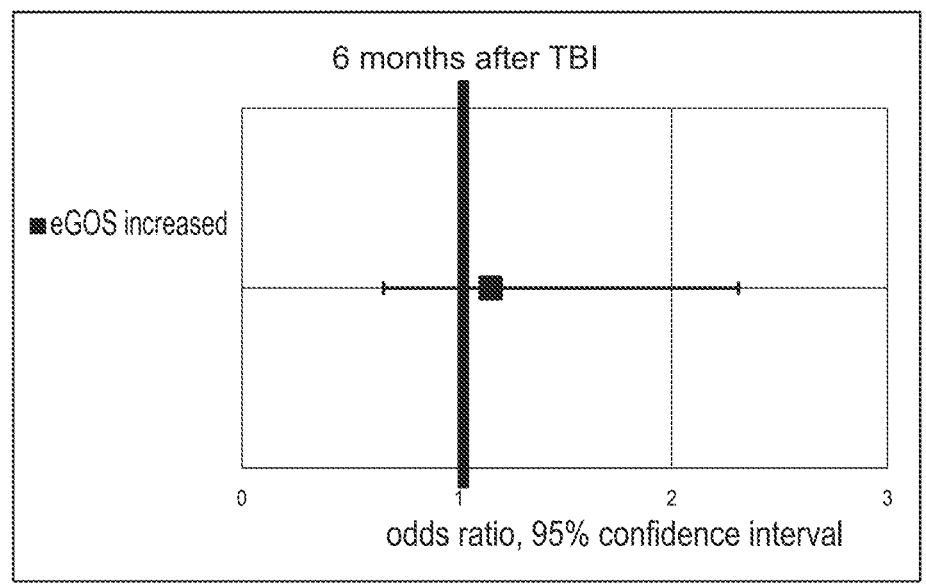

In more detail, and with reference to FIGS. 4A-D to FIGS. 18A-D the results of this present study are as follows:

FIGS. 4A-D show the distribution of proportion of patients between Placebo and Ronopterin (VAS203)-treated patients reflecting changes in eGOS from 3 to 6 months for all patients and all times to infusion. FIG. 4A shows the change in eGOS from 3 to 6 months by eGOS level, FIG. 4B shows the change in eGOS from 3 to 6 months by category, FIG. 4C shows the increase of eGOS level by number of patients and FIG. 4D shows the odds-ratio for the eGOS increase. As seen from FIG. 4A Ronopterin-treated patients show an increase in eGOS levels up to 4 levels and the overall increase in eGOS by at least 2 levels is encountered more often in Ronopterin-treated patients (24 vs. 13 for the Ronopterin group, FIG. 4C). FIGS. 4A-D show for the Ronopterin-treated group more patients with higher increase in eGOS over time, however the increase is not (statistically) significant (FIG. 4D). In addition, FIG. 4A-D show for the Ronopterin-treated group that there are less patients with a decrease in eGOS over time, however this decrease is not (statistically) significant.

FIGS. 5A-H show the distribution of proportion of patients of all ages between Placebo and Ronopterin-treated patients with changes in eGOS from 3 to 6 months, depending on the time to infusion within 12 hours and after 12 hours after traumatic brain injury. FIGS. 5A-H shows for the Ronopterin-treated group a significant increase in proportion of patients with increased eGOS.

Figure 5A:
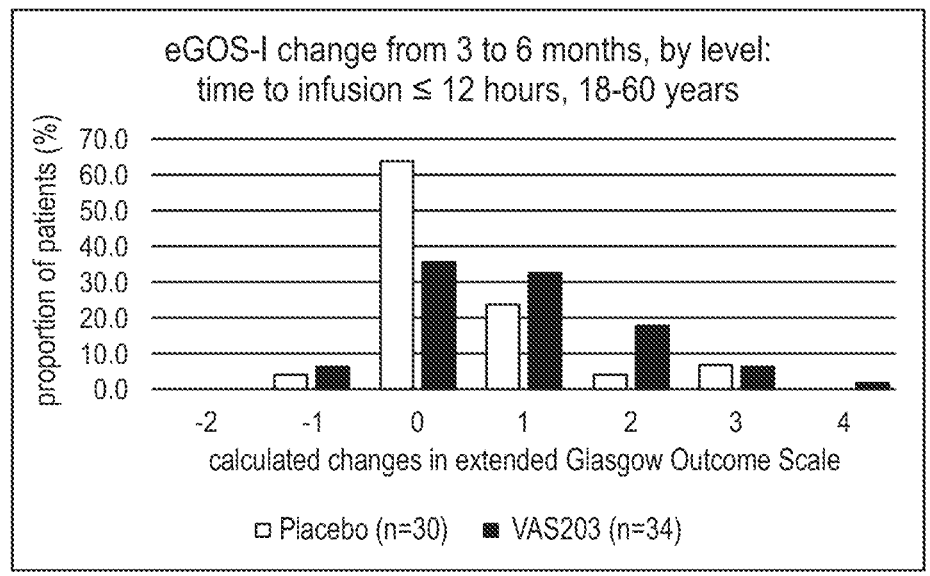
FIGS. 5A-H show the distribution of proportion of patients of all ages between Placebo and Ronopterin-treated patients with changes in eGOS from 3 to 6 months, depending on the time to infusion within 12 hours and after 12 hours after traumatic brain injury.
Figure 5B:
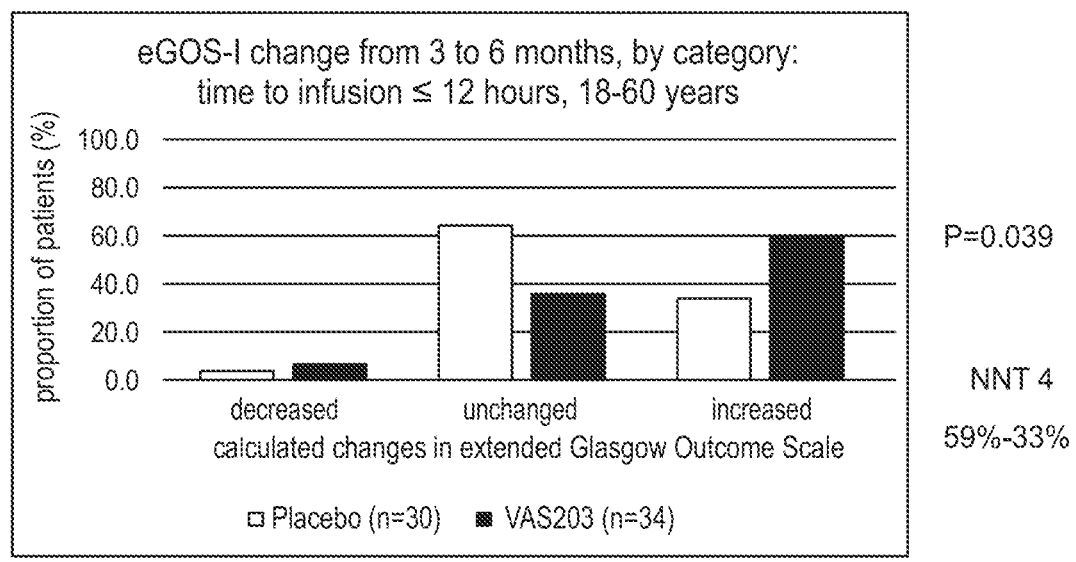
Figures 5C, 5D:
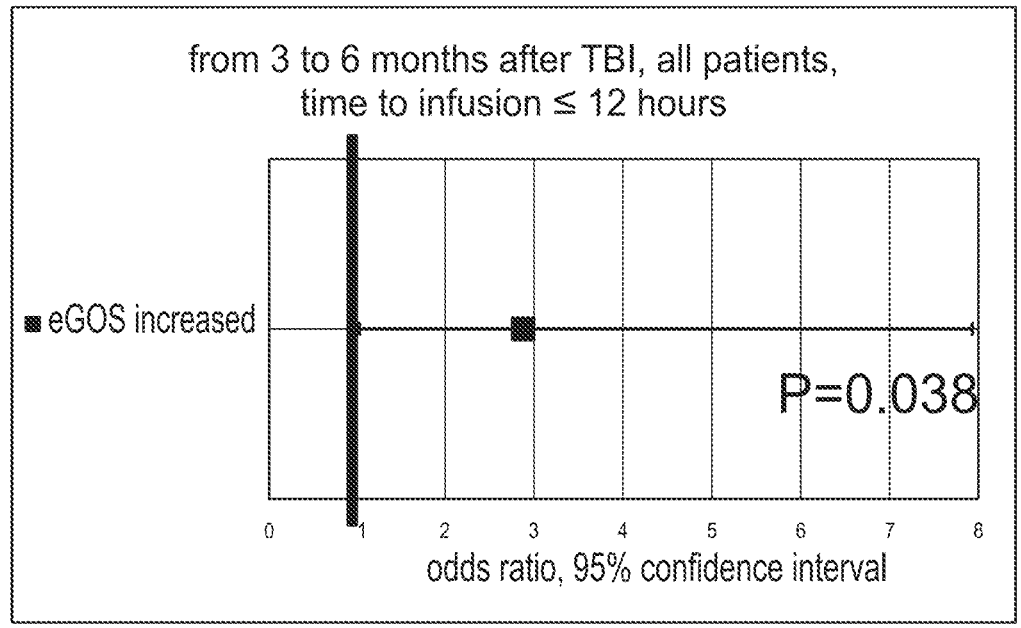
Figure 5E:
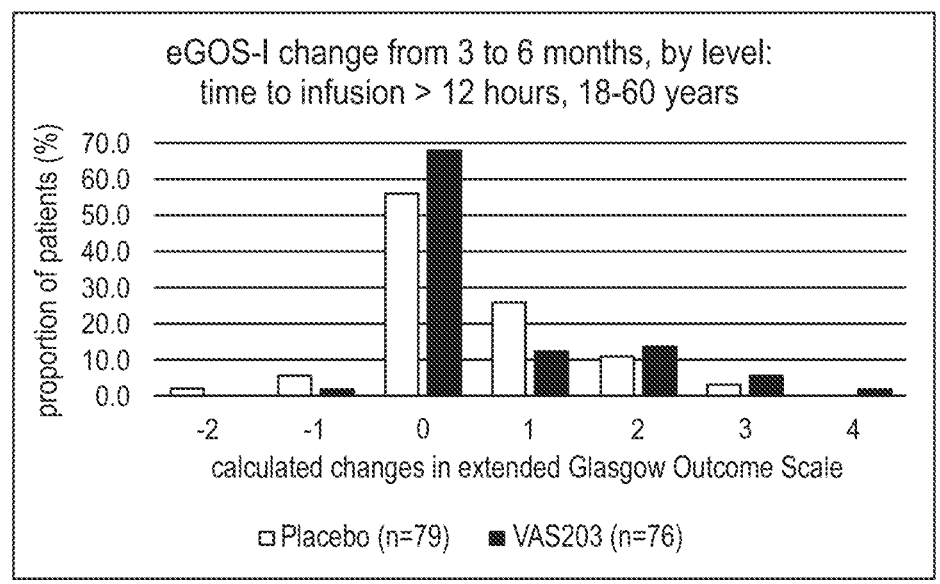
Figure 5F:
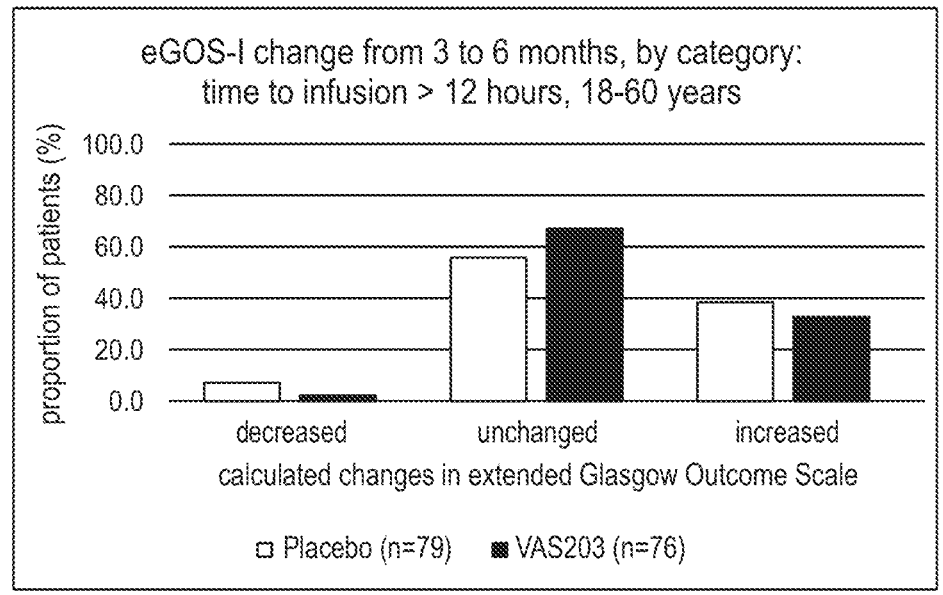
Figures 5G, 5H:
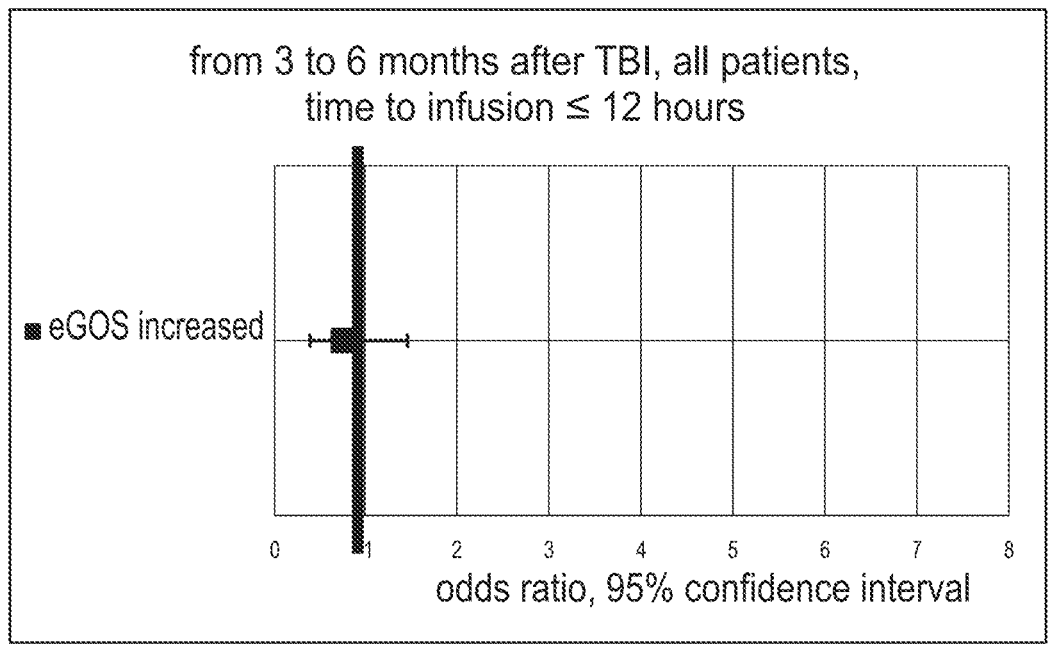

In more detail FIGS. 5A to 5D show the results for early infusion (≤12 hours), with FIG. 5A showing the change in eGOS from 3 to 6 months by eGOS level, FIG. 5B showing the change in eGOS from 3 to 6 months by category, FIG. 5C showing the increase of eGOS level by number of patients and FIG. 5D showing the odds-ratio for the eGOS increase. FIGS. 5A to 5D show that for early infusion (≤12 hours) Ronopterin-treated patients show an increase in eGOS levels up to 4 levels (FIG. 5A). FIG. 5C shows that overall, an increase in eGOS by at least 2 levels is encountered more often in Ronopterin-treated patients compared to placed (9 vs 3). The increase in proportion of patients with an increase by at least 1 level is significant compared to Placebo-treated patients. FIGS. 5E to 5H show the results for late infusion (>12 hours), with FIG. 5E showing the change in eGOS from 3 to 6 months by eGOS level, FIG. 5F showing the change in eGOS from 3 to 6 months by category, FIG. 5G showing the increase of eGOS level by number of patients and FIG. 5H showing the odds-ratio for the eGOS increase. Ronopterin-treated patients show an increase in eGOS levels up to 4 levels (FIG. 5E). Overall, increase in eGOS by at least 2 levels is encountered more often in Ronopterin-treated patients (15 vs 10), see FIG. 5G.

Figure 6A:
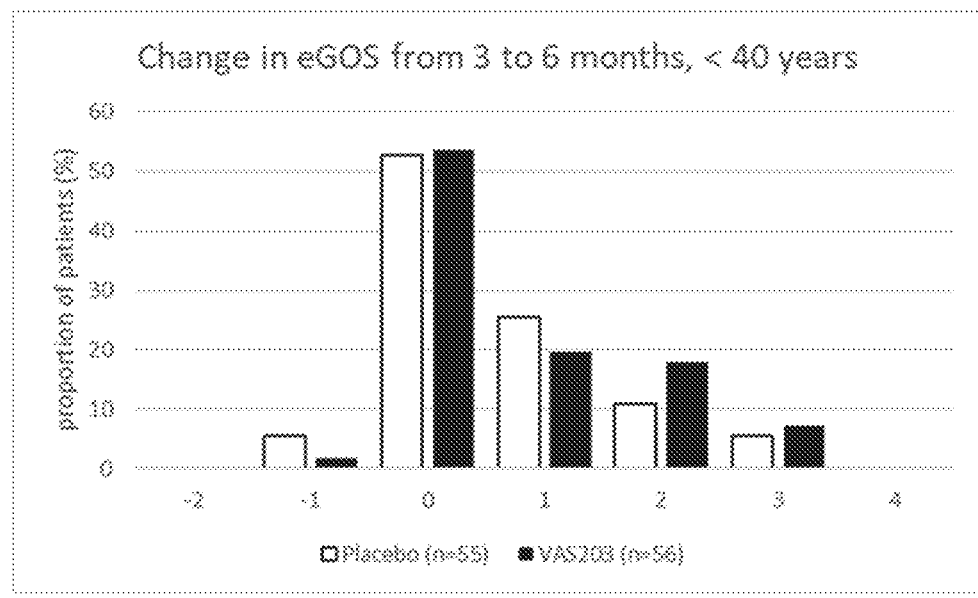
FIGS. 6A-D show the change in eGOS levels from 3 to 6 months, for patients with an age of 18-39 years and at all times to infusion.
Figure 6B:
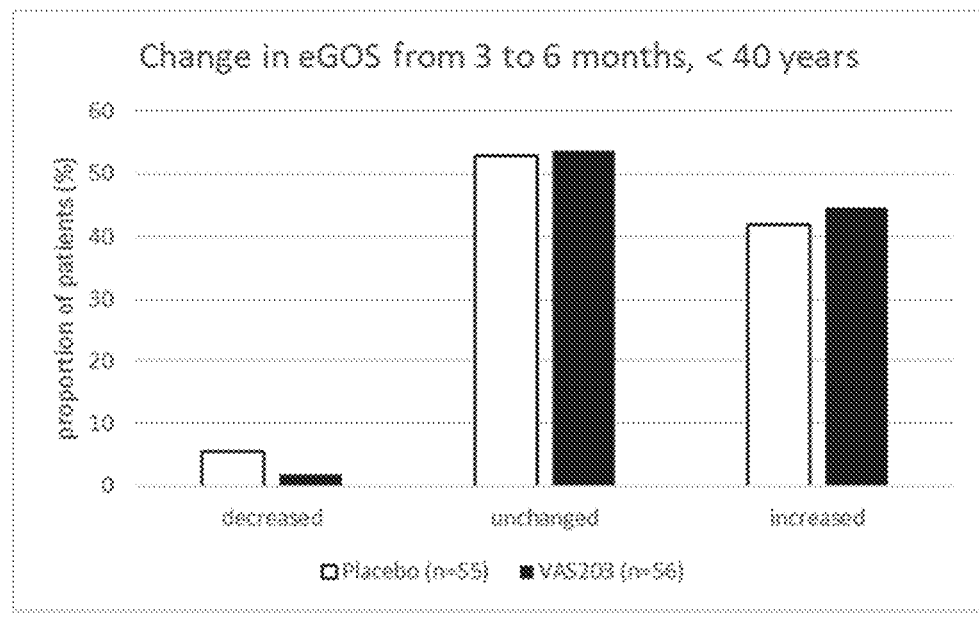
Figures 6C, 6D:
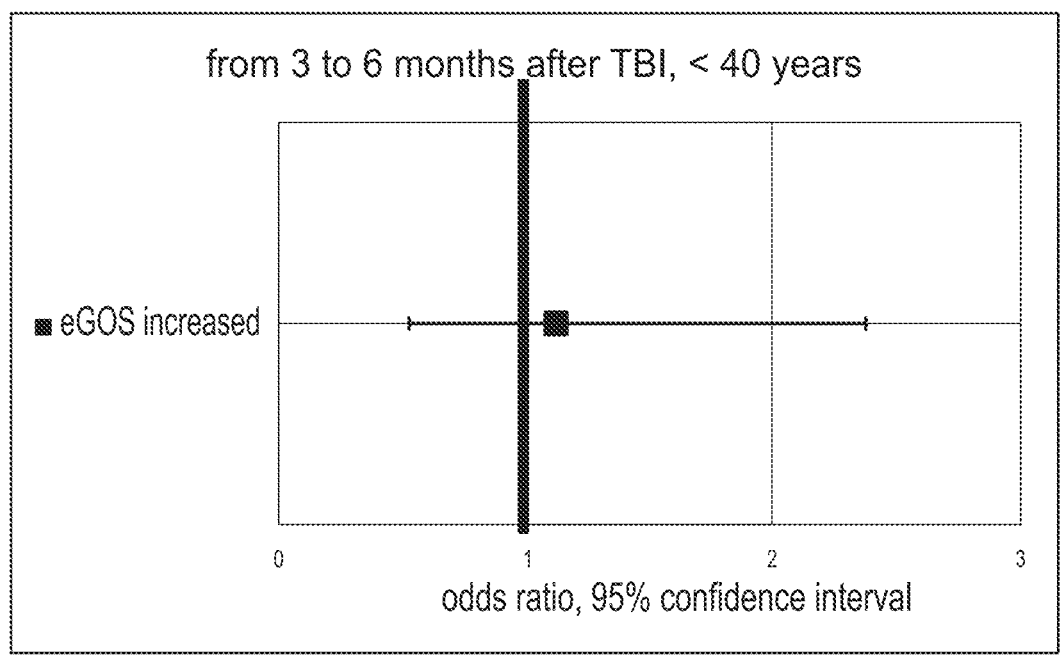

FIGS. 6A-D show the change in eGOS levels from 3 to 6 months, for patients with an age of 18-39 years and at all times to infusion. FIG. 6A shows the change in eGOS from 3 to 6 months by eGOS level, FIG. 6B shows the change in eGOS from 3 to 6 months by category, FIG. 6C shows the increase of eGOS level by number of patients and FIG. 6D shows the odds-ratio for the eGOS increase. Distribution of proportion of patients between Placebo and Ronopterin-treated patients with changes in eGOS from 3 to 6 months for patients aged 18-39 years. Ronopterin-treated patients show an increase in eGOS levels up to 3 levels (FIG. 6A). Overall, increase in eGOS by at least 2 levels is encountered more often in Ronopterin-treated patients (14 vs 9), see FIG. 6C. FIGS. 6A-D shows that in the Ronopterin-treated group, there are more patients with higher increase in eGOS over time, however this increase is not significant (see FIG. 6D) while in the Ronopterin-treated group, there are less patients with decrease in eGOS over time, however this decrease is not significant.

Figure 7A:
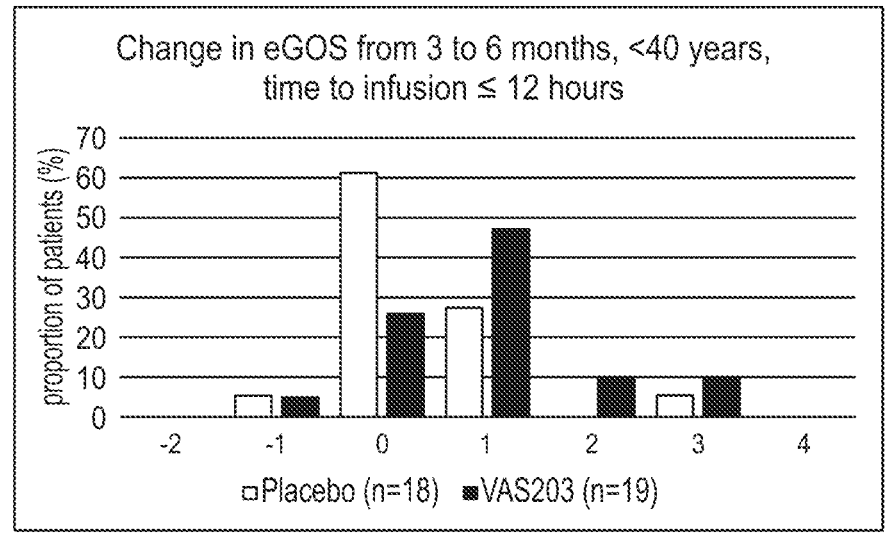
FIGS. 7A-H show the distribution of proportion of patients between Placebo and Ronopterin-treated patients with changes in eGOS from 3 to 6 months for patients aged 18-39 years, depending on the time to infusion within 12 hours and after 12 hours after traumatic brain injury. In more detail.
Figure 7B:
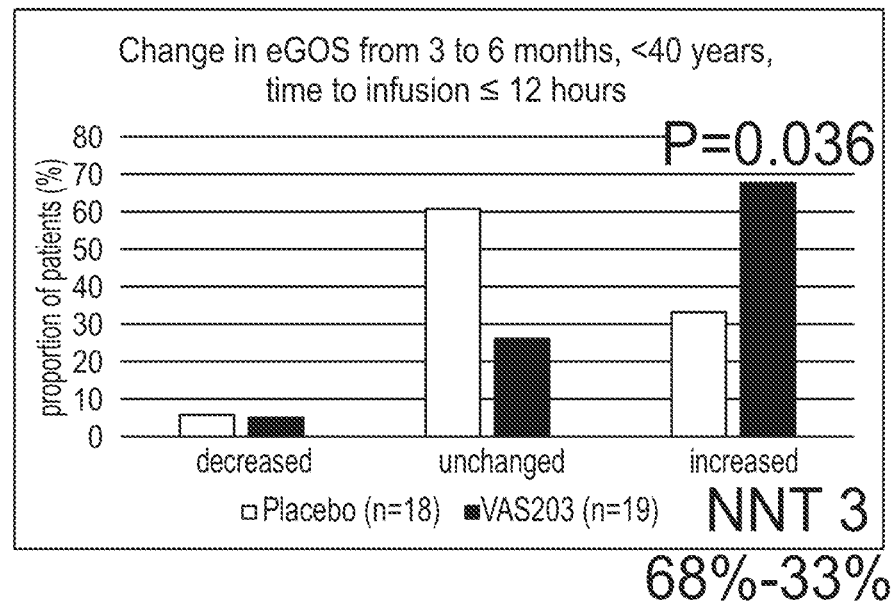
Figures 7C, 7D:
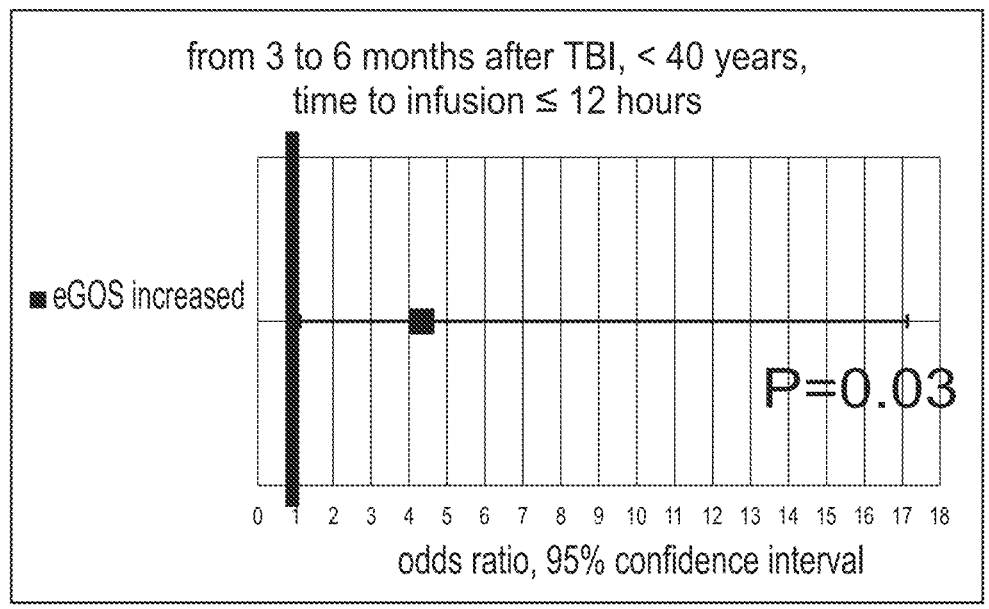
Figure 7E:
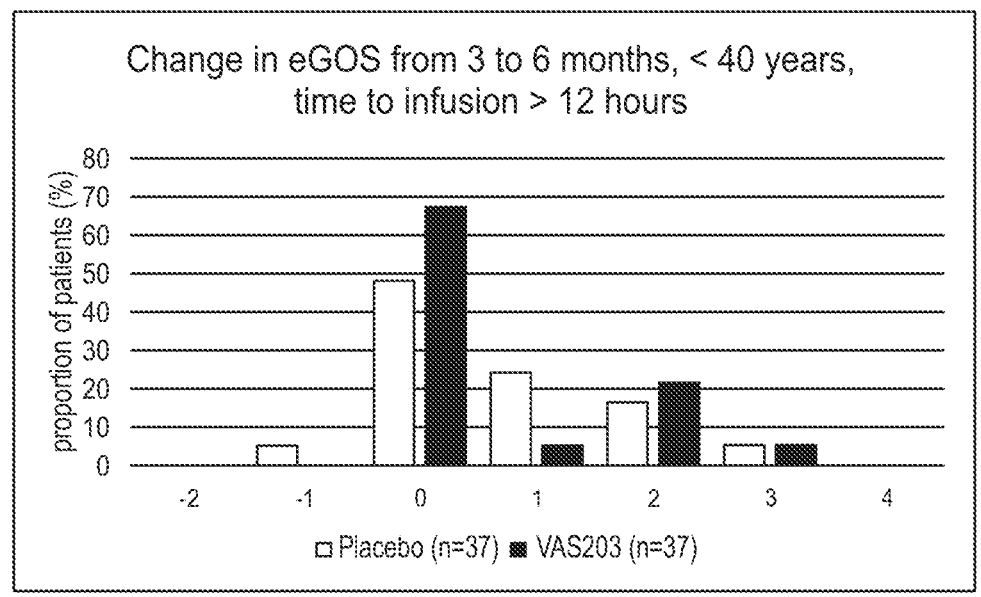
Figure 7F:
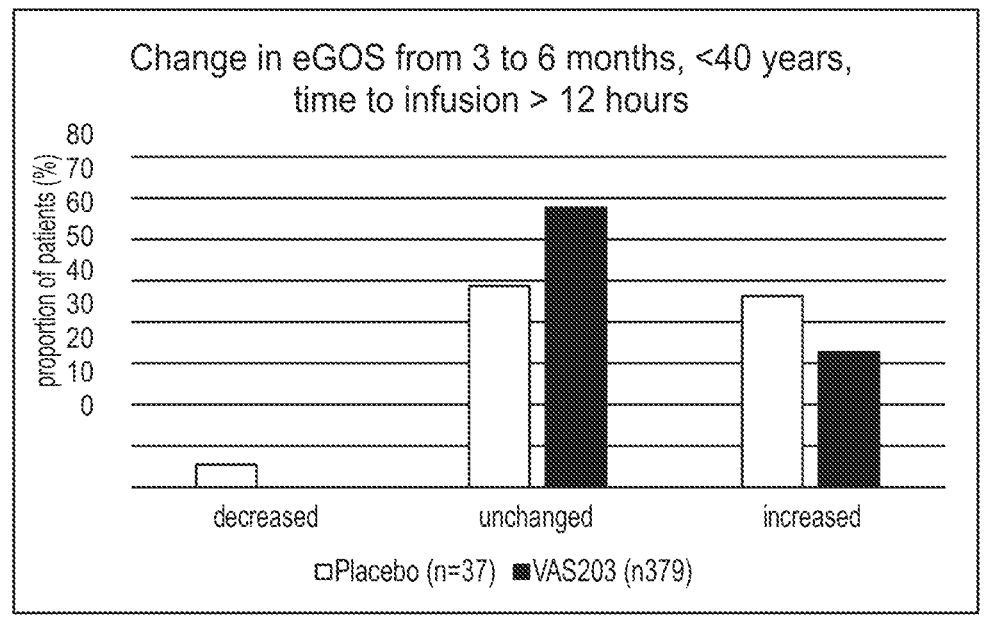
Figures 7G, 7H:
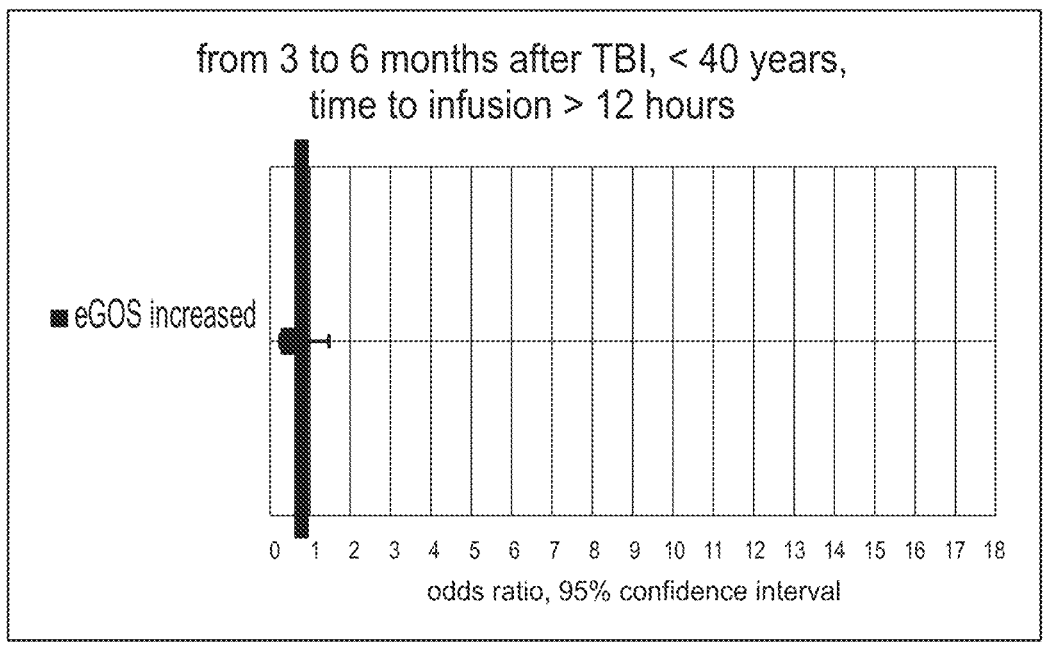

FIGS. 7A-H show the distribution of proportion of patients between Placebo and Ronopterin-treated patients with changes in eGOS from 3 to 6 months for patients aged 18-39 years, depending on the time to infusion within 12 hours and after 12 hours after traumatic brain injury. In more detail FIGS. 7A to 7D show the results for early infusion (≤12 hours), with FIG. 7A showing the change in eGOS from 3 to 6 months by eGOS level, FIG. 7B showing the change in eGOS from 3 to 6 months by category, FIG. 7C showing the increase of eGOS level by number of patients and FIG. 7D showing the odds-ratio for the eGOS increase. FIGS. 7A to 7D show that for early infusion (≤12 hours) Ronopterin-treated patients show an increase in eGOS levels up to 3 levels (FIG. 7A). FIG. 7C shows that overall, an increase in eGOS by at least 2 levels is encountered more often in Ronopterin-treated patients compared to placed (4 vs 1). The increase in proportion of patients with an increase by at least 1 level is significant compared to Placebo-treated patients, see FIG. 7B and FIG. 7D. FIGS. 7E to 7H show the results for late infusion (>12 hours), with FIG. 7E showing the change in eGOS from 3 to 6 months by eGOS level, FIG. 7F showing the change in eGOS from 3 to 6 months by category, FIG. 7G showing the increase of eGOS level by number of patients and FIG. 7H showing the odds-ratio for the eGOS increase. Ronopterin-treated patients show an increase in eGOS levels up to 3 levels (FIG. 7E). Overall, increase in eGOS by at least 2 levels is encountered more often in Ronopterin-treated patients (10 vs 8), see FIG. 7G.

Figure 8A:
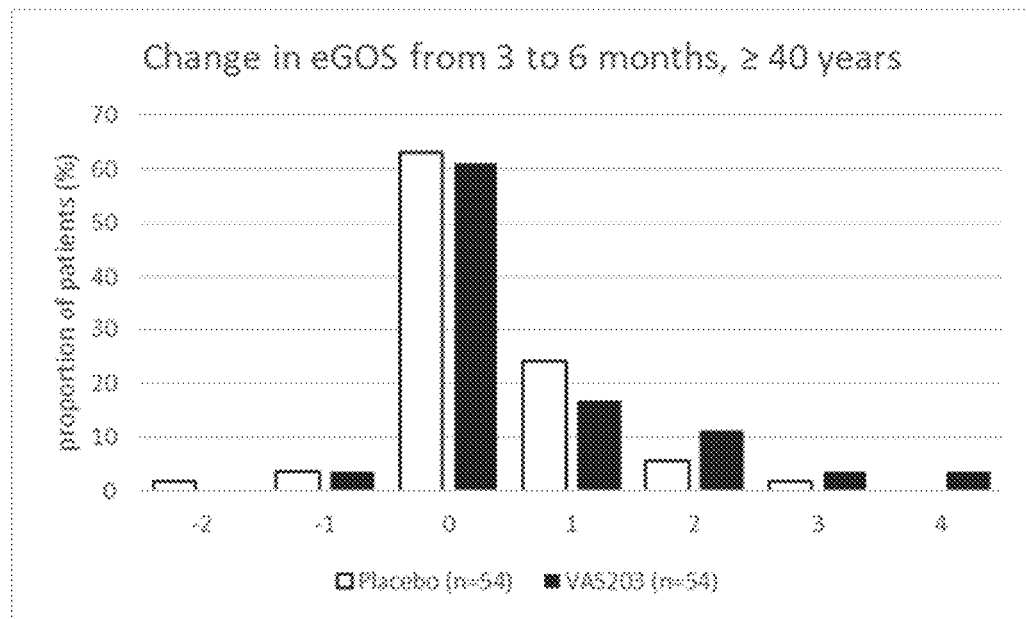
FIGS. 8A-D show the distribution of proportion of patients between Placebo and Ronopterin-treated patients with changes in eGOS from 3 to 6 months for patients aged 40-60 years.
Figure 8B:
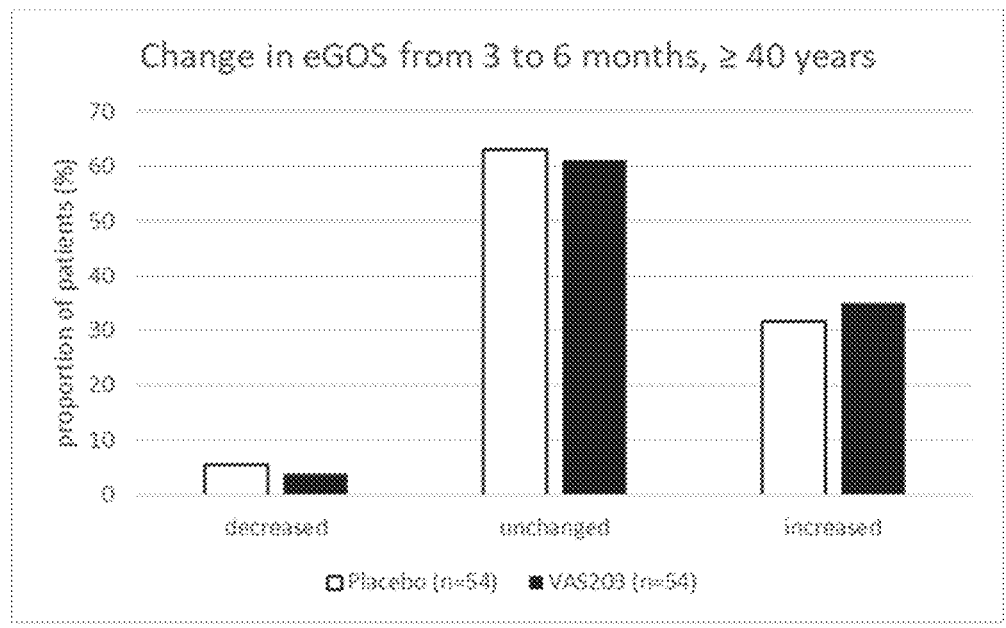
Figures 8C, 8D:
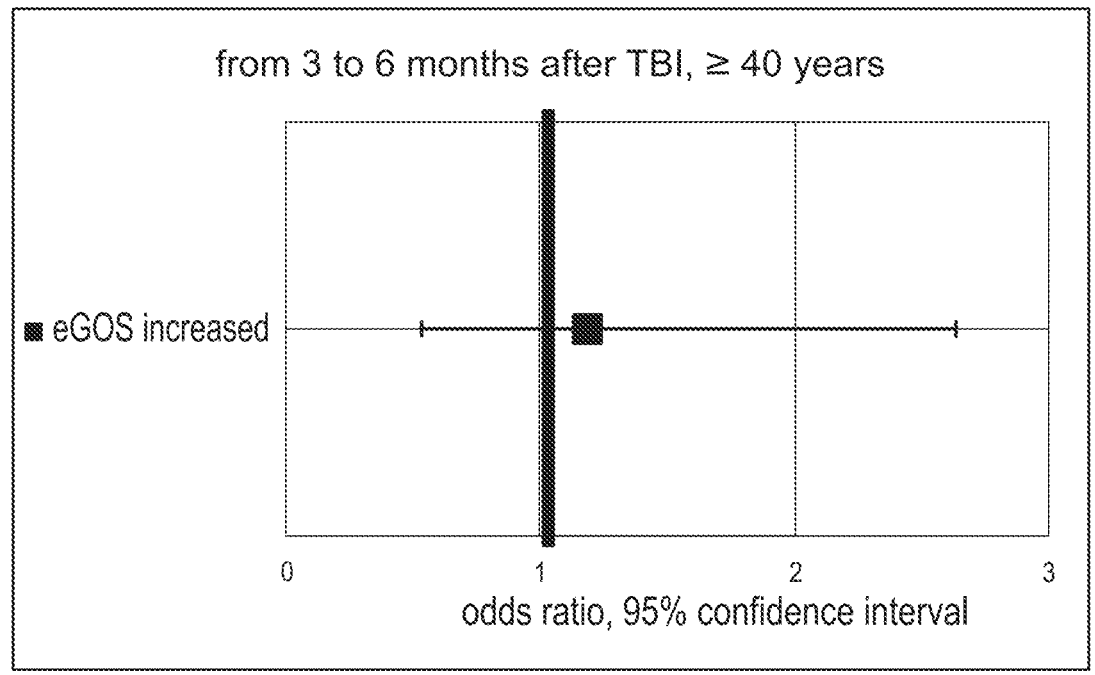

FIGS. 8A-D show the distribution of proportion of patients between Placebo and Ronopterin-treated patients with changes in eGOS from 3 to 6 months for patients aged 40-60 years. FIG. 8A shows the change in eGOS from 3 to 6 months by eGOS level, FIG. 8B shows the change in eGOS from 3 to 6 months by category, FIG. 8C shows the increase of eGOS level by number of patients and FIG. 8D shows the odds-ratio for the eGOS increase. As seen from FIG. 8A Ronopterin-treated patients show an increase in eGOS levels up to 4 levels and the overall increase in eGOS by at least 2 levels is encountered more often in Ronopterin-treated patients (10 vs. 4), see FIG. 8C. FIGS. 8A-D show for the Ronopterin-treated group more patients with higher increase in eGOS over time, however the increase is not (statistically) significant (FIG. 8D). In addition, FIGS. 8A-D show for the Ronopterin-treated group that there are less patients with a decrease in eGOS over time, however this decrease is not (statistically) significant.

Figure 9A:
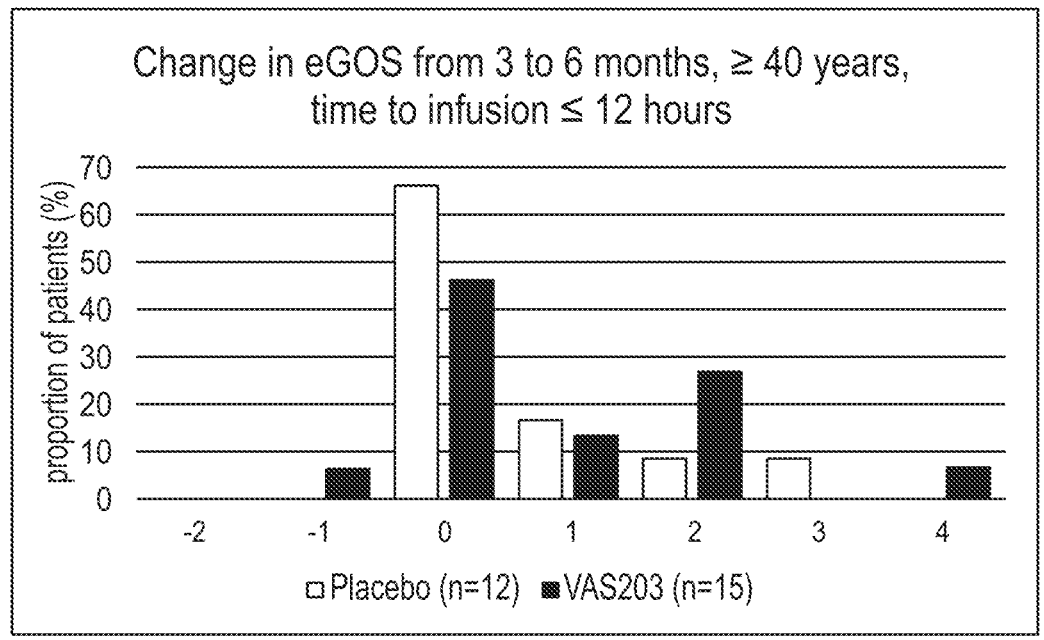
FIGS. 9A-H show the distribution of proportion of patients between Placebo and Ronopterin-treated patients with changes in eGOS from 3 to 6 months for patients aged 40-60 years, depending on the time to infusion within 12 hours and after 12 hours after traumatic brain injury. In more detail.
Figure 9B:
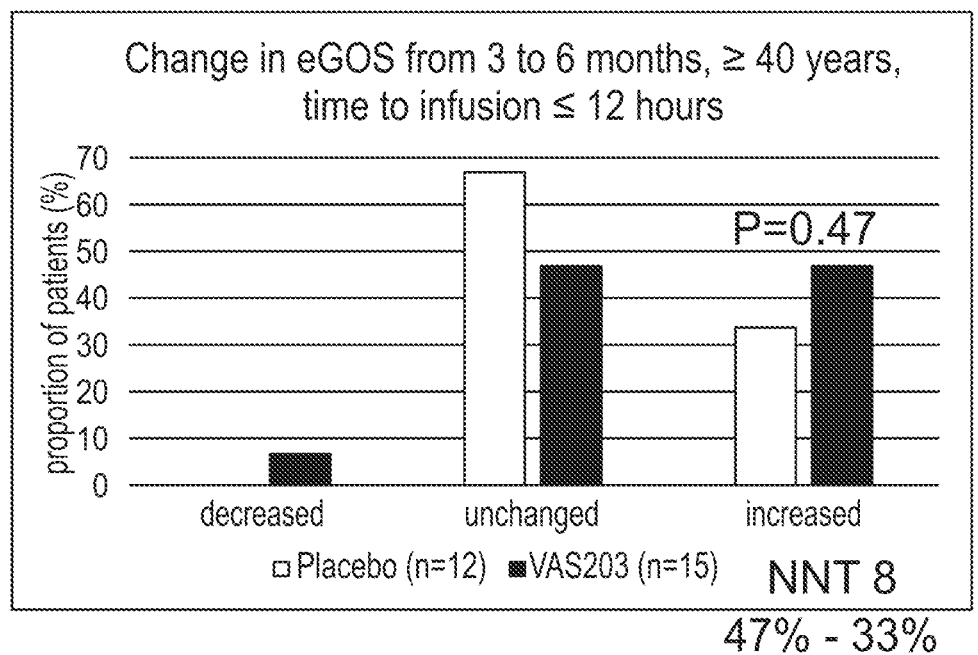
Figures 9C, 9D:
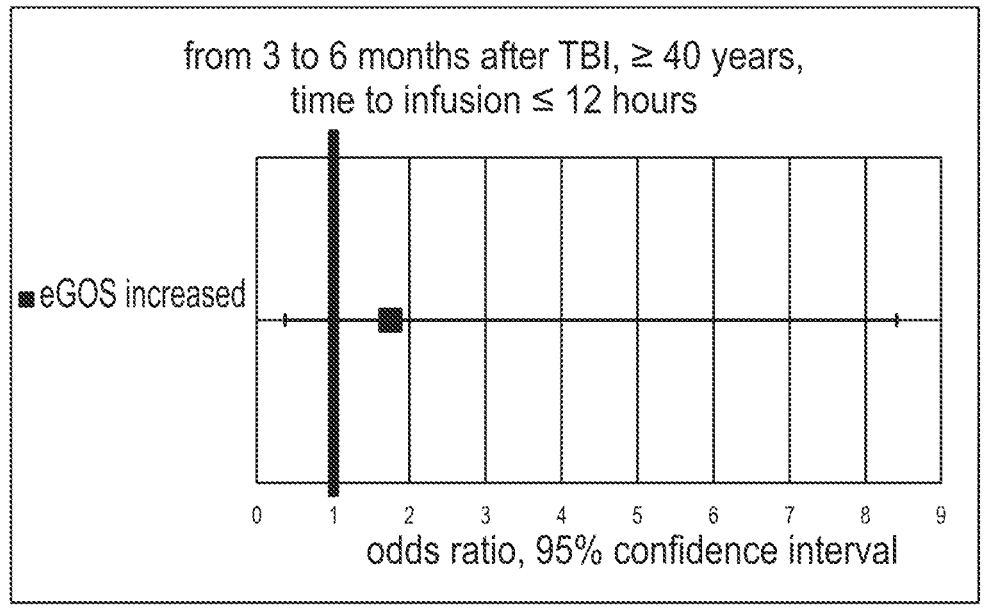
Figure 9E:
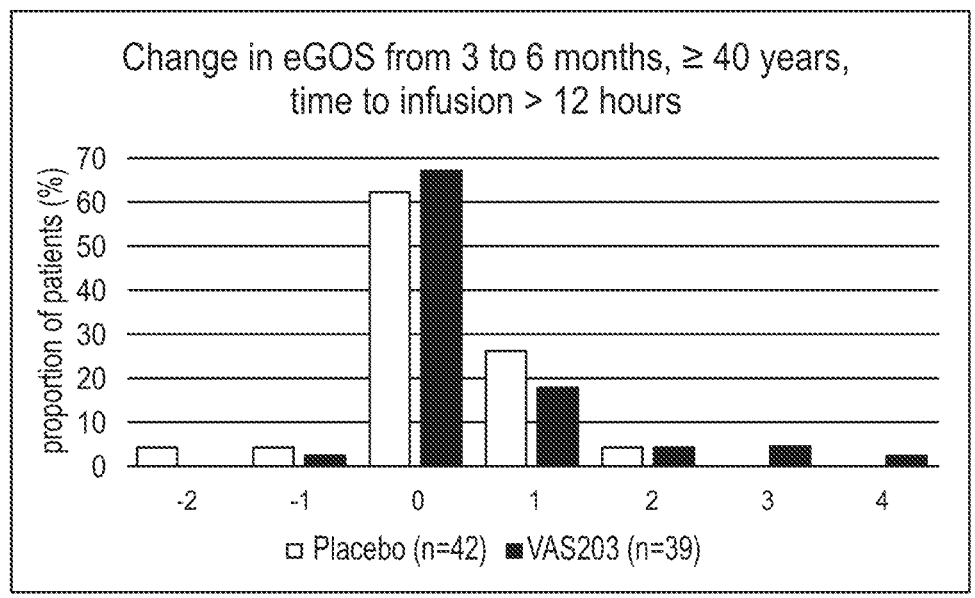
Figure 9F:
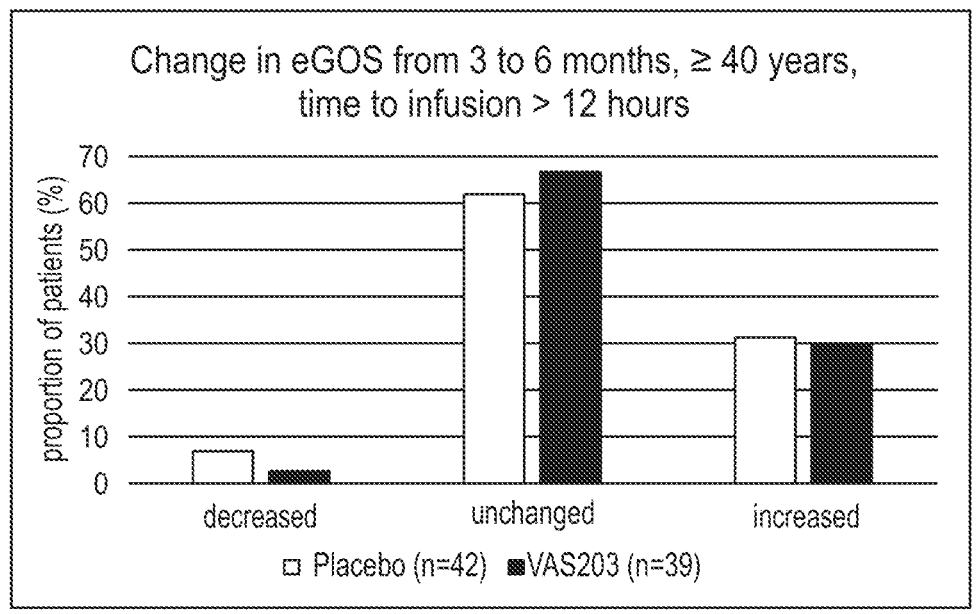
Figures 9G, 9H:
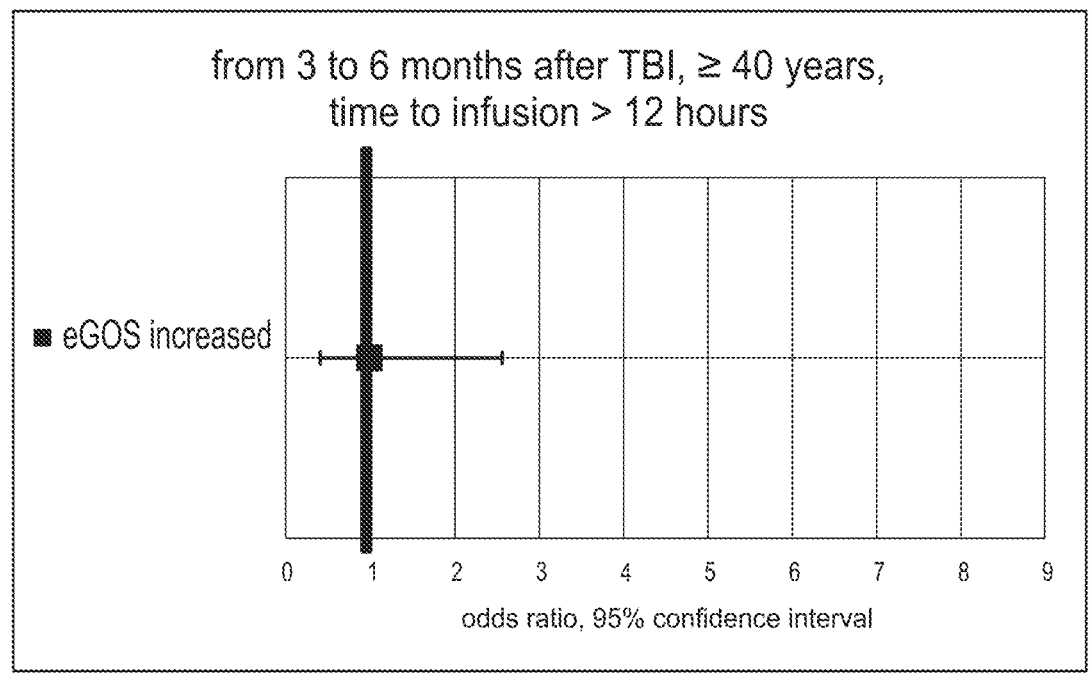

FIGS. 9A-H show the distribution of proportion of patients between Placebo and Ronopterin-treated patients with changes in eGOS from 3 to 6 months for patients aged 40-60 years, depending on the time to infusion within 12 hours and after 12 hours after traumatic brain injury. In more detail FIGS. 9A to 9D show the results for early infusion (≤12 hours) with FIG. 9A showing the change in eGOS from 3 to 6 months by eGOS level, FIG. 9B showing the change in eGOS from 3 to 6 months by category, FIG. 9C showing the increase of eGOS level by number of patients and FIG. 9D showing the odds-ratio for the eGOS increase. As seen from FIG. 9A Ronopterin-treated patients show an increase in eGOS levels up to 4 levels and the overall increase in eGOS by at least 2 levels is encountered more often in Ronopterin-treated patients (5 vs. 2), see FIG. 9C. FIG. 9A to FIG. 9D show for patients with an age≥40 years and administration of Ronopterin ≤12 hours a trend to more patients with an increase in their eGOS levels (eGOS responders). FIGS. 9E to 9H show the results for late infusion (>12 hours), with FIG. 9E showing the change in eGOS from 3 to 6 months by eGOS level, FIG. 9F showing the change in eGOS from 3 to 6 months by category, FIG. 9G showing the increase of eGOS level by number of patients and FIG. 9H showing the odds-ratio for the eGOS increase. Ronopterin-treated patients show an increase in eGOS levels up to 4 levels (FIG. 9E). Overall, increase in eGOS by at least 2 levels is encountered more often in Ronopterin-treated patients (5 vs 2), see FIG. 9G.

Figure 10:
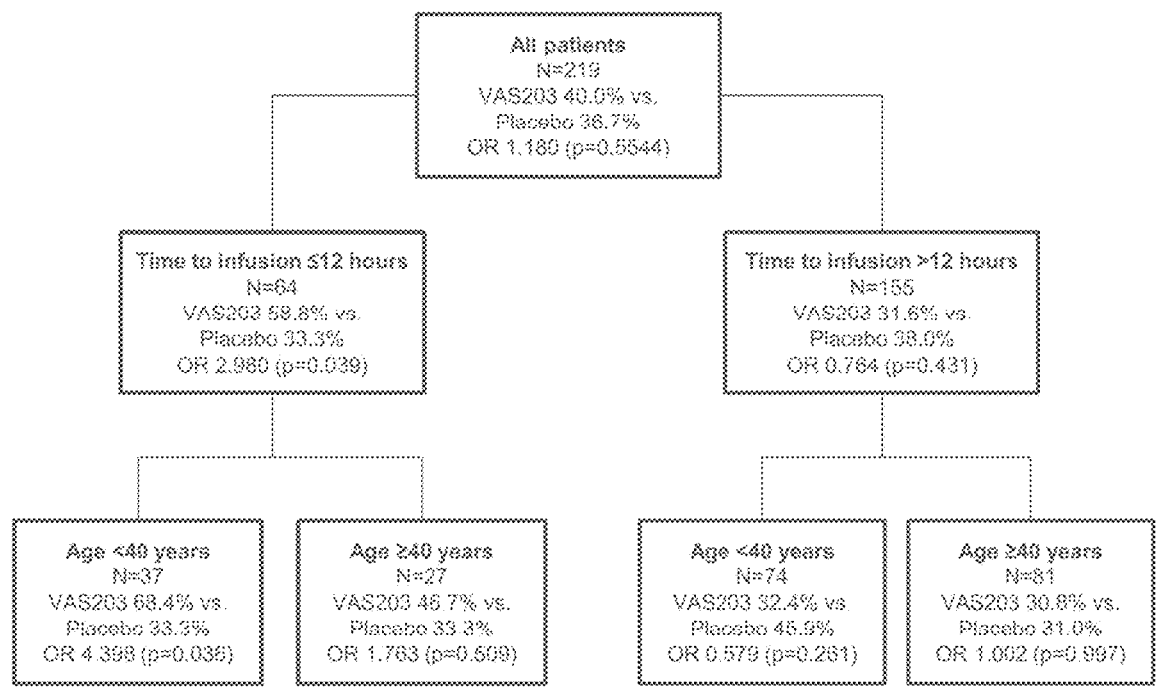
FIG. 10 shows a summary of the Odds Ratios (OR) for increases in eGOS levels from 3 to 6 months for early and late infusion and the age groups 18-39 and 40-60 years (<40 and ≥40 years). Generally speaking, the odds ratio is a measure of the strength of association with an exposure and an outcome. An OR>1 means greater odds of association with the exposure and outcome. An OR=1 means there is no association between exposure and outcome. An OR<1 means there is a lower odds of association between the exposure and outcome. In the present context of comparing two groups such a first group of patients that are being treated with Ronopterin and a second group of patients that are being treated with a placebo, an odds ratio of 1 means that there no difference between the odds in both groups, while an odds ratio of >1 means that the odds of the first group are higher and an odds ratio of <1 means, that the odds of the first group are lower. Generally speaking, an OR>1.8 is clinically relevant, meaning a compound of interest shows the desired therapeutic efficacy. Using here, as an illustrative example, as first group the population of patients in the age groups 18-39 (<40) that receive an early infusion (≤12 hours) of Ronopterin for treatment of TBI and as a second group the population of patients in the age groups 18-39 (<40) that receive an early infusion (≤12 hours) of placebo, the odds ratio is 4.398. This means, the chance of recovering from TBI is about 4.4 times higher for the patient population that is treated with Ronopterin than it is for the patient population that receives placebo.

FIG. 10 shows a summary of the Odds Ratios (OR) for increases in eGOS levels from 3 to 6 months for early and late infusion and the age groups 18-39 and 40-60 years (<40 and ≥40 years). In this context, it is noted that an odds ratio of 1 means that there no difference between the odds in both groups, while an odds ratio of >1 means that the odds of the first group are higher and an odds ratio of <1 means, that the odds of the first group are lower.

Figure 11A:
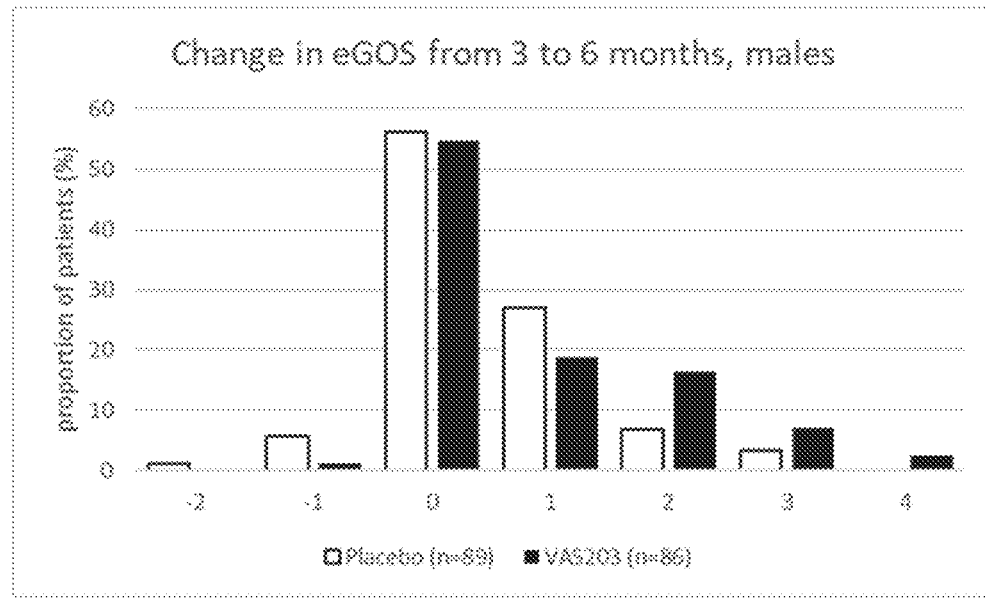
FIGS. 11A-D show the distribution of proportion of patients between Placebo and Ronopterin-treated patients with changes in eGOS from 3 to 6 months for male patients.
Figure 11B:
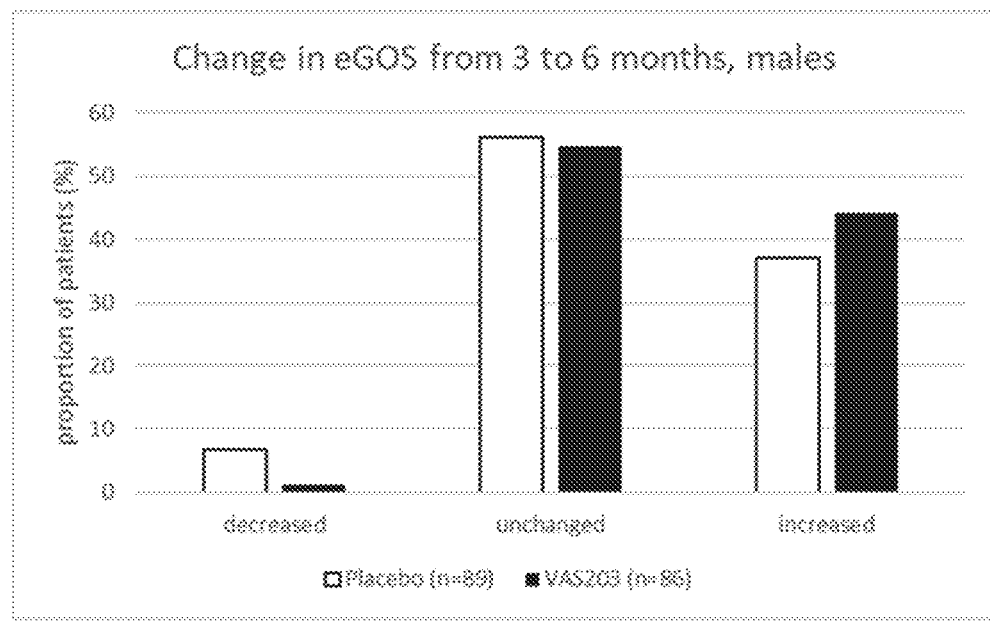
Figures 11C, 11D:
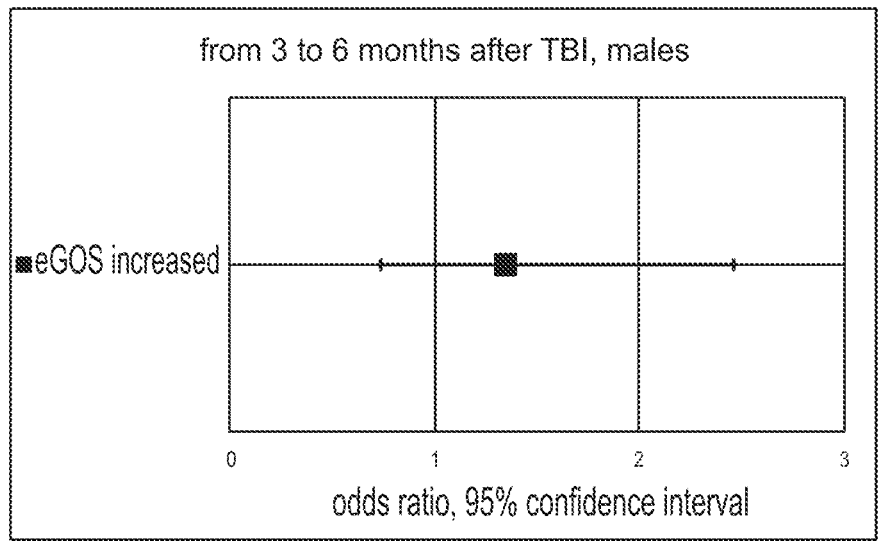

FIGS. 11A-D show the distribution of proportion of patients between Placebo and Ronopterin-treated patients with changes in eGOS from 3 to 6 months for male patients. FIG. 11A shows the change in eGOS from 3 to 6 months by eGOS level, FIG. 11B shows the change in eGOS from 3 to 6 months by category, FIG. 11C shows the increase of eGOS level by number of patients and FIG. 11D shows the odds-ratio for the eGOS increase. As seen from FIG. 11A Ronopterin-treated patients show an increase in eGOS levels up to 4 levels and the overall increase in eGOS by at least 2 levels is encountered more often in Ronopterin-treated patients (22 vs. 9), see FIG. 11C. FIGS. 11A-D show for the Ronopterin-treated group more patients with higher increase in eGOS over time, however the increase is not (statistically) significant (FIG. 11D). In addition, FIGS. 11A-D show for the Ronopterin-treated group that there are significantly less patients with a decrease in eGOS over time (p=0.04).

Figure 12A:
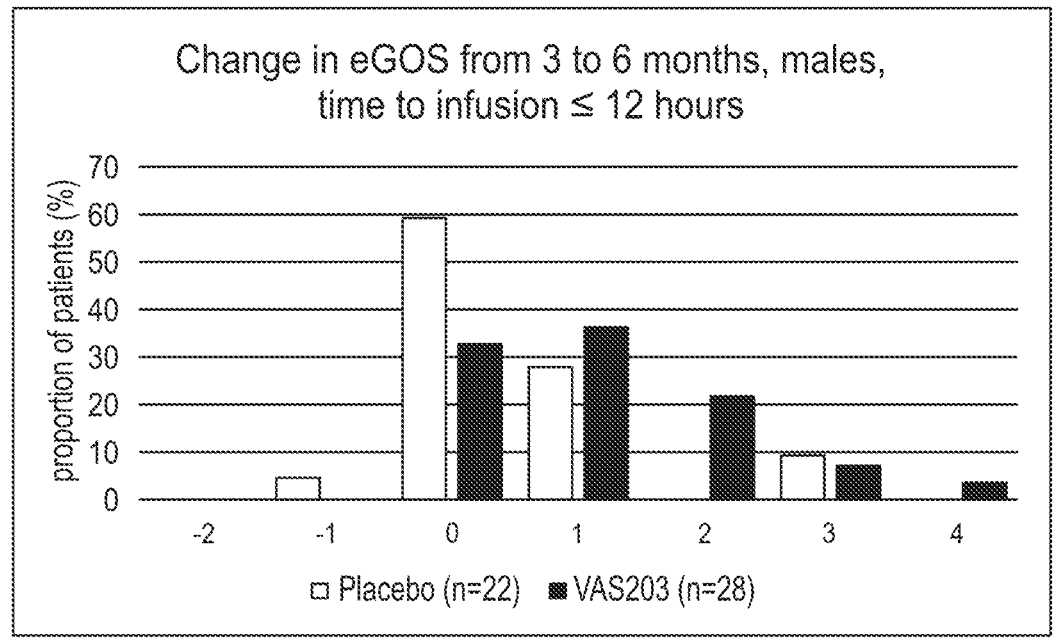
FIGS. 12A-H show the distribution of proportion of patients between Placebo and Ronopterin-treated patients with changes in eGOS from 3 to 6 months for male patients, depending on the time to infusion within 12 hours and after 12 hours after traumatic brain injury. In more detail.
Figure 12B:
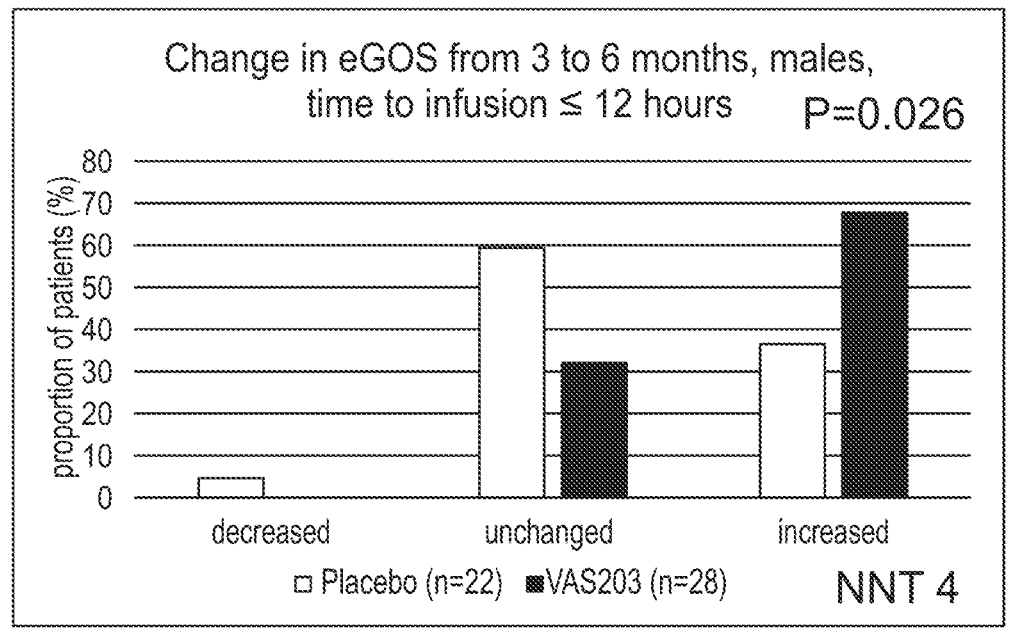
Figures 12C, 12D:
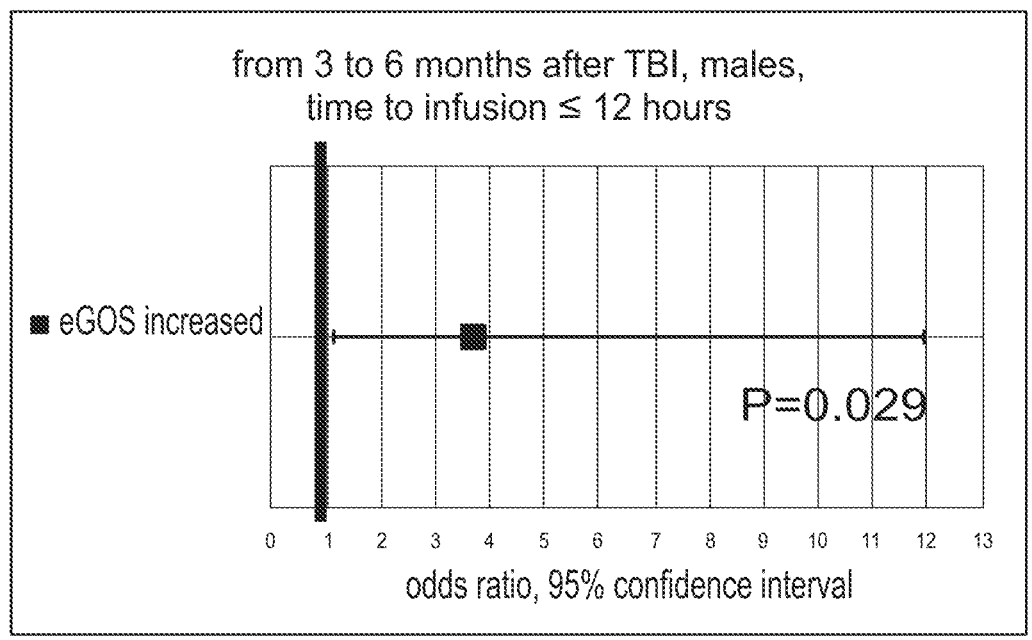
Figure 12E:
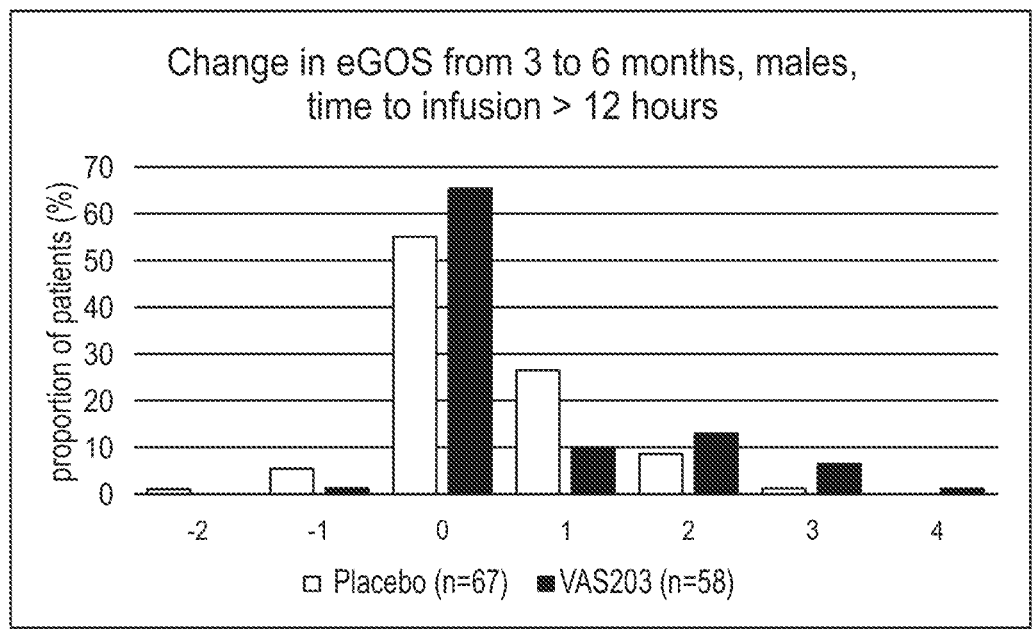
Figure 12F:
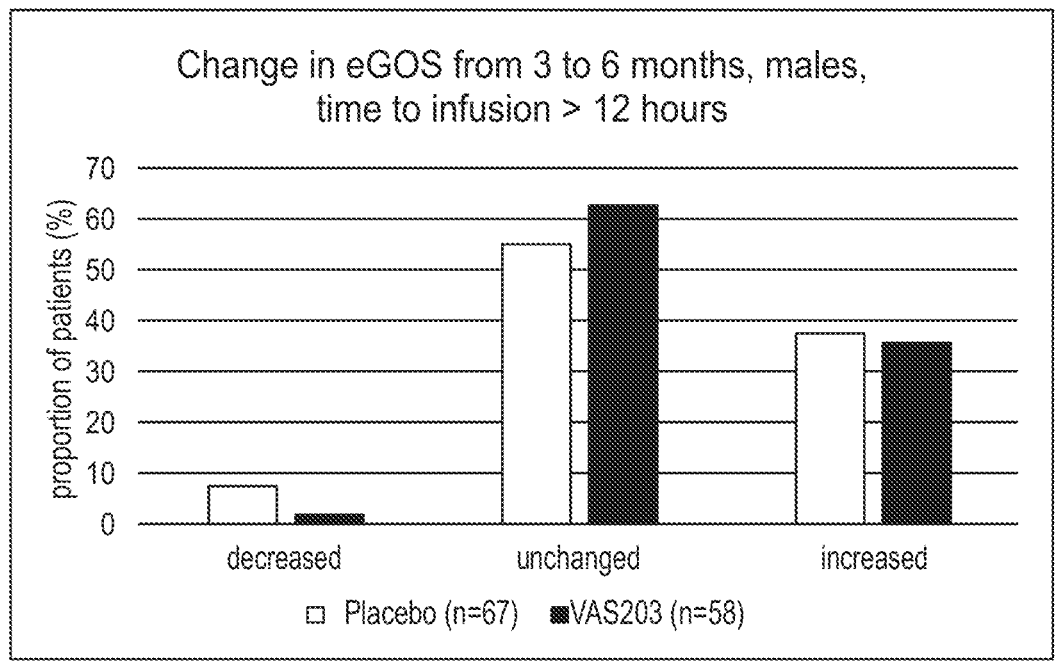
Figures 12G, 12H:
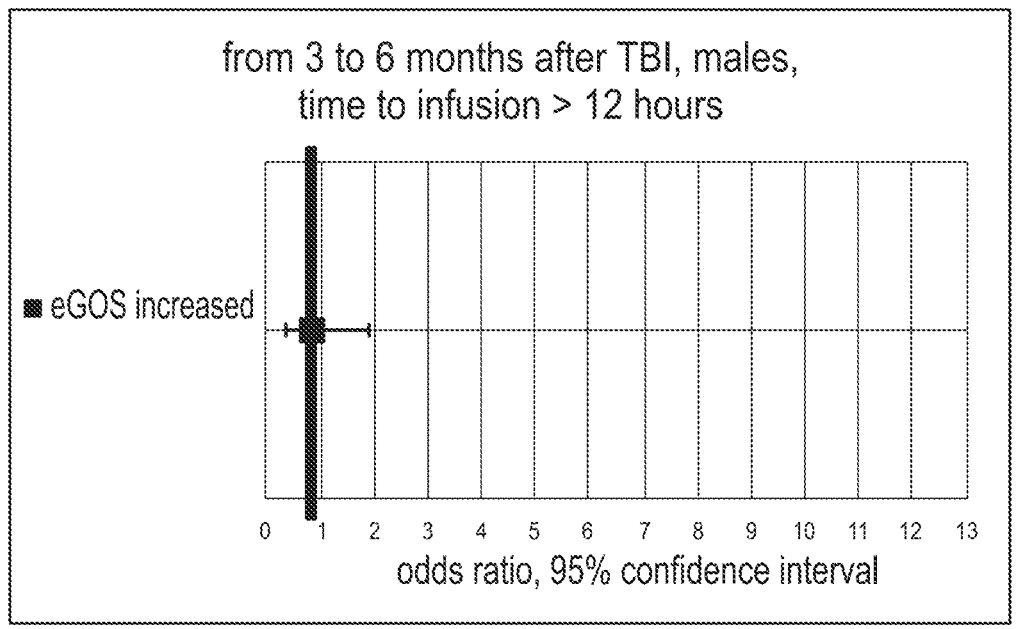

FIGS. 12A-H show the distribution of proportion of patients between Placebo and Ronopterin-treated patients with changes in eGOS from 3 to 6 months for male patients, depending on the time to infusion within 12 hours and after 12 hours after traumatic brain injury. In more detail, FIGS. 12A to 12D show the results for early infusion (≤12 hours) with FIG. 12A showing the change in eGOS from 3 to 6 months by eGOS level, FIG. 12B showing the change in eGOS from 3 to 6 months by category, FIG. 12C showing the increase of eGOS level by number of patients and FIG. 12D showing the odds-ratio for the eGOS increase. As seen from FIG. 12A Ronopterin-treated patients show an increase in eGOS levels up to 4 levels and the overall increase in eGOS by at least 2 levels is encountered more often in Ronopterin-treated patients (9 vs 2), see FIG. 12C. FIG. 12A to FIG. 12D show for male patients and administration of Ronopterin ≤12 hours that the increase in proportion of patients with an increase by at least 1 level is significant compared to Placebo-treated patients. FIG. 12E to FIG. 12H show the results for late infusion (>12 hours), with FIG. 12E showing the change in eGOS from 3 to 6 months by eGOS level, FIG. 12F showing the change in eGOS from 3 to 6 months by category, FIG. 12G showing the increase of eGOS level by number of patients and FIG. 12H showing the odds-ratio for the eGOS increase. Ronopterin-treated patients show an increase in eGOS levels up to 4 levels (FIG. 12E). Overall, increase in eGOS by at least 2 levels is encountered more often in Ronopterin-treated patients (13 vs 7), see FIG. 12G.

Figure 13A:
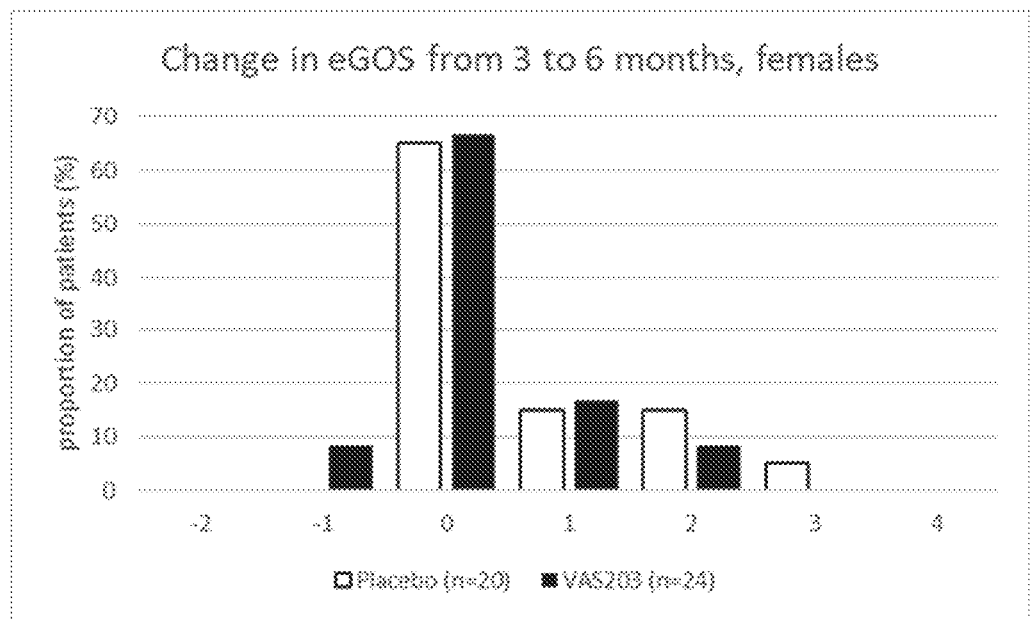
FIGS. 13A-D show the distribution of proportion of patients between Placebo and Ronopterin-treated patients with changes in eGOS from 3 to 6 months for female patients.
Figure 13B:
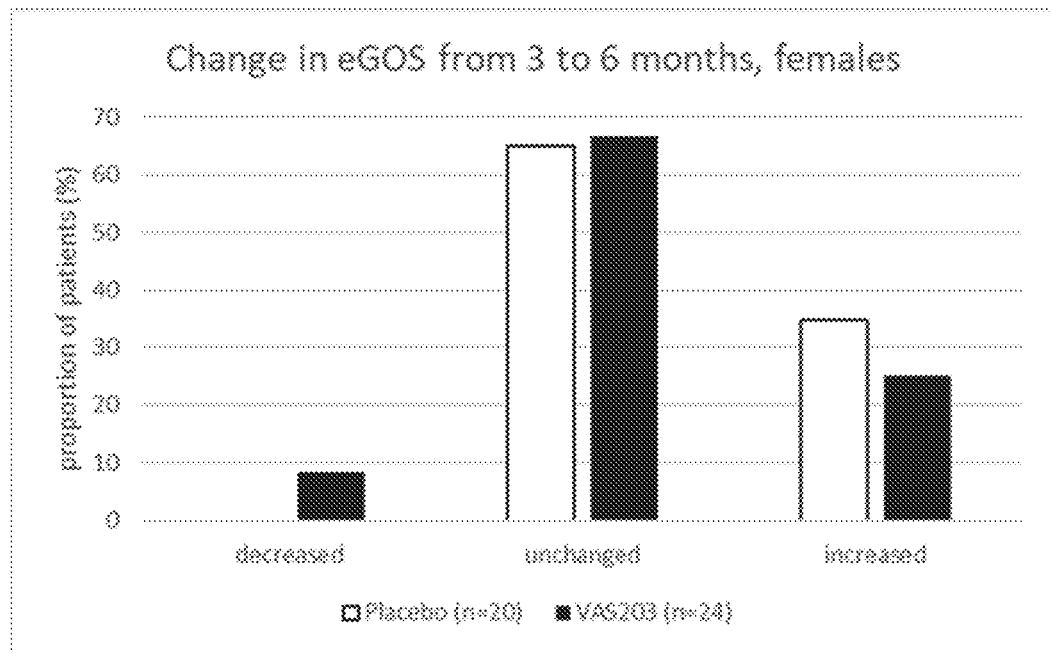
Figures 13C, 13D:
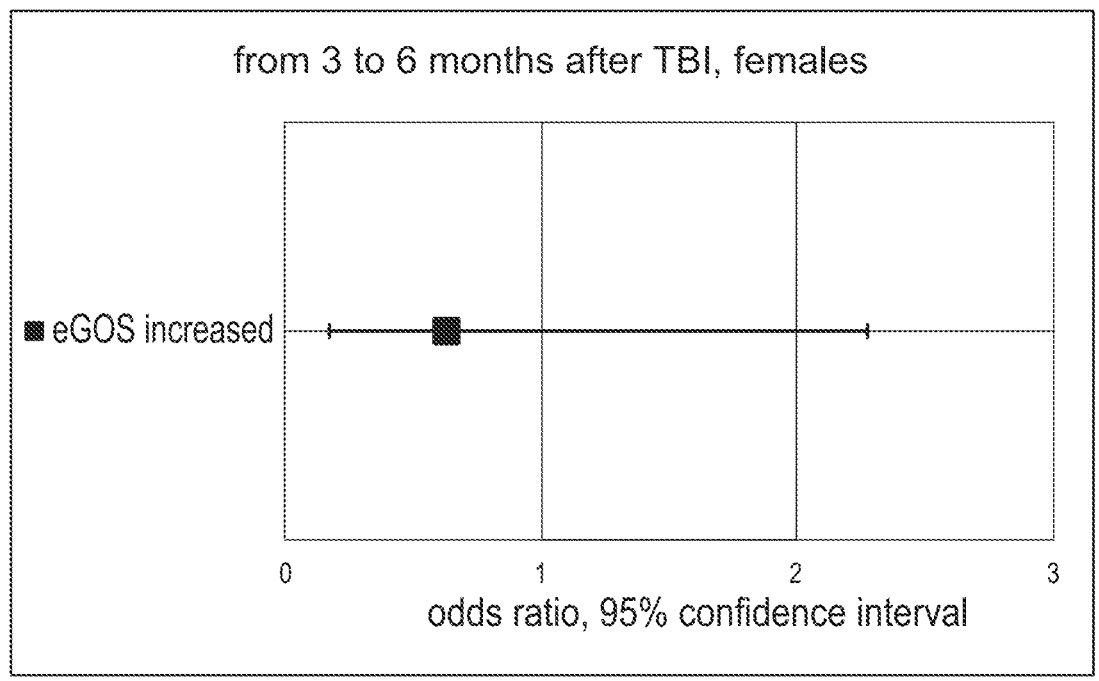

FIGS. 13A-D show the distribution of proportion of patients between Placebo and Ronopterin-treated patients with changes in eGOS from 3 to 6 months for female patients. FIG. 13A shows the change in eGOS from 3 to 6 months by eGOS level, FIG. 13B shows the change in eGOS from 3 to 6 months by category, FIG. 13C shows the increase of eGOS level by number of patients and FIG. 13D shows the odds-ratio for the eGOS increase. As seen from FIG. 11A Ronopterin-treated patients show an increase in eGOS levels up to 2 levels and the overall increase in eGOS by at least 2 levels is encountered less often in Ronopterin-treated patients (2 vs 4), see FIG. 13C. FIGS. 13A-D show for the Ronopterin-treated group less female patients with higher increase in eGOS over time, however the increase is not (statistically) significant (FIG. 13D).

Figure 14A:
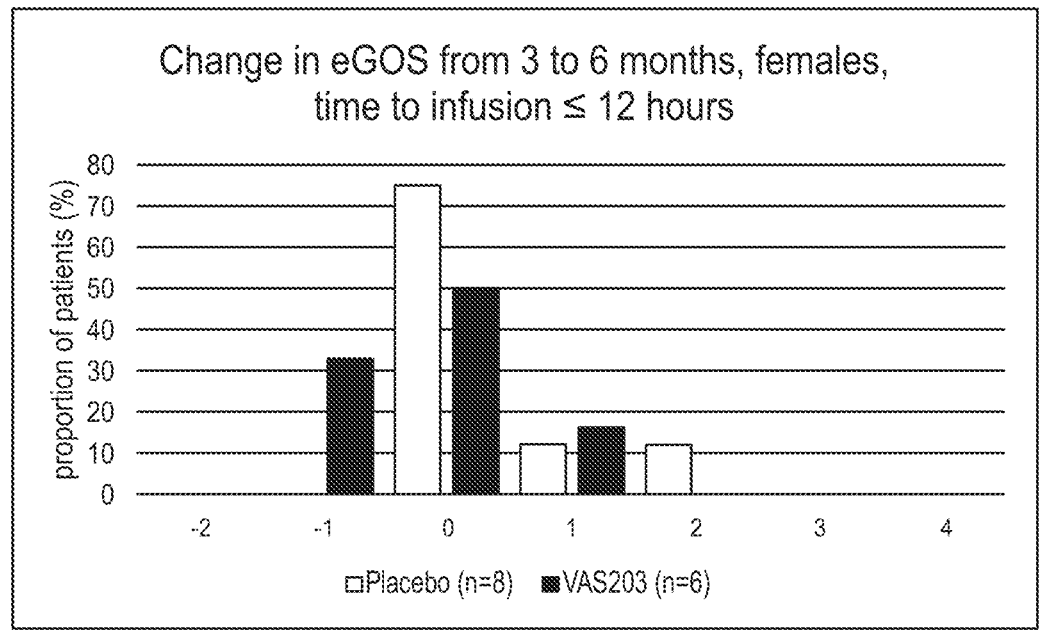
FIGS. 14A-H show the distribution of proportion of patients between Placebo and Ronopterin-treated patients with changes in eGOS from 3 to 6 months for female patients, depending on the time to infusion within 12 hours and after 12 hours after traumatic brain injury. In more detail.
Figure 14B:
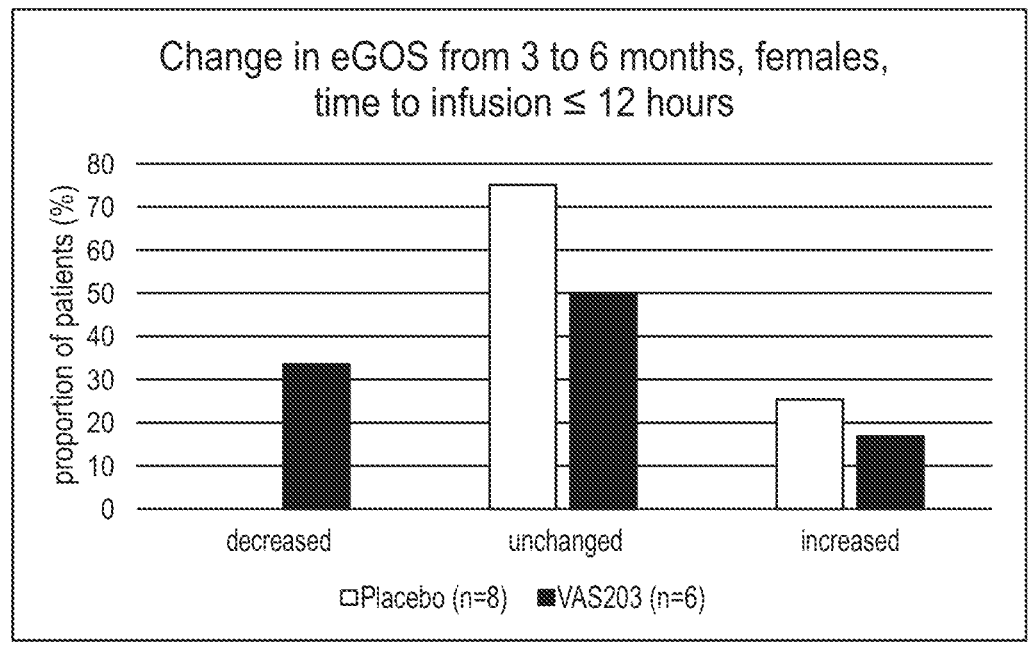
Figures 14C, 14D:
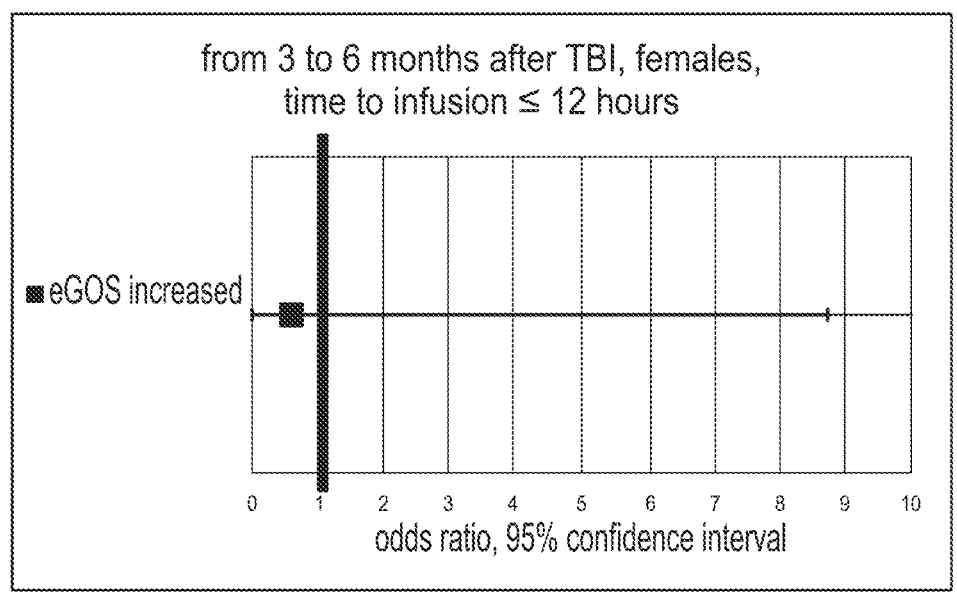
Figure 14E:
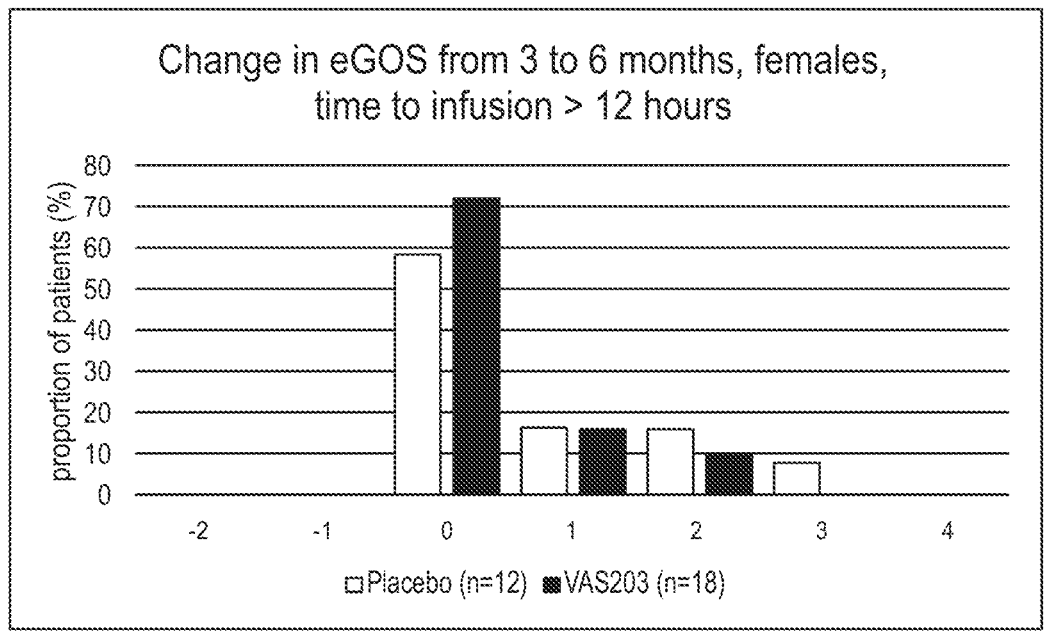
Figure 14F:
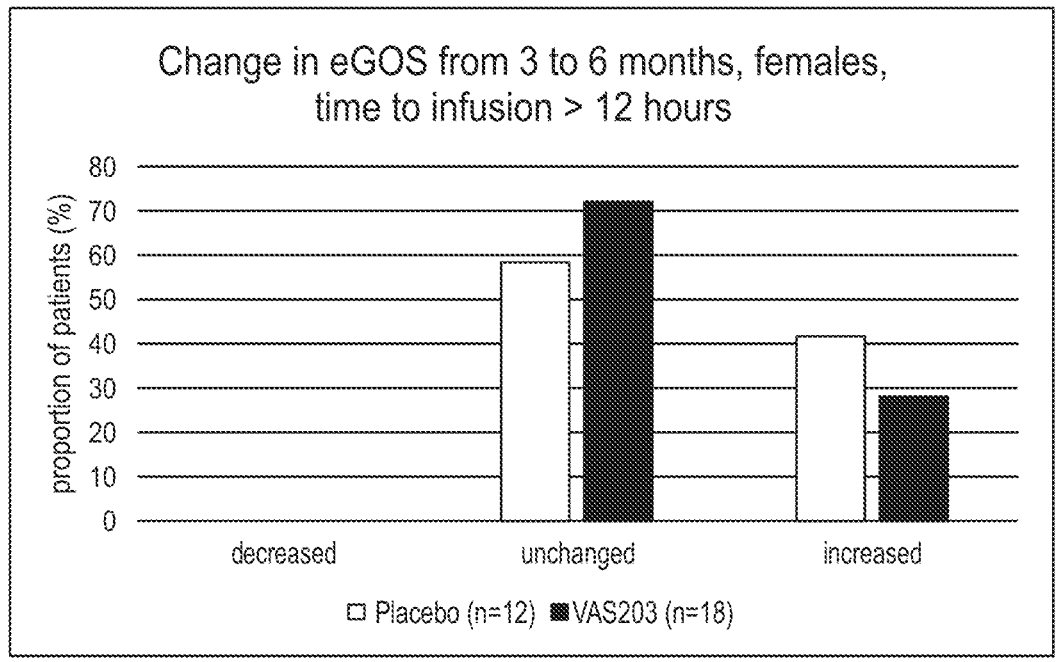
Figures 14G, 14H:
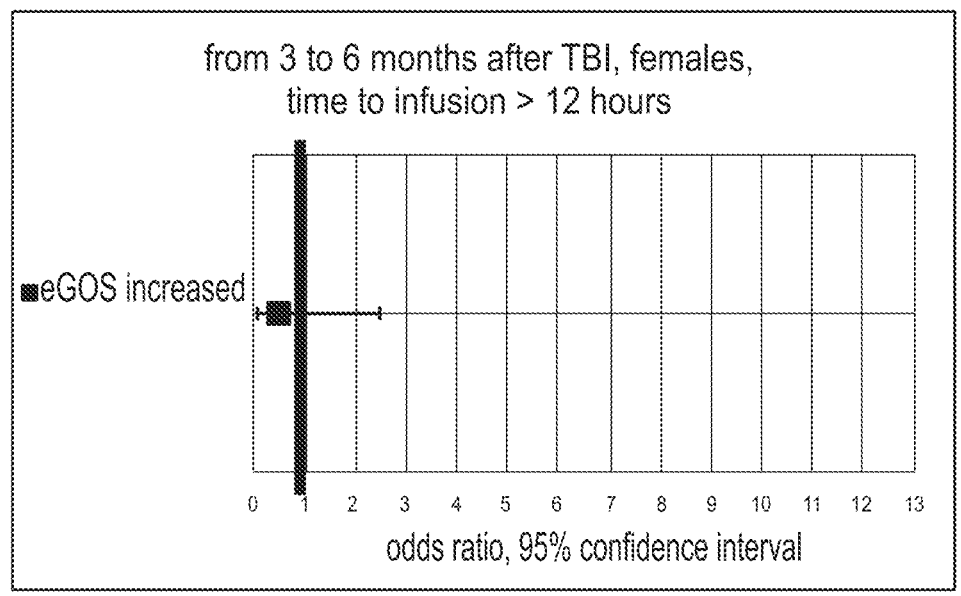

FIGS. 14A-H show the distribution of proportion of patients between Placebo and Ronopterin-treated patients with changes in eGOS from 3 to 6 months for female patients, depending on the time to infusion within 12 hours and after 12 hours after traumatic brain injury. In more detail, FIGS. 14A to 14D show the results for early infusion (≤12 hours) with FIG. 14A showing the change in eGOS from 3 to 6 months by eGOS level, FIG. 14B showing the change in eGOS from 3 to 6 months by category, FIG. 14C showing the increase of eGOS level by number of patients and FIG. 14D showing the odds-ratio for the eGOS increase. As seen from FIG. 14A Ronopterin-treated patients show an increase in eGOS levels up to 2 levels and the overall increase in eGOS by at least 2 levels is encountered less often in Ronopterin-treated patients (0 vs 1), see FIG. 14C. FIG. 14A to FIG. 14D show for female patients and administration of Ronopterin ≤12 that there are less female eGOS responders but that there is higher Good Recovery at 3 months. FIG. 14E to FIG. 14H show the results for late infusion (>12 hours), with FIG. 14E showing the change in eGOS from 3 to 6 months by eGOS level, FIG. 14F showing the change in eGOS from 3 to 6 months by category, FIG. 14G showing the increase of eGOS level by number of patients and FIG. 14H showing the odds-ratio for the eGOS increase. Ronopterin-treated female patients show an increase in eGOS levels up to 2 levels (FIG. 14E). Overall, increase in eGOS by at least 2 levels is encountered less often in Ronopterin-treated patients (2 vs 3), see FIG. 14G.

FIG. 15 shows the impact of time to infusion, sex, and age on the proportion of Good Recovery (eGOS value of 7 or 8) in Placebo and Ronopterin-treated patients expressed as Odds Ratio with 95% Confidence Intervals. As evident from FIG. 15, early infusion (≤12 hours) is associated with higher Odds Ratio in favor of Ronopterin in female and male patients, mainly for the tested female patient population with an age of 18 to 39 years, i.e. <40 years and in male patients with an age of ≥40 years. Late infusion (>12 hours) is associated with higher Odds Ratio in favor of Ronopterin in female patients, mainly in the female patient population with an age≥40 years. (The high Confidence Intervals are related to the small number of patients in the sex- and age-dependent subgroups of analysis.) At 3 months, the Odds Ratios reveal that female patients show highest impact of Ronopterin compared to male patients: early infusion: 1.4, 0.02-8.2 vs 0.4, 0.09-1.9; late infusion: 10.2, 0.5-204 vs 0.2, 0.05-0.6). At 6 months, the Odds Ratios are higher in male patients compared to female patients (2.2, 0.6-7.6 vs 1.5, 0.2-23), especially with early infusion. With late infusion, the Odds Ratios are higher in female patients compared to male patients (5.5, 0.6-53 vs 0.6, 0.3-1.4).

Figure 16A:
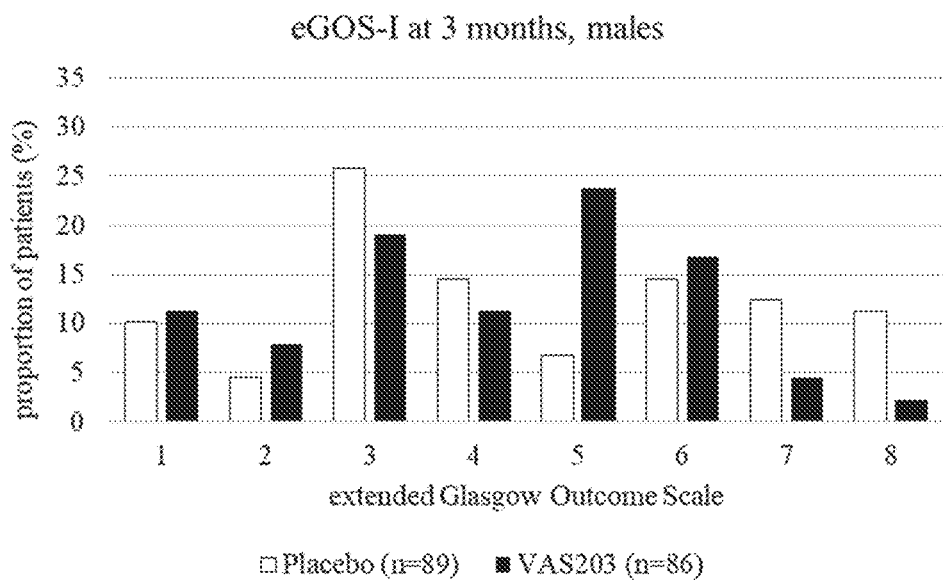
FIGS. 16A-D show the distribution of proportion of patients for the 8 eGOS levels in Placebo and Ronopterin-treated patients at 3 and 6 months in male and female patients, with males (n=179) and females (n=44).
Figure 16B:
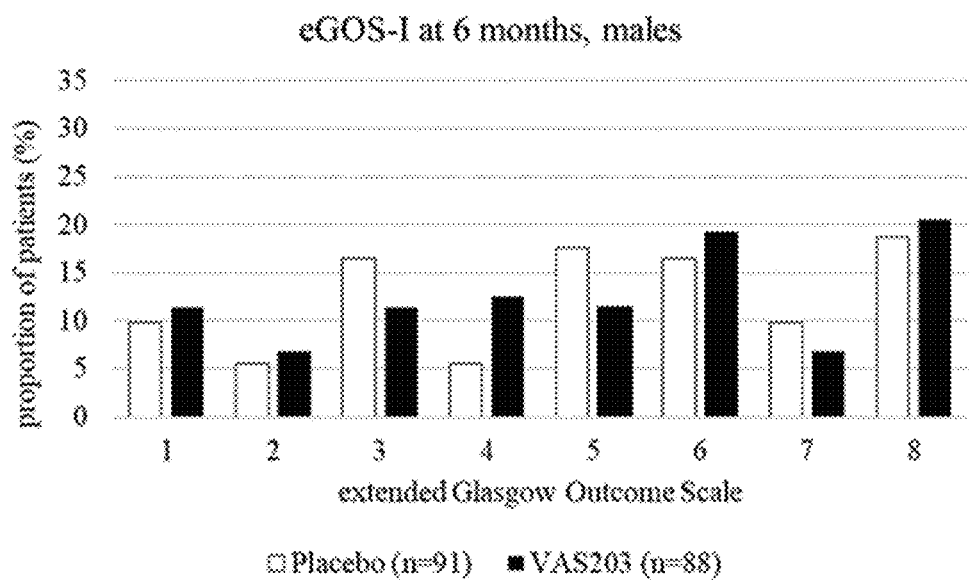
Figure 16C:
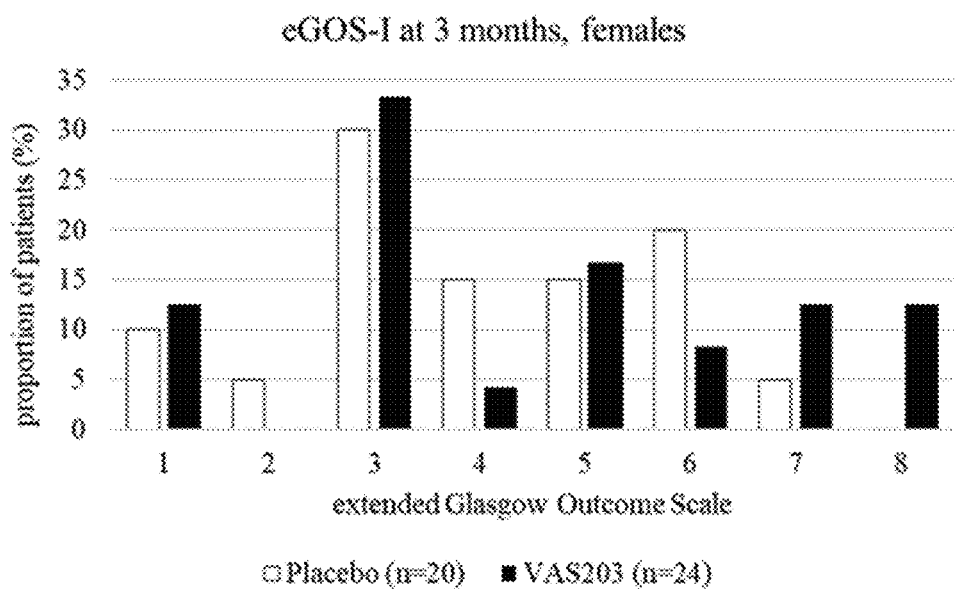
Figure 16D:
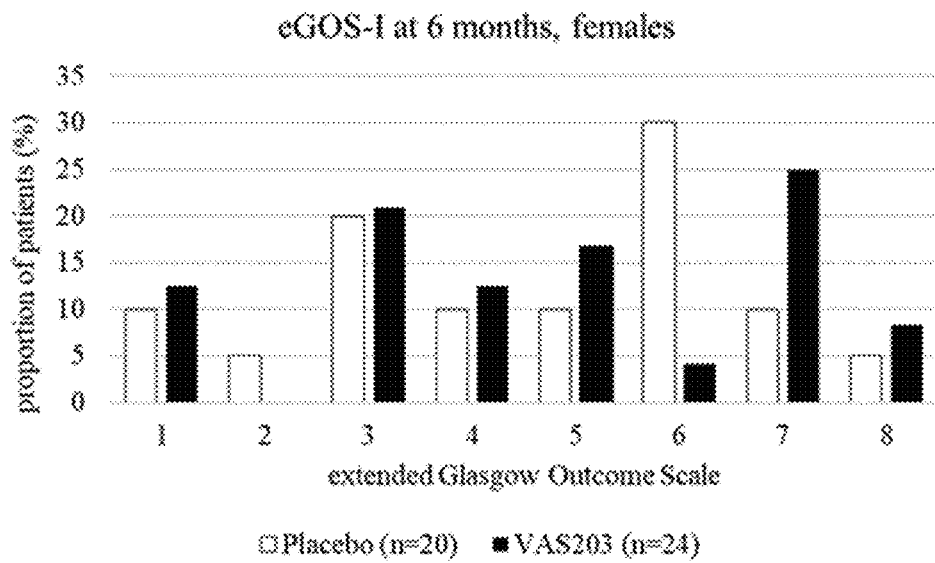

FIGS. 16A-D show the distribution of proportion of patients for the 8 eGOS levels in Placebo and Ronopterin-treated patients at 3 and 6 months in male and female patients, with males (n=179) and females (n=44). FIG. 16A shows the proportion of patients for the 8 eGOS levels in Placebo and Ronopterin-treated patients at 3 months in male patients, FIG. 16B shows the proportion of patients for the 8 eGOS levels in Placebo and Ronopterin-treated patients at 6 months in male patients, FIG. 16C shows the proportion of patients for the 8 eGOS levels in Placebo and Ronopterin-treated patients at 3 months in female patients and FIG. 16D shows the proportion of patients for the 8 eGOS levels in Placebo and Ronopterin-treated patients at 6 months in female patients. As can be seen from FIG. 16, at 3 months, male patients show lower proportion of eGOS levels 7 and 8 (Good Recovery) compared to female patients, reflecting more beneficial impact in female patients. At 6 months, male patients show an increase in proportion of eGOS levels 7 and 8 compared to 3 months. Female patients show an increase in Good Recovery from 3 to 6 months.

Figure 17A:
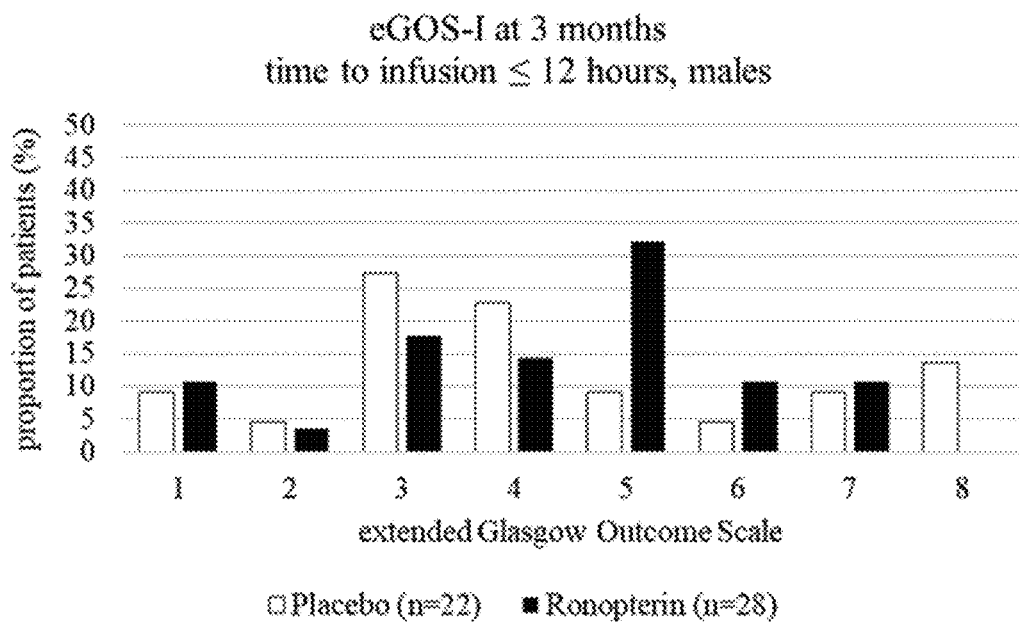
FIGS. 17A-D show the distribution of proportion of patients for the 8 eGOS levels in Placebo and Ronopterin-treated male patients with early and late infusion, with 179 male patients (n=179) being included.
Figure 17B:
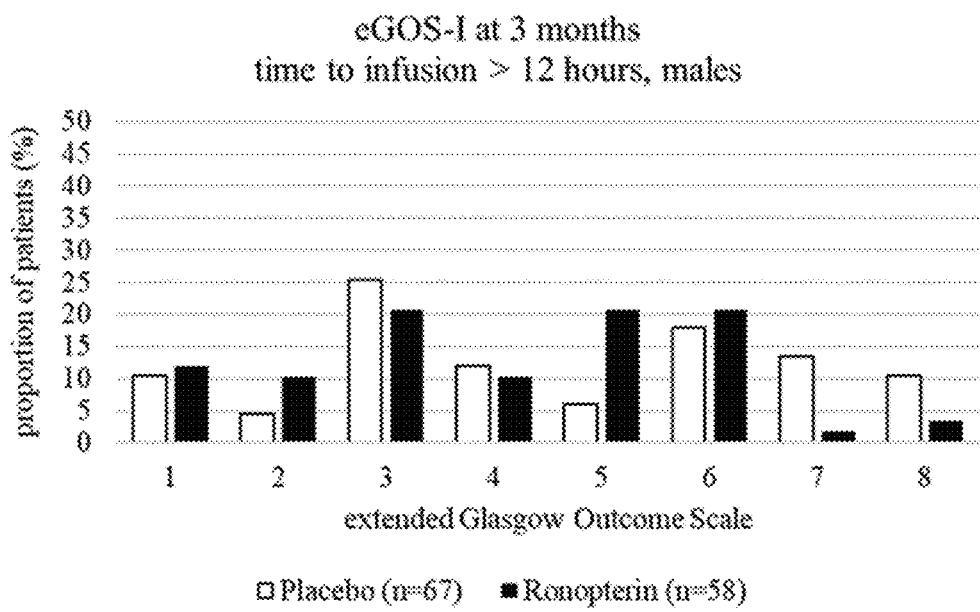
Figure 17C:
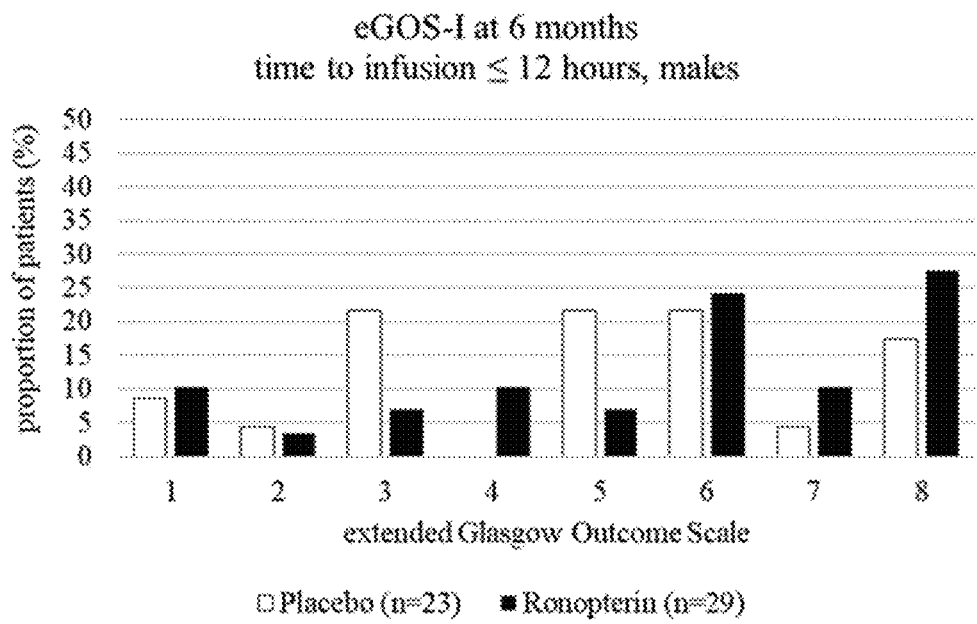
Figure 17D:
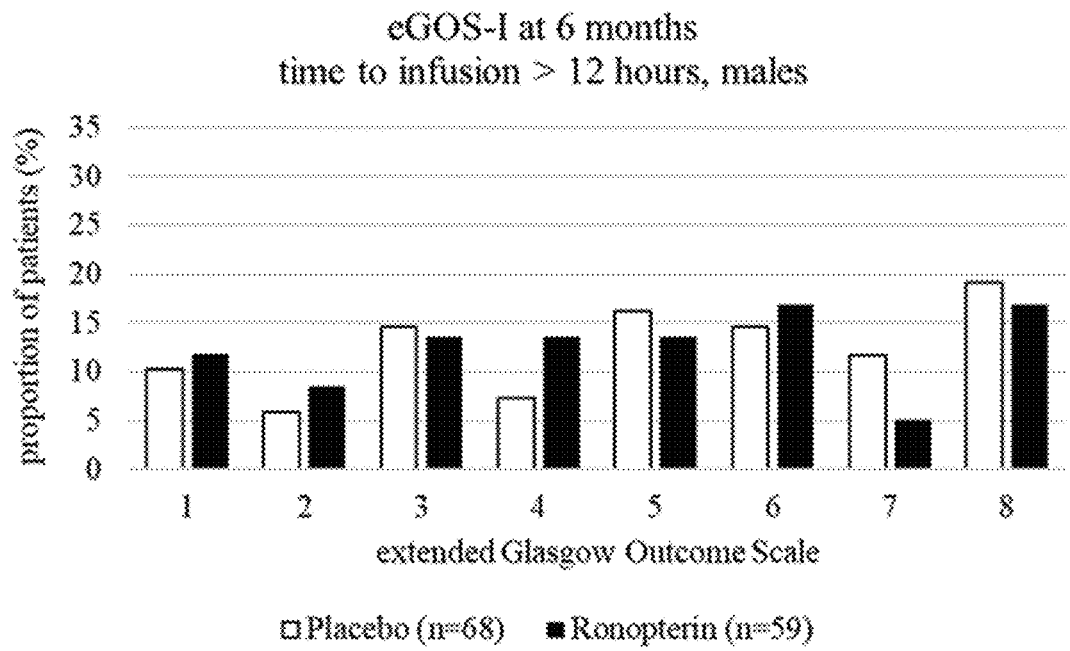

FIGS. 17A-D show the distribution of proportion of patients for the 8 eGOS levels in Placebo and Ronopterin-treated male patients with early and late infusion, with 179 male patients (n=179) being included. FIG. 17A shows the proportion of patients for the 8 eGOS levels in Placebo and Ronopterin-treated patients at 3 months in male patients for early infusion (≤12 hours), FIG. 17B shows the proportion of patients for the 8 eGOS levels in Placebo and Ronopterin-treated patients at 6 months in male patients for late infusion (>12 hours), FIG. 17C shows the proportion of patients for the 8 eGOS levels in Placebo and Ronopterin-treated patients at 6 months in male patients for early infusion (≤12 hours) and FIG. 17D shows the proportion of patients for the 8 eGOS levels in Placebo and Ronopterin-treated patients at 6 months in male patients for late infusion (>12 hours). As can be seen from FIGS. 17A-D, early infusion (≤12 hours) is associated with an increase in proportion of male patients with Good Recovery (eGOS 7 and 8) exceeding the proportion in Placebo-treated patients from 3 to 6 months. Late infusion (>12 hours) is associated with an increase in proportion of male patients with Good Recovery (eGOS 7 and 8) which, however, is less pronounced compared to Placebo-treated patients from 3 to 6 months. Overall, early infusion is associated with higher proportion of Good Recovery at 6 months in the Ronopterin-treated male patients.

Figure 18A:
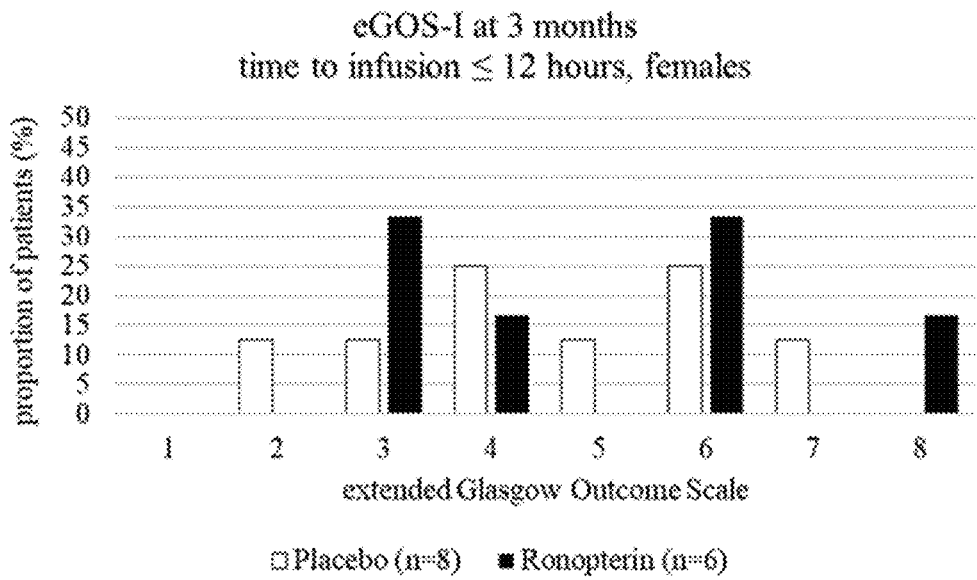
FIGS. 18A-D show the distribution of proportion of patients for the 8 eGOS levels in Placebo and Ronopterin-treated female patients with early and late infusion, with 44 female patients (n=44) being included.
Figure 18B:
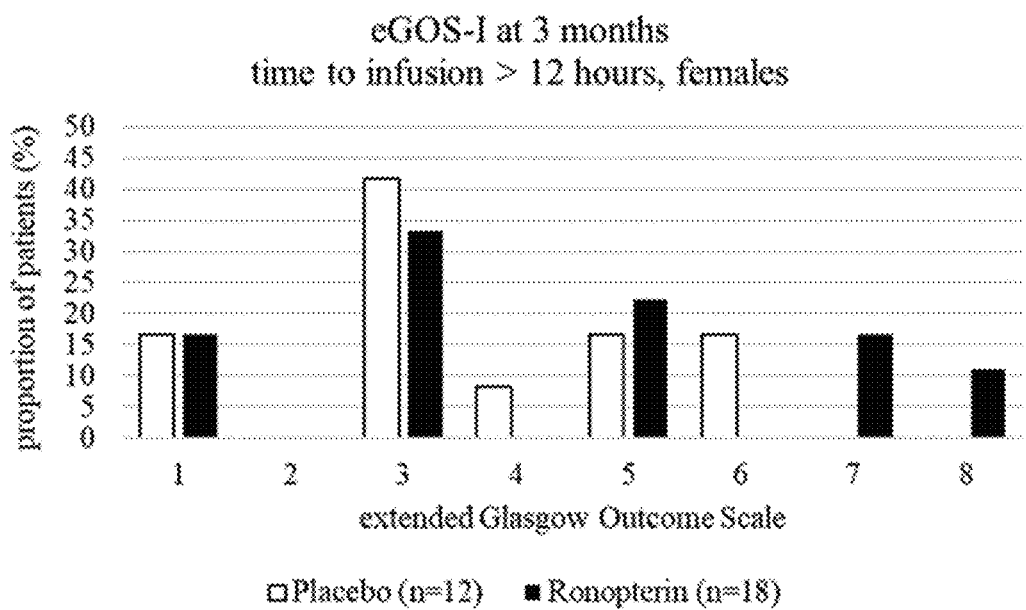
Figure 18C:
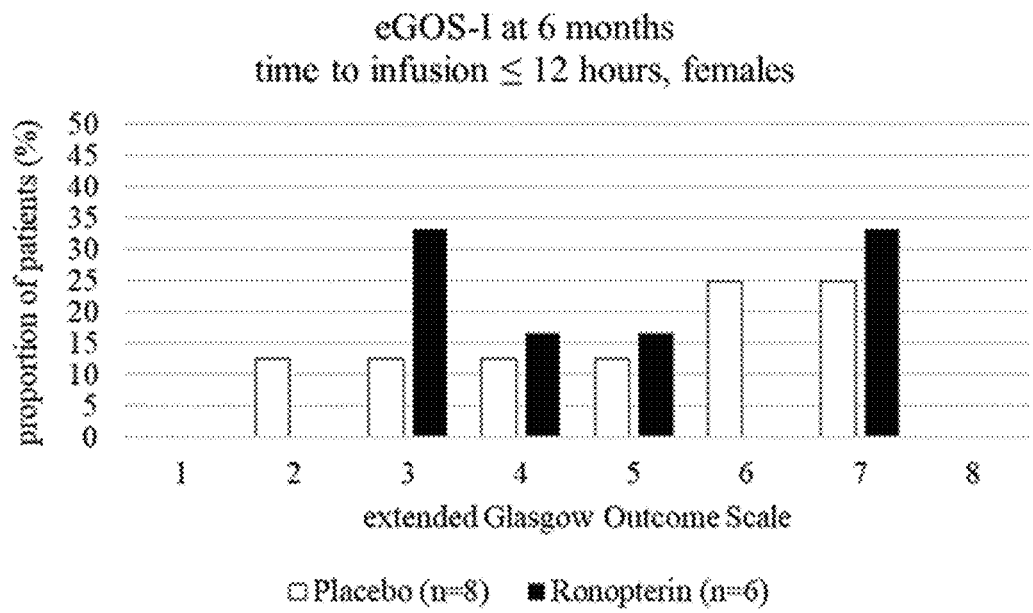
Figure 18D:
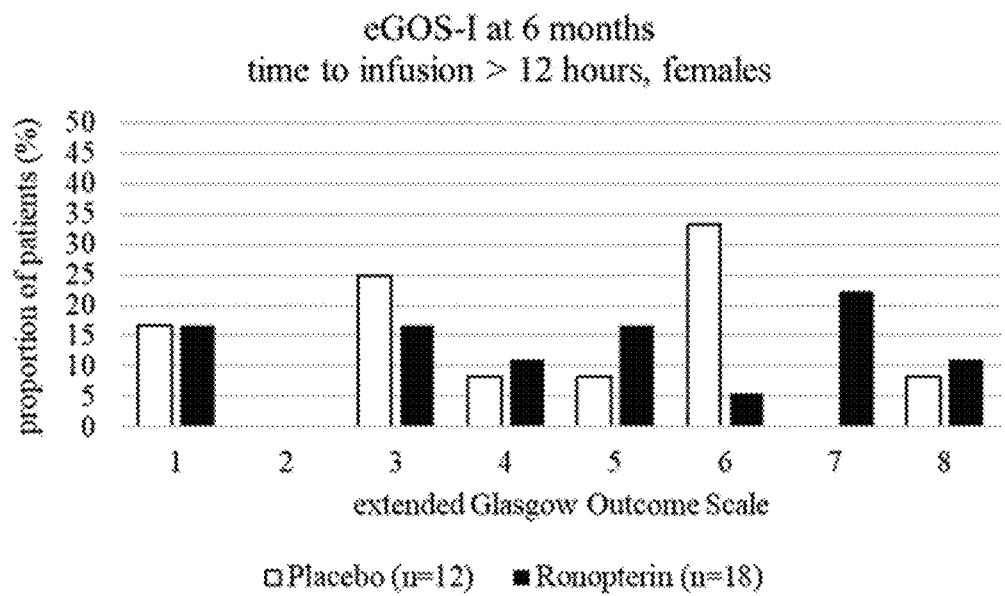

FIGS. 18A-D show the distribution of proportion of patients for the 8 eGOS levels in Placebo and Ronopterin-treated female patients with early and late infusion, with 44 female patients (n=44) being included. FIG. 18A shows the proportion of patients for the 8 eGOS levels in Placebo and Ronopterin-treated patients at 3 months in female patients for early infusion (≤12 hours), FIG. 18B shows the proportion of patients for the 8 eGOS levels in Placebo and Ronopterin-treated patients at 6 months in female patients for late infusion (>12 hours), FIG. 18C shows the proportion of patients for the 8 eGOS levels in Placebo and Ronopterin-treated patients at 6 months in female patients for early infusion (≤12 hours) and FIG. 18D shows the proportion of patients for the 8 eGOS levels in Placebo and Ronopterin-treated patients at 6 months in female patients for late infusion (>12 hours). As evident from FIGS. 18A-D, early infusion (≤12 hours) is associated with an increase in proportion of female patients with Good Recovery (eGOS 7 and 8) exceeding the proportion in Placebo-treated patients from 3 to 6 months. Late infusion (>12 hours) is associated with an increase in proportion of female patients with Good Recovery (eGOS 7 and 8) exceeding the proportion in Placebo-treated patients from 3 to 6 months. Overall, early infusion is associated with higher proportion of Good Recovery at 6 months in the Ronopterin-treated female patients.

The impact of age and sex on eGOS is also summarized in the following Tables.

TABLE 3

Good Recovery (eGOS ≥ 7) at 6 months

| Odds ratio, 95% CI | ≤12 hours | >12 hours |
|---|---|---|
| 18-39 years | | |
| Male | 1.4 (0.3-5.9); n = 32 | 0.6 (0.2-1.6); n = 58 |
| Female | 6.0 (0.2-163); n = 7 | 2.3 (0.2-33); n = 16 |
| 40-60 years | | |
| Male | 9.0 (0.4-194); n = 20 | 0.6 (0.2-2.2); n = 69 |
| Female | 0.3 (0.01-11.3); n = 7 | 6.2 (0.3-147); n = 14 |
| All males Females 18-39 years | | |
| All males 18-60 years | 2.2 (0.6-7.6); n = 52 | |
| All males plus females 18-39 years | 2.4 (0.8-7.6); n = 59 | |
| All females 40-60 years | | 5.5 (0.6-53); n = 30 |
| All females, all times to infusion | 2.8 (0.6-12.6); n = 44 | |

The following conclusions can be drawn from Table 3:
Good Recovery at 6 months depends on time to infusion, age and sex
  All males (18-60 years) show best Good Recovery (meaning an eGOS≥7, i.e. 7 or 8) at 6 months with time to infusion ≤12 hours
  Females (18-39 years) show higher Odds Ratio for Good Recovery at 6 months with time to infusion ≤12 hours
  All females (18-60 years) show best Good Recovery at 6 months at all times to infusion
  Females (40-60 years) show best Good Recovery at 6 months with time to infusion >12 hours
  Males (18-60 years): early time to infusion
  Young females (18-39 years): all times to infusion
  Older females (40-60 years): late time to infusion This means the following for the question of choosing the timepoint of infusion/administration:
  Early infusion: all males (18-60 years) and young females (18-39 years)
  Late infusion: all females (18-60 years)
  All times to infusion: young females (18-39 years)

TABLE 4

Good Recovery (eGOS ≥ 7) at 3 months

| Odds ratio, 95% CI | ≤12 hours | >12 hours |
|---|---|---|
| 18-39 years | | |
| Male | 0.4 (0.08-2.2); n = 30 | 0.2 (0.03-0.85); n = 58 |
| Female | 1.5 (0.06-41); n = 7 | 6.5 (0.27-161); n = 16 |
| 40-60 years | | |
| Male | 0.7 (0.01-38); n = 20 | 0.2 (0.02-1.4); n = 67 |
| Female | 1.3 (0.02-83); n = 7 | 4.2 (0.2-102); n = 14 |
| All females (18-60 years) | 1.4 (0.07-28.1); n = 14 | |
| All females (18-60 years) | | 10.2 (0.5-204); n = 30 |
| Females 18-39 years, all times to infusion | 4.2 (0.4-47); n = 23 | |
| Females 40-60 years, all times to infusion | 5.7 (0.3-126); n = 21 | |

The following conclusions can be drawn from Table 4:
Good Recovery at 3 months depends on time to infusion, age and sex
  Females (18-39 years) show higher Odds Ratio for Good Recovery at 3 months with time to infusion >12 hours
  Females (40-60 years) show higher Odds Ratio for Good Recovery at 3 months with time to infusion >12 hours
  Females (18-39 years) show Good Recovery at 3 months at all times to infusion
  Females (40-60 years) show Good Recovery at 3 months at all times to infusion
  All females (18-60 years): all times to infusion This means the following for the question of choosing the timepoint of infusion/administration:
  Early infusion: all females (18-60 years)
  Late infusion: all females (18-60 years)
  All times to infusion: all females (18-60 years)

TABLE 5

| Improvement in eGOS from 3 to 6 months, at least + 1 eGOS level | | |
|---|---|---|
| Odds ratio, 95% CI | ≤12 hours | >12 hours |
| 18-39 years | | |
| Male | 5.4 (1.1-26); n = 30; p = 0.04 | 0.7 (0.2-1.9); n = 58 |
| Female | 1.5 (0.06-41); n = 7 | 0.3 (0.04-2.8); n = 16 |
| 40-60 years | | |
| Male | 2.3 (0.4-14.6); n = 20 | 0.98 (0.3-2.8); n = 67 |
| Female | 0.3 (0.01-11.3); n = 7 | 1.3 (0.1-18); n = 14 |
| All males 18-60 years | 3.7 (1.1-12); n = 50; p = 0.03 | |
| All males 18-60 years and young females 18-39 years | 3.4 (1.2-10.2); n = 57; p = 0.03 | |

The following conclusions can be drawn from Table 5:
Improvement in eGOS from 3 to 6 months depends on time to infusion, age and sex
  Males (18-39 years) show higher OR for improvement over time with time to infusion ≤12 hours
  Males (40-60 years) show higher OR for improvement over time with time to infusion ≤12 hours
  Females (18-39 years) show higher OR for improvement over time with time to infusion ≤12 hours
  Females (40-60 years) show higher OR for improvement over time with time to infusion >12 hours
  All males (18-60 years): time to infusion ≤12 hours
  Females (18-39 years): time to infusion ≤12 hours
  Females (40-60 years): time to infusion >12 hours
This means the following for the question of choosing the timepoint of infusion/administration:
  Early infusion: all male patients (18-60 years) and young female patients (18-39 years)
  Late infusion: females (40-60 years)

Pharmacokinetic Results:

An exposure control was performed with samples collected after end of infusion and 12 hours after end of infusion. Due to the high sensibility of Ronopterin to oxidation, no utilizable values could be obtained for Ronopterin and, therefore, the first metabolite, 4-amino-dihydrobiopterin, was used as a surrogate. The mean absolute concentration for the first metabolite of Ronopterin was 1071 ng/mL at the end of the infusion and 476 ng/mL 12 hours later (56% elimination). The mean absolute value for the second Ronopterin metabolite was 52 ng/mL at the end of the infusion and 37 ng/mL 12 hours after end of infusion.

Safety and Tolerability Results:

Overall, the Ronopterin study treatment was well-tolerated and no significant new safety findings were seen in the study. A slightly higher number of adverse events (AEs) and serious adverse events (SAEs) were seen in the Ronopterin group compared to the placebo groups. However, the number of related AE/SAEs were low and comparable between the groups.

The observed SAEs/AEs were expected for the patient population.

An increased ICP or e.g., intracerebral haematoma are normally classified as an AE or SAE. However, after TBI this and other pathophysiological responses of the brain can typically be expected and, thus, were recommended not to be considered as AE or SAE. The apparent increase in ICP increased compared to placebo (27 [23.9%] patients vs. 13 [11.7%] patients) may be due to the over-reporting of some centres.

A higher number of renal AEs (11:3) and SAEs were observed in the Ronopterin group compared to the placebo groups; however, this was not unexpected for pharmacodynamics of Ronopterin and the population under study.

It will be readily apparent to a person skilled in the art that varying substitutions and modifications may be made to the invention disclosed herein without departing from the scope and spirit of the invention.

As used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following items and claims.

1. A method of treating a human patient suffering from brain injury, wherein the method comprises (starting) administering to the patient within a time period of ≤12 hours after the occurrence of the brain injury a therapeutically effective amount of a compound having the formula (I):

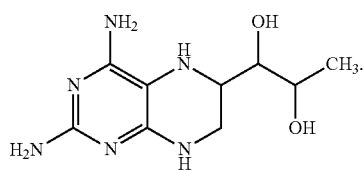

2. The method of item 1, comprising starting administering to the patient a therapeutically effective amount of the compound having the formula (I) within a time period of between 6 to 12 hours after the occurrence of the brain injury.

3. The method of item 1 or 2, wherein the compound having the formula (I) is administered by infusion.

4. The method of any of items 1 to 3, wherein the compound having the formula (I) is administered at a maximal daily dose in the range of 2.5 mg/kg body weight to 30.0 mg/kg body weight.

5. The method of item 4, wherein the compound having the formula (I) is administered at a total dose of 2.5, 5.0, 7.5, 10.0, 12.5, 15.0, 17.0, 20.0, or 30.0 mg/kg body weight.

6. The method of any of items 4 or 5, wherein the compound having the formula (I) is administered over a period of 12 to 96 hours.

7. The method of item 6, wherein the compound having the formula (I) is administered over a period of 24 to 48 hours or over a period of 24 to 72 hours.

8. The method of item 7, wherein the compound having the formula (I) is administered by infusion in a total dose of 17 mg/kg body weight over 48 hours, corresponding to a daily dose of 8.5 mg/kg body weight.

9. The method of item 7, wherein the compound having the formula (I) is administered by infusion in a total dose of 30.0 mg/kg body weight over 72 hours, corresponding to a daily dose of 10.0 mg/kg body weight.

10. The method of any of the forgoing items, wherein the brain injury is selected from the group consisting of traumatic brain injury, non-traumatic brain injury, elevated intracranial pressure, and secondary brain injury.

11. The method of item 10, wherein the secondary brain injury comprises a condition selected from the group consisting of edema formation from local or global hypoxia, ischemia, inflammation with and without infection, and neoplasms.

12. The method of item 11, wherein the neoplasm is selected from the group consisting of benign neoplasms, and malignant neoplasms.

13. The method of item 10, wherein the non-traumatic brain injury is selected from the group consisting of ischemic/hypoxic/hemorrhagic brain injury (e.g. stroke), post-resuscitation (after e.g. cardiac arrest), subarachnoid haemorrhage, anticoagulation-induced haemorrhage or wherein the non-traumatic brain injury is caused by inflammation and infection.

14. The method of item 13, wherein the inflammation is Systemic Inflammatory Response Syndrome (SIRS) or wherein the infection is selected from meningitis or encephalitis.

15. The method of item 10, wherein the brain injury is traumatic brain injury.

16. The method of item 15, wherein the patient to be treated has been diagnosed with complicated mild, moderate or severe traumatic brain injury.

17. The method of item 15 or 16, wherein the patient to be treated has been diagnosed with traumatic brain injury of a Glasgow Coma Score (GCS)≥3.

18. The method of item 16 or 17, wherein the traumatic brain injury requires intracranial pressure (ICP) monitoring.

19. The method of any of the forgoing items wherein the patient is up to 39 years old or is 40 years or older.

20. The method of item 19, wherein the patient has an age in the range of 18 to 39 years.

21. The method of item 20, wherein the value of the Extended Glasgow Outcome Scale (eGos) of the patient (as a measure of the reduction of traumatic brain injury) increases by at least 1 level when assessed six months after the occurrence of the traumatic brain injury and compared to the eGOS value of the patient determined three months after the occurrence of the traumatic brain injury.

22. The method of item 21, wherein the value of the Extended Glasgow Outcome Scale (eGOS) of the patient increases by at least 2 levels when assessed six months after the occurrence of the traumatic brain injury and compared to the eGOS value of the patient determined three months after the occurrence of the traumatic brain injury.

23. The method of item 21 or 22, wherein the eGOS value when assessed six months after the occurrence of the traumatic brain injury increases by 2, 3, 4 or 5 levels, compared to the eGOS value of the patient determined three months after the traumatic brain injury.

24. The method of any of items 20 to 23, wherein the patient reaches eGOS level 7 or eGOS level 8 six months after the traumatic brain injury.

25. The method of any of items 22 to 24, wherein the patient is male.

26. The method of item 20, wherein the patient reaches eGOS level 7 or eGOS level 8 three months after or six months after the occurrence of the traumatic brain injury.

27. The method of item 26, wherein the patient is female.

28. The method of any of items 26 to 27, wherein the eGOS value when assessed six months after the occurrence of the traumatic brain injury increases by at least 1 level or at least 2 levels and compared to the eGOS value of the patient determined three months after the traumatic brain injury.

29. The method of any of items 26 to 28, wherein the eGOS value when assessed six months after the occurrence of the traumatic brain injury increases by 2, 3, 4 or 5 levels, compared to the eGOS value of the patient determined three months after the traumatic brain injury.

30. The method of item 19, wherein the patient has an age in the range of 40 to 90 years, 40 to 80 years, 40 to 70 years or 40 to 65 years.

31. The method of item 30, wherein the patient has an age in the range of 40 to 60 years.

32. The method of item 30 or 31, wherein the patient is female.

33. The method of item 32, wherein the patient reaches eGOS level 7 or eGOS level 8 six months after the occurrence of the traumatic brain injury.

34. The method of item 32 or 33, wherein the value of the Extended Glasgow Outcome Scale (eGOS) of the patient increases by at least 1 level six months after the occurrence of the traumatic brain injury and compared to the eGOS value of the patient determined three months after the occurrence of the traumatic brain injury.

35. The method of any of items 32 to 34, wherein the value of the Extended Glasgow Outcome Scale (eGOS) of the patient increases by at least 2 levels when six months after the occurrence of the traumatic brain injury and compared to the eGOS value of the patient determined three months after the occurrence of the traumatic brain injury.

36. The method of any of items 31 to 35, wherein the eGOS value when assessed three months after the occurrence of the traumatic brain injury increases by 2, 3, 4 or 5 levels and compared to the eGOS value of the patient determined three months after the occurrence of the traumatic brain injury.

37. The method of any of items 20 to 36, wherein the treatment comprises providing within a period of 14 days after occurrence of the traumatic brain injury the patient with a low Therapy Intensity Level (TIL) treatment.

38. The method of item 37, wherein the low Therapy Intensity Level (TIL) treatment has a therapy index level between 3 and 10.

39. The method of any of the items 1 to 39, wherein the compound of formula (I) is 4-Amino-(6R,S)-5,6,7,8-tetrahydro-L-biopterin having the formula (Ia):

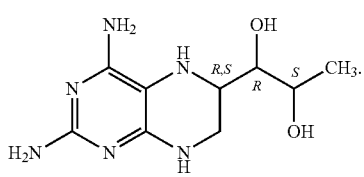

(Ia)

40. The method of item 39, wherein the compound (Ia) is a diastereomeric mixture that comprises more (6R)-4-Amino-5, 6, 7, 8-tetrahydro-L-biopterin than (6S)-4-Amino-5, 6, 7, 8-tetrahydro-L-biopterin.

41. The method of any of items 39 to 40, wherein infusion of the compound of formula (I) is carried out with a reconstituted solid composition of the compound of formula (I), wherein a unit dosage of the solid composition contains 650±60 mg of the free base of 4-Amino-(6R,S)-5,6,7,8-tetrahydro-L-biopterin, 140±30 mg of water of crystallization, 70±7 mg Na$_2$HPO$_4$·2H$_2$O, 16.5±2 mg NaH$_2$PO$_4$·2H$_2$O, and 350±30 mg NaCl or wherein a unit dosage of the composition contains 650±60 mg of the free base of 4-Amino-(6R,S)-5,6,7,8-tetrahydro-L-biopterin, 60±50 mg of water of crystallization, 70±7 mg Na$_2$HPO$_4$·2H$_2$O, 12±2.5 mg NaH$_2$PO$_4$·2H$_2$O, and 350±30 mg NaCl.

42. The method of item 41, wherein reconstitution comprises providing a vial containing 1 g of the unit dosage and adding 50 ml water to 1 g of the unit dosage.

43. A method of increasing the value of the Extended Glasgow Outcome Scale (eGOS) of a human patient suffering from brain injury, thereby improving the condition of the patient, wherein the value of the Extended Glasgow Outcome Scale (eGOS) of the patient reaches eGOS level 7 or eGOS level 8 six months after the occurrence of the brain injury, wherein the method comprises (starting) administering to the patient within a time period of ≤12 hours after the occurrence of the brain injury a therapeutically effective amount of a compound having the formula (I):

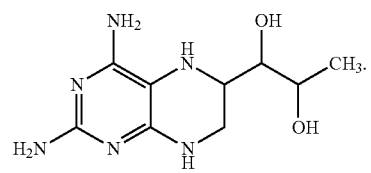

(I)

44. The method of item 43, wherein the eGOS value of the patient when assessed six months after the occurrence of the traumatic brain injury has increased by 2, or 3, or 4, or 5 eGOS levels compared to the eGOS value of the patient determined three months after the occurrence of the traumatic brain injury.

45. A method of increasing the value of the Extended Glasgow Outcome Scale (eGOS) of a human patient suffering from brain injury, thereby improving the condition of the patient, wherein the value of the Extended Glasgow Outcome Scale (eGOS) of the patient has increased by 2 or more six months after the occurrence of the brain injury and compared to the eGOS value determined three months after the occurrence of the brain injury, wherein the method comprises (starting) administering to the patient within a time period of ≤12 hours after the occurrence of the brain injury a therapeutically effective amount of a compound having the formula (I):

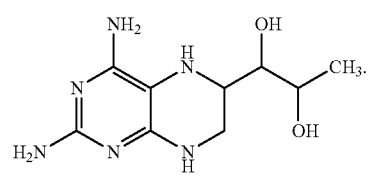

(I)

46. The method of item 45, wherein the value of the Extended Glasgow Outcome Scale (eGOS) of the patient has increased by 3, or 4 or 5 six months after the occurrence of the brain injury and compared to the eGOS value determined three months after the occurrence of the brain injury.

47. The method of item 45 or 47, wherein the value of the Extended Glasgow Outcome Scale (eGOS) of the patient reaches eGOS level 7 or eGOS level 8 six months after the occurrence of the brain injury.

48. The method of any of items 43 to 47, comprising starting administering to the patient a therapeutically effective amount of the compound having the formula (I) within a time period of between 6 to 12 hours after the occurrence of the brain injury.

49. The method of item 48, wherein the compound having the formula (I) is administered by infusion.

50. The method of item 49, wherein the compound having the formula (I) is administered at a maximal daily dose in the range of 2.5 mg/kg body weight to 30.0 mg/kg body weight.

51. The method of item 50, wherein the compound having the formula (I) is administered at a total dose 2.5, 5.0, 7.5, 10.0, 12.5, 15.0, 17.0, 20.0, or 30.0 mg/kg body weight.

52. The method of any of items 50 or 51, wherein the compound having the formula (I) is administered over a period of 12 to 96 hours or over a period of 24 to 72 hours.

53. The method of item 53, wherein the compound having the formula (I is administered over a period of 24 to 48 hours.

54. The method of item 53, wherein the compound having the formula (I) is administered by infusion in a total dose of 17 mg/kg body weight over 48 hours, corresponding to a daily dose 8.5 mg/kg body weight.

55. The method of item 53, wherein the compound having the formula (I) is administered by infusion in a total dose of 30.0 mg/kg body weight over 72 hours, corresponding to a daily dose of 10.0 mg/kg body weight.

56. The method of any of the forgoing items 43 to 55, wherein the brain injury is selected from the group consisting of traumatic brain injury, non-traumatic brain injury, elevated intracranial pressure, and secondary brain injury.

57. The method of item 56, wherein the secondary brain injury comprises a condition selected from the group consisting of edema formation from local or global hypoxia, ischemia, inflammation with and without infection, and neoplasms.

58. The method of item 57, wherein the neoplasm is selected from the group consisting of benign neoplasms and malignant neoplasms.

59. The method of item 56, wherein the non-traumatic brain injury is selected from the group consisting of ischemic/hypoxic/hemorrhagic brain injury (e.g. stroke), post-resuscitation (after e.g. cardiac arrest), subarachnoid haemorrhage, anticoagulation-induced haemorrhage or wherein the non-traumatic brain injury is caused by inflammation and infection.

60. The method of item 59, wherein the inflammation is Systemic Inflammatory Response Syndrome (SIRS) or wherein the infection is selected from meningitis or encephalitis.

61. The method of item 56, wherein the brain injury is traumatic brain injury.

62. The method of item 61, wherein the patient to be treated has been diagnosed with mild complicated, moderate or severe traumatic brain injury.

63. The method of item 61 or 62, wherein the patient to be treated has been with diagnosed with traumatic brain injury of a Glasgow Coma Score (GCS)≥3.

64. The method of item 62 or 63, wherein the traumatic brain injury requires intracranial pressure (ICP) monitoring.

65. The method of any of the forgoing items 43 to 64 wherein the patient is up to 39 years old or is 40 years or older.

66. The method of item 65, wherein the patient has an age in the range of 18 to 39 years.

67. The method of item 66, wherein the patient has an age in the range of 40 to 90 years, 40 to 80 years, 40 to 70 years or 40 to 65 years.

68. The method of any of items 65 to 67, wherein the treatment comprises providing within a period of 14 days after occurrence of the traumatic brain injury the patient with a low Therapy Intensity Level (TIL) treatment.

69. The method of item 68, wherein the low Therapy Intensity Level (TIL) treatment has a therapy index level between 3 and 10.

70. The method of any of the items 43 to 69, wherein the compound of formula (I) is 4-Amino-(6R,S)-5,6,7,8-tetrahydro-L-biopterin having the formula (Ia):

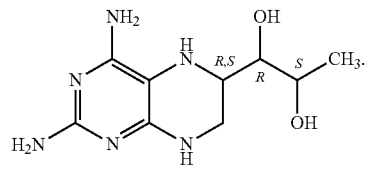

71. The method of item 70, wherein the compound (Ia) is a diastereomeric mixture that comprises more (6R)-4-Amino-5, 6, 7, 8-tetrahydro-L-biopterin than (6S)-4-Amino-5, 6, 7, 8-tetrahydro-L-biopterin.

72. The method of any of items 70 to 71, wherein infusion of the compound of formula (I) is carried out with a reconstituted solid composition of the compound of formula (I), wherein a unit dosage of the solid composition contains 650±60 mg of the free base of 4-Amino-(6R,S)-5,6,7,8-tetrahydro-L-biopterin, 140±30 mg of water of crystallization, 70±7 mg $Na_2HPO_4 \cdot 2H_2O$, 16.5±2 mg $NaH_2PO_4 \cdot 2H_2O$, and 350±30 mg NaCl or wherein a unit dosage of the composition contains 650±60 mg of the free base of 4-Amino-(6R,S)-5,6,7,8-tetrahydro-L-biopterin, 60±50 mg of water of crystallization, 70±7 mg $Na_2HPO_4 \cdot 2H_2O$, 12±2.5 mg $NaH_2PO_4 \cdot 2H_2O$, and 350±30 mg NaCl.

73. The method of item 72, wherein reconstitution comprises providing a vial containing 1 g of the unit dosage and adding 50 ml water to 1 g of the unit dosage.

74. A method of treating a human patient suffering from brain injury, wherein the patient is a female of an age of 40 years or older, and wherein the method comprises (starting) administering to the patient within a time period of >12 hours after the occurrence of the brain injury a therapeutically effective amount of a compound having the formula (I):

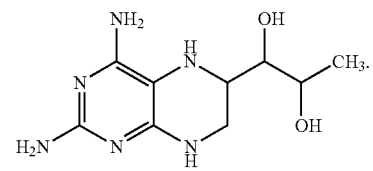

75. The method of item 74, comprising starting administering to the patient a therapeutically effective amount of the compound having the formula (I) within a time period of between 12 to 18 hours after the occurrence of the brain injury.

76. The method of item 74 or 75, wherein the compound having the formula (I) is administered by infusion.

77. The method of any of items 74 to 76, wherein the compound having the formula (I) is administered at a maximal daily dose in the range of 2.5 mg/kg body weight to 30.0 mg/kg body weight.

78. The method of item 77, wherein the compound having the formula (I) is administered at a total dose of 2.5, 5.0, 7.5, 10.0, 12.5, 15.0, 17.5, 20.0, or 30.0 mg/kg body weight.

79. The method of any of items 77 or 78, wherein the compound having the formula (I) is administered over a period of 12 to 96 hours.

80. The method of item 79, wherein the compound having the formula (I) is administered over a period of 24 to 48 hours or over a period of 24 to 72 hours.

81. The method of item 80, wherein the compound having the formula (I) is administered by infusion in a total dose of 17 mg/kg body weight over 48 hours, corresponding to a daily dose of 8.5 mg/kg body weight.

82. The method of any of the forgoing items 74 to 81, wherein the brain injury is selected from the group consisting of traumatic brain injury, non-traumatic brain injury, elevated intracranial pressure, and secondary brain injury.

83. The method of item 82, wherein the brain injury is traumatic brain injury.

84. The method of item 83, wherein the patient to be treated has been diagnosed with mild complicated, moderate or severe traumatic brain injury.

85. The method of item 83 or 84, wherein the patient to be treated has been with diagnosed with traumatic brain injury of a Glasgow Coma Score (GCS)≥3.

86. The method of item 84 or 85, wherein the traumatic brain injury requires intracranial pressure (ICP) monitoring.

87. The method of any of items 83 to 86, wherein the value of the Extended Glasgow Outcome Scale (eGOS) of the patient increases by at least 1 level or by at least 2 levels when assessed six after the occurrence of the traumatic brain injury and compared to the eGOS value of the patient determined three months after the occurrence of the traumatic brain injury.

88. The method of item 87, wherein the eGOS value when assessed six months after the occurrence of the traumatic brain injury increases by 2, 3.4 or 5 levels and compared to the eGOS value of the patient determined three months after the occurrence of the traumatic brain injury.

89. The method of any of items 87 to 88, wherein the patient reaches eGOS level 7 or eGOS level 8 six months after the traumatic brain injury.

90. The method of any of the items 74 to 89, wherein the compound of formula (I) is 4-Amino-(6R,S)-5,6,7,8-tetrahydro-L-biopterin having the formula (Ia):

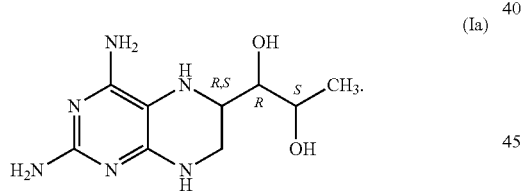

91. The method of item 90, wherein the compound (Ia) is a diastereomeric mixture that comprises more (6R)-4-Amino-5, 6, 7, 8-tetrahydro-L-biopterin than (6S)-4-Amino-5, 6, 7, 8-tetrahydro-L-biopterin.

92. The method of any of items 76 to 91, wherein infusion of the compound of formula (I) is carried out with a reconstituted solid composition of the compound of formula (I), wherein a unit dosage of the solid composition contains 650±60 mg of the free base of 4-Amino-(6R,S)-5,6,7,8-tetrahydro-L-biopterin, 140±30 mg of water of crystallization, 70±7 mg $Na_2HPO_4·2H_2O$, 16.5±2 mg $NaH_2PO_4·2H_2O$, and 350±30 mg NaCl or wherein a unit dosage of the composition contains 650±60 mg of the free base of 4-Amino-(6R,S)-5,6,7,8-tetrahydro-L-biopterin, 60±50 mg of water of crystallization, 70±7 mg $Na_2HPO_4·2H_2O$, 12±2.5 mg $NaH_2PO_4·2H_2O$, and 350±30 mg NaCl.

93. The method of item 92, wherein reconstitution comprises providing a vial containing 1 g of the unit dosage and adding 50 ml water to 1 g of the unit dosage.

94. A compound having the formula (I):

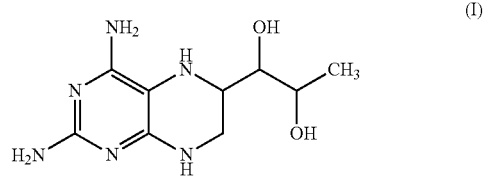 [SMILES: CC(O)C(O)C1CNc2nc(N)nc(N)c2N1]

for use in treating a human patient suffering from brain injury, wherein the use comprises (starting) administering to the patient within a time period of ≤12 hours after the occurrence of the brain injury a therapeutically effective amount of the compound having the formula (I).

95. A compound having the formula (I):

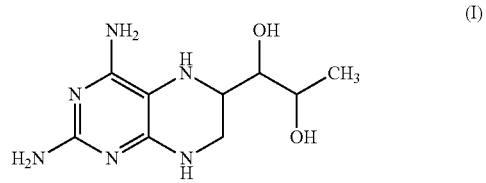 [SMILES: CC(O)C(O)C1CNc2nc(N)nc(N)c2N1]

for use in a method of increasing the value of the Extended Glasgow Outcome Scale (eGOS) of a human patient suffering from brain injury, thereby improving the condition of the patient, wherein the value of the Extended Glasgow Outcome Scale (eGOS) of the patient reaches eGOS level 7 or eGOS level 8 six months after the occurrence of the brain injury, wherein the use comprises (starting) administering to the patient within a time period of ≤12 hours after the occurrence of the brain injury a therapeutically effective amount of a compound having the formula (I).

96. A compound having the formula (I):

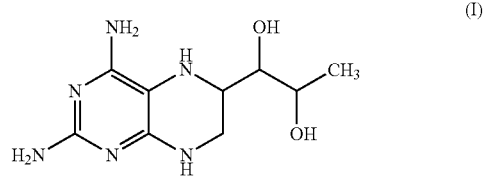 [SMILES: CC(O)C(O)C1CNc2nc(N)nc(N)c2N1]

for use in a method of increasing the value of the Extended Glasgow Outcome Scale (eGOS) of a human patient suffering from brain injury, thereby improving the condition of the patient, wherein the value of the Extended Glasgow Outcome Scale (eGOS) of the patient has increased by 2 or more six months after the occurrence of the brain injury, compared to the eGOS value of the patient determined three months after the occurrence of the traumatic brain injury, wherein the use comprises (starting) administering to the patient within a time period of ≤12 hours after the occurrence of the brain injury a therapeutically effective amount of the compound having the formula (I).

97. A compound having the formula (I):

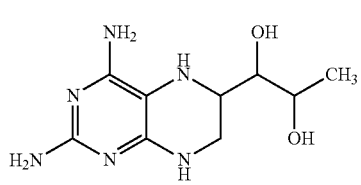

for use in treating a human patient suffering from brain injury, wherein the patient is a female of an age of 40 years or older, and wherein the method comprises (starting) administering to the patient within a time period of >12 hours after the occurrence of the brain injury a therapeutically effective amount of a compound having the formula (I).

98. The use of a compound having the formula (I):

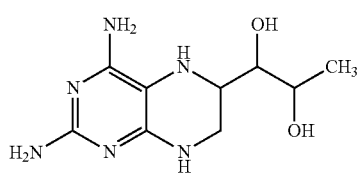

for preparing a pharmaceutical composition for treating a human patient suffering from brain injury, wherein the use comprises (starting) administering to the patient within a time period of ≤12 hours after the occurrence of the brain injury a therapeutically effective amount of the compound having the formula (I).

99. The use of a compound having the formula (I):

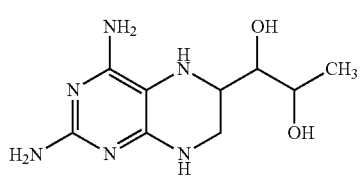

for preparing a pharmaceutical composition for increasing the value of the Extended Glasgow Outcome Scale (eGOS) of a human patient suffering from brain injury, thereby improving the condition of the patient, wherein the value of the Extended Glasgow Outcome Scale (eGOS) of the patient reaches eGOS level 7 or eGOS level 8 six months after the occurrence of the brain injury, wherein the use comprises (starting) administering to the patient within a time period of ≤12 hours after the occurrence of the brain injury a therapeutically effective amount of a compound having the formula (I).

100. The use of a compound having the formula (I):

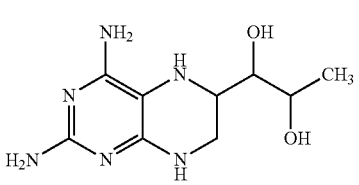

for preparing a pharmaceutical composition for increasing the value of the Extended Glasgow Outcome Scale (eGOS) of a human patient suffering from brain injury, thereby improving the condition of the patient, wherein the value of the Extended Glasgow Outcome Scale (eGOS) of the patient has increased by 2 or more six months after the occurrence of the brain injury, compared to the eGOS value of the patient determined three months after the occurrence of the traumatic brain injury, wherein the use comprises (starting) administering to the patient within a time period of ≤12 hours after the occurrence of the brain injury a therapeutically effective amount of the compound having the formula (I).

101. The use of a compound having the formula (I):

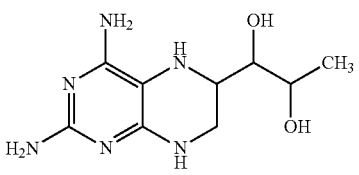

for preparing a pharmaceutical composition for treating a human patient suffering from brain injury, wherein the patient is a female of an age of 40 years or older, and wherein the method comprises (starting) administering to the patient within a time period of >12 hours after the occurrence of the brain injury a therapeutically effective amount of a compound having the formula (I).

What is claimed is:

1. A method of treating a human patient suffering from brain injury, wherein the patient is a female of an age of 40 years or older, and wherein the method comprises (starting) administering to the patient within a time period of 12 to 18 hours after the occurrence of the brain injury a therapeutically effective amount of a compound having the formula (I):

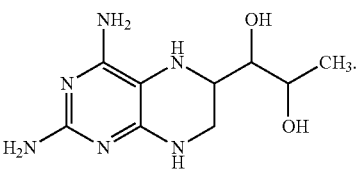

2. The method of claim 1, wherein the compound having the formula (I) is administered by infusion.

3. The method of claim 1, wherein the compound having the formula (I) is administered at a maximal daily dose in the range of 2.5 mg/kg body weight to 30.0 mg/kg body weight.

4. The method of claim 2, wherein the compound having the formula (I) is administered at a total dose of 2.5, 5.0, 7.5, 10.0, 12.5, 15.0, 17.5, 20.0, or 30.0 mg/kg body weight.

5. The method of claim 3, wherein the compound having the formula (I) is administered over a period of 12 to 96 hours.

6. The method of claim 5, wherein the compound having the formula (I) is administered over a period of 24 to 48 hours or over a period of 24 to 72 hours.

7. The method of claim 6, wherein the compound having the formula (I) is administered by infusion in a total dose of 17 mg/kg body weight over 48 hours, corresponding to a daily dose of 8.5 mg/kg body weight.

8. The method of claim 1, wherein the brain injury is selected from the group consisting of traumatic brain injury, non-traumatic brain injury, elevated intracranial pressure, and secondary brain injury.

9. The method of claim 8, wherein the brain injury is traumatic brain injury.

10. The method of claim 9, wherein the patient to be treated has been diagnosed with mild complicated, moderate or severe traumatic brain injury.

11. The method of claim 9, wherein the patient to be treated has been with diagnosed with traumatic brain injury of a Glasgow Coma Score (GCS)≥3.

12. The method of claim 10, wherein the traumatic brain injury requires intracranial pressure (ICP) monitoring.

13. The method of claim 9, wherein the value of an Extended Glasgow Outcome Scale (eGOS) of the patient increases by at least 1 level or by at least 2 levels when assessed six months after the occurrence of the traumatic brain injury as compared to an eGOS value of the patient determined three months after the occurrence of the traumatic brain injury.

14. The method of claim 13, wherein the eGOS value assessed six months after the occurrence of the traumatic brain injury increases by 2, 3.4 or 5 levels and compared to the eGOS value of the patient determined three months after the occurrence of the traumatic brain injury.

15. The method of claim 13, wherein the patient reaches eGOS level 7 or eGOS level 8 six months after the traumatic brain injury.

16. The method of claim 1, wherein the compound of formula (I) is 4-Amino-(6R,S)-5,6,7,8-tetrahydro-L-biopterin having the formula (Ia):

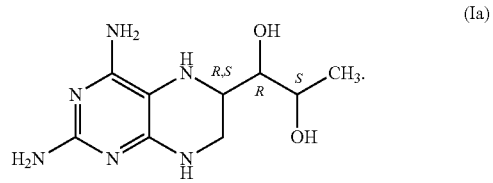

17. The method of claim 16, wherein the compound (Ia) is a diastereomeric mixture that comprises more (6R)-4-Amino-5, 6, 7, 8-tetrahydro-L-biopterin than (6S)-4-Amino-5, 6, 7, 8-tetrahydro-L-biopterin.

18. The method of claim 2, wherein infusion of the compound of formula (I) is carried out with a reconstituted solid composition of the compound of formula (I), wherein a unit dosage of the solid composition contains 650±60 mg of the free base of 4-Amino-(6R,S)-5,6,7,8-tetrahydro-L-biopterin, 140±30 mg of water of crystallization, 70±7 mg $Na_2HPO_4 \cdot 2\ H_2O$, 16.5±2 mg $NaH_2PO_4 \cdot 2\ H_2O$, and 350±30 mg NaCl or wherein a unit dosage of the composition contains 650±60 mg of the free base of 4-Amino-(6R,S)-5,6,7,8-tetrahydro-L-biopterin, 60±50 mg of water of crystallization, 70±7 mg $Na_2HPO_4 \cdot 2\ H_2O$, 12±2.5 mg $NaH_2PO_4 \cdot 2\ H_2O$, and 350±30 mg NaCl.

19. The method of claim 18, wherein reconstitution comprises providing a vial containing 1g of the unit dosage and adding 50 ml water to 1g of the unit dosage.

* * * * *